(12) United States Patent
Dewji et al.

(10) Patent No.: US 8,951,794 B2
(45) Date of Patent: Feb. 10, 2015

(54) METHODS AND COMPOSITIONS FOR TREATING NEURODEGENERATIVE DISORDERS AND ALZHEIMER'S DISEASE AND IMPROVING NORMAL MEMORY

(75) Inventors: Nazeen Dewji, San Diego, CA (US); S. Jonathan Singer, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 52 days.

(21) Appl. No.: 13/399,516

(22) Filed: Feb. 17, 2012

(65) Prior Publication Data

US 2012/0214235 A1 Aug. 23, 2012

Related U.S. Application Data

(63) Continuation of application No. 12/464,850, filed on May 12, 2009, now Pat. No. 8,129,334, which is a continuation-in-part of application No. 12/264,872, filed on Nov. 4, 2008, now abandoned, which is a continuation-in-part of application No. 11/693,926, filed on Mar. 30, 2007, now Pat. No. 7,851,228.

(60) Provisional application No. 60/788,524, filed on Mar. 31, 2006.

(51) Int. Cl.
*C12N 5/071* (2010.01)
*C07K 14/47* (2006.01)
*A61K 38/00* (2006.01)

(52) U.S. Cl.
CPC ............. *C07K 14/4711* (2013.01); *A61K 38/00* (2013.01)
USPC ....................................................... 435/375

(58) Field of Classification Search
None
See application file for complete search history.

(56) References Cited

U.S. PATENT DOCUMENTS

| | | |
|---|---|---|
| 6,653,088 B1 | 11/2003 | Czech et al. |
| 2002/0015939 A1 | 2/2002 | McCarthy |
| 2002/0016978 A1 | 2/2002 | Zheng |
| 2002/0064828 A1 | 5/2002 | Monteiro |
| 2002/0082211 A1 | 6/2002 | Arvizu |
| 2002/0086444 A1 | 7/2002 | Tanzi |
| 2003/0059938 A1 | 3/2003 | Annaert |
| 2003/0065141 A1 | 4/2003 | Carter |
| 2003/0113811 A1 | 6/2003 | Hale |
| 2003/0175278 A1 | 9/2003 | Monteiro |
| 2004/0143860 A1 | 7/2004 | St. George-Hyslop |
| 2004/0154047 A1 | 8/2004 | Scott |
| 2004/0205836 A1 | 10/2004 | Shen |
| 2004/0265891 A1 | 12/2004 | Arvizu |
| 2004/0267004 A1 | 12/2004 | Tohyama |
| 2005/0101766 A1 | 5/2005 | Blackstock |
| 2005/0214837 A1 | 9/2005 | St. George-Hyslop |
| 2005/0288212 A1 | 12/2005 | Hale |
| 2007/0231331 A1 | 10/2007 | Dewji et al. |
| 2009/0305946 A1 | 12/2009 | Dewji et al. |

FOREIGN PATENT DOCUMENTS

| | | |
|---|---|---|
| EP | 1967527 A1 | 9/2008 |
| WO | 98/04919 A1 | 2/1998 |
| WO | 2007092861 A2 | 8/2007 |
| WO | 2007/123680 A2 | 11/2007 |

OTHER PUBLICATIONS

Beglopoulos, Vassilios; X. Sun; C. A. Saura, C. A. Lemere; R. D. Kim; and J. Shen; The Journal of Biological Chemistry, Nov. 5, 2004, vol. 279, No. 45, pp. 46907-46914.

Cervantes, Sara; C. A. Suara; E. Pomares; R. Gonzales-Duarte; "Functional Implications of the Presenilin Dimerization" The Journal of Biological Chemistry, Aug. 27, 2004, vol. 279, No. 35, pp. 36519-36529.

Dewji, Nazneen N.; D. Mukhjopadhyay; and S. J. Singer; "An early specific cell-cell interaction occurs in the production of beta-amyloid in cell structures" PNAS Jan. 31, 2006, vol. 103, No. 5, pp. 1540-1545.

Dewji, Nazneen N., "Specific Intercellular binding of the beta-amyloid precursor protein to the presenilins induces intercelular singaling: its significance for Alzheimer's disease." Proc Natl Acad Sci USA, 1998, 95(25). pp. 15055-15060.

Dewji, Nazneen N., "The structure and functions of the presenilins." Cell Mol Life Sci, 2005, 62(10), pp. 1109-1119. Review.

Dewji, Nazneen N., "Presenilin structure in mechanisms leading to Alzheimer's disease." J Alzheimers Dis., 2006, 10(2-3), pp. 277-290. Review.

Dewji, Nazneen N.; D. Valdez; and S. J. Singer; "The presenilins turned inside out: Implications for their structires and functions" PNAS, Jan. 27, 2004, vol. 101, No. 4, pp. 1057-1062.

Dewji, Nazneen N.; C. Do; and S. J. Singer; "On the spurious endoproteolytic processing of the presenilin proteins in cultured cells and tissues" Proc. Natl. Acad. Sci U.S.A., Dec. 1997, vol. 94, pp. 14031-14036.

Dewji, Nazneen N., and S. J. Singer, "The seven-transmembrane spanning topography of the Alzheimer disease-related presenilin proteins in the plasma membranes of cultured cells" Proc. Natl. Acad. Sci. U.S.A., Dec. 1997, vol. 94, pp. 14025-14030.

Dewji, Nazneen N., and S. J. Singer, "Cell surface expression of the Alzheimer disease-related prsenilin proteins" Proc. Natl. Acad. Sci. U.S.A., Sep. 1997, vol. 94, pp. 9926-9931.

Dewji, Nazneen N., and S. J. Singer, "Genetic Clues to Alzheimer's Disease" Science, Jan. 12, 1996, vol. 271, pp. 159-160.

Dewji, Nazneen N., and S. J. Singer, "Specific transcellular binding between membrane proteins crucial to Alzheimer disease" Proc. Natl. Acad. Sci. U.S.A., Oct. 1996, vol. 93, pp. 12575-12580.

(Continued)

*Primary Examiner* — John Ulm

(74) *Attorney, Agent, or Firm* — Joseph R. Baker, Jr.; Gavrilovich, Dodd & Lindsey, LLP

(57) ABSTRACT

The disclosure relates generally to neurodegenerative disorders and more specifically to a group of presenilin/G-protein/c-src binding polypeptides and methods of use for modulating signaling and progression of Alzheimer's disease.

11 Claims, 20 Drawing Sheets

(56) References Cited

OTHER PUBLICATIONS

Gandy, Sam; M. K. Doeven; and B. Poolman; "Alzheimer disease: presenilin springs a leak" Nature Medicine; Oct. 2006, vol. 12, No. 10, pp. 1121-1123.

Lunter, Pim, Supplementary European Search Report, Date of Completion of Search: Mar. 4, 2009, European Patent Application No: EP07754428.

Pradier, Laurent; N. Carpentier; L. Delalonde; N. Clavel; M-D Bock; L. Buee; L. Mercken; B. Tocque; and C. Czech; "Mapping the APP/Presenilin (PS) Binding Domains: The Hydrophilic N-Terminus of PS2 Is Sufficient for Interaction with APP and Can Displace APP/PS1 Interaction" Neurobiology of Disease, 1999, vol. 6, pp. 43-55.

Saura, Carlos A.; S-Y Choi; V. Beglopoulos; S. Maikani; D. Zhang; B. S. Shankaranarayana Roa; S. Chattarji; R. J. Kelleher, III; E. R. Kandel; K. Duff; A. Kirkwood; and J. Shen; "Loss of Presenilin Function Causes Impairments of Memory and Synaptic Plasticity Followed by Age-Dependent Neurodegeneration" Neuron, Apr. 8, 2004, vol. 42, pp. 23-36.

Saura, Carlos A.; G. Chen; S. Malkani; S-Y Choi; R. H. Takahashi; D. Zhang; G. K. Gouras; A. Kirkwood; R. G. M. Morris; and J. Shen "Conditional Inactivation of Presenilin 1 Prevents Amyloid Accumulation and Temporarily Rescues Contextual and Spatial Working Memory Impairments in Amyloid Precursor Protein Tansgenic Mice" The Journal of Neuroscience, Jul. 20, 2005, vol. 25, No. 29, pp. 6755-6764.

Smine, Abdelkrim; X. Xu; K. Nishiyama; T. Katada; P. Gambetti; S. P. Yadav; X. Wu; Y-C Shi; S. Yasuhara; V. Homberger; and T. Okamoto "Regulation of Brain G-protein Go by Alzheimer's Disease Gene Presenilin-1" The Journal of Biological Chemistry, Jun. 26, 1998, vol. 273, No. 26, pp. 16281-16288.

Georgakopoulos, Anastasios, "Metalloproteinase/Presenilin1 processing of ephrinB regulates EphB-induced Src phosphorylation and sigaling", The EMBO Journal, 2006, vol. 25, pp. 1242-1252.

Ulm, John D., Transmittal of International Search Report and Written Opinion, International Search Report, and Written Opinion, PCT/US07/07908, Aug. 25, 2008.

Merchen et al., "Characterization of human presenilin-1 using N-terminal specific monoclonal antibodies: Evidence that Alzheimer mutations affect proteolytic processing," FEBS Letters, Jul. 8, 1996, vol. 389, No. 3, pp. 297-303.

Kitano et al., "Production of polyclonal antibody specific for human natiuretic peptide receptor B," J. of Immunological Methods, Aug. 14, 1996, vol. 194, No. 2, pp. 147-153.

Fung, Ricky, Australian Office Action, Appl. No. 2010249051, IP Australia, Jan. 17, 2013 and Mar. 26, 2013.

Barrette, Christian, Canadian Office Action, Appl. No. 2,648,096, Canadian Intellectual Property Office, Dec. 6, 2013 and Jan. 7, 2013.

Schmitz, Till, Extended European Search Report, Appl. No. 10775501.9, European Patent Office, Jan. 9, 2013.

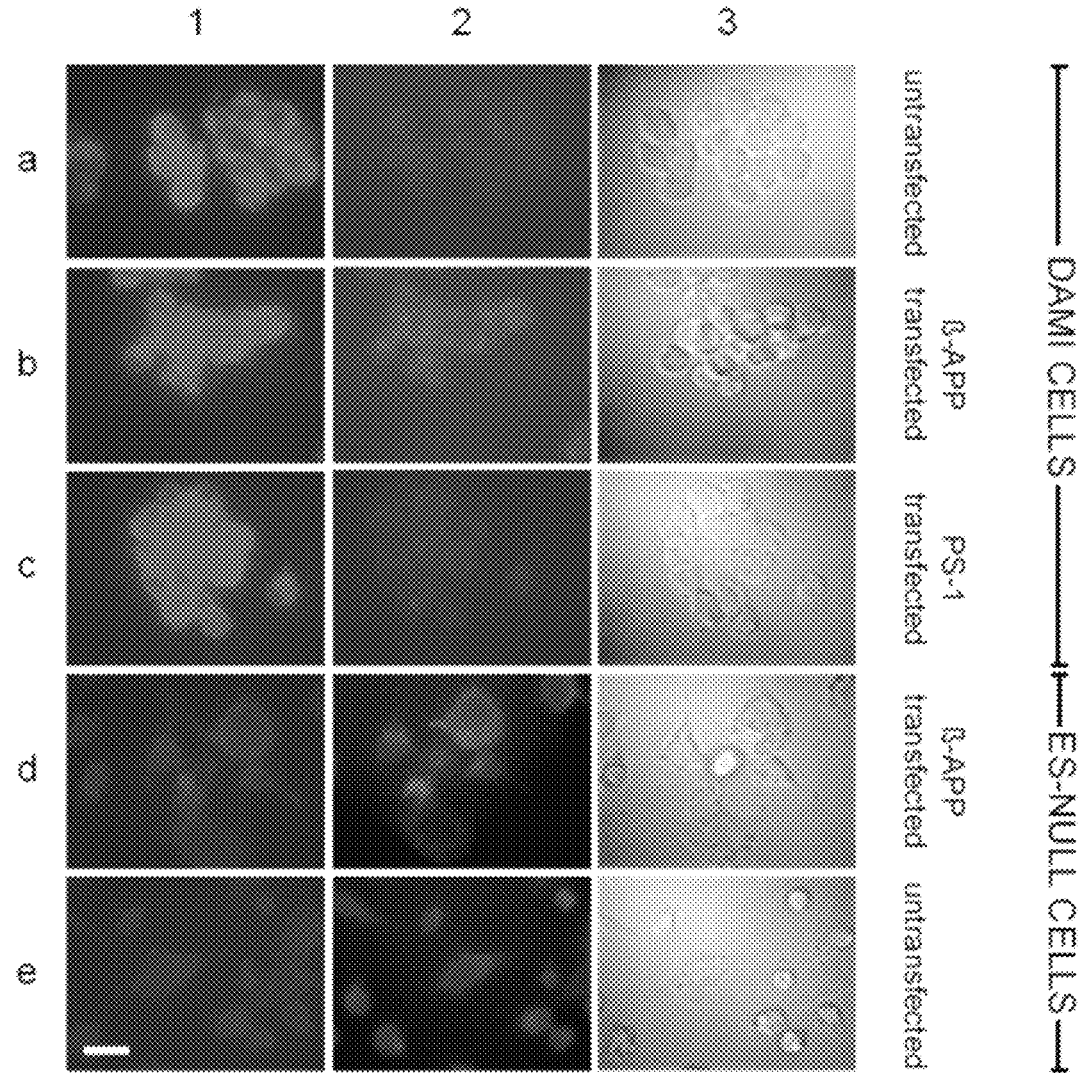

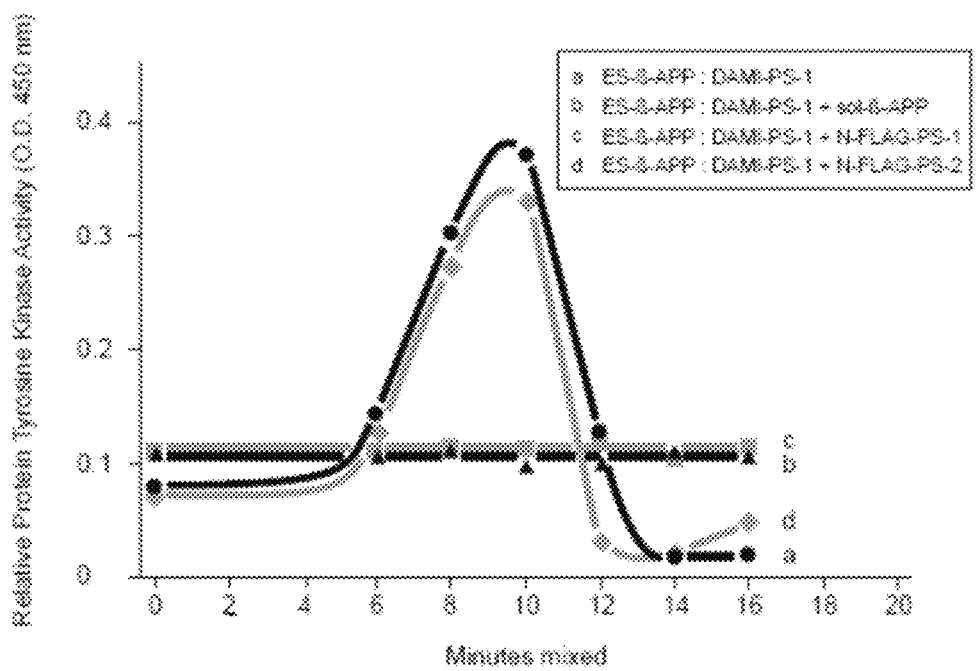

FIGURE 7A-B
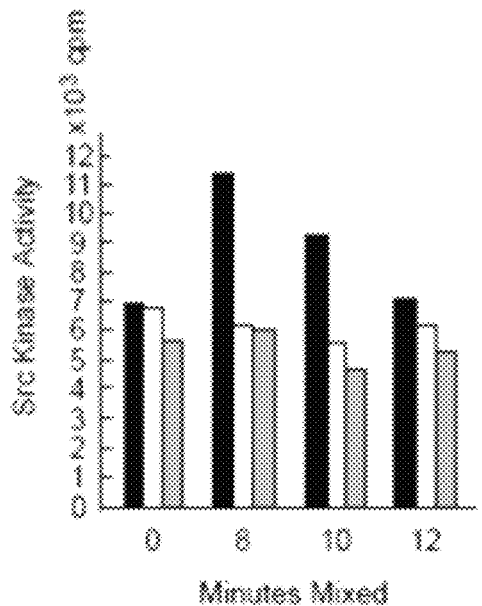
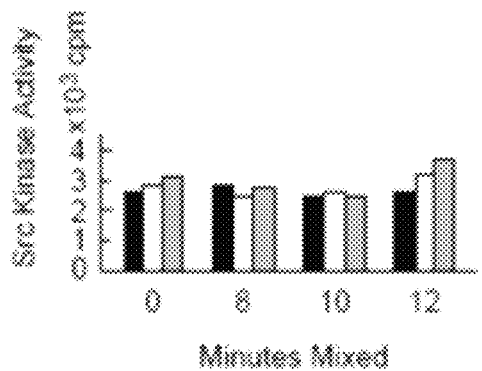

FIGURE 7C-D
C  Extracts of β-APP-transfected DAMI with PS-2-transfected DAMI Cell Mixtures
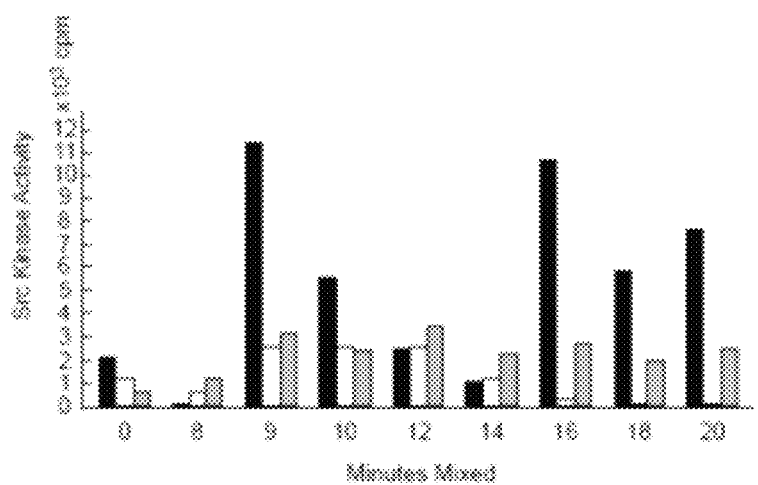
D  Extracts of pcDNA3-transfected DAMI with PS-2-transfected DAMI Cell Mixtures
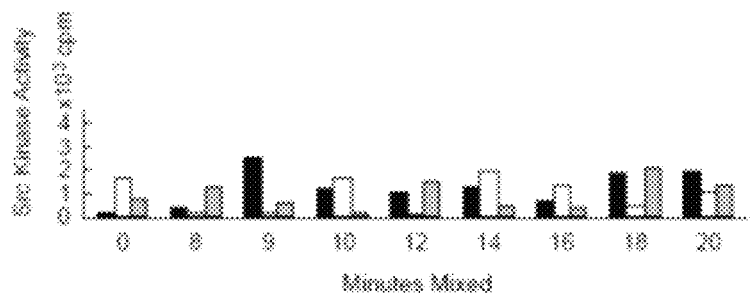

Extracts of β-APP-transfected DAMI with PS-1-transfected DAMI Cell Mixtures

Figure 9
a   Western blot hybridization
β-APP-transfected DAMI + PS-1-transfected DAMI
Mixed Cell Extracts
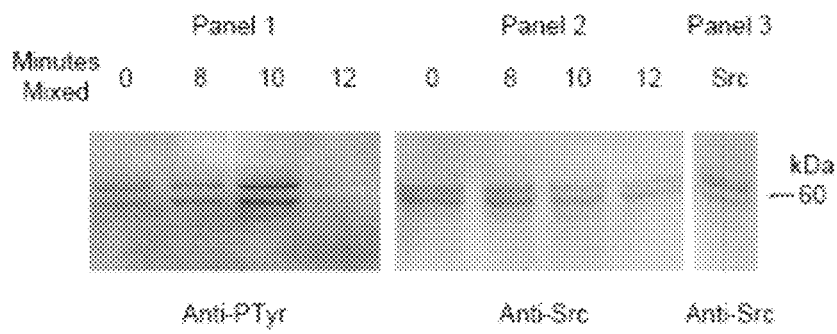
β-APP-transfected ES-NULL + PS-1-transfected DAMI
Mixed Cell Extracts
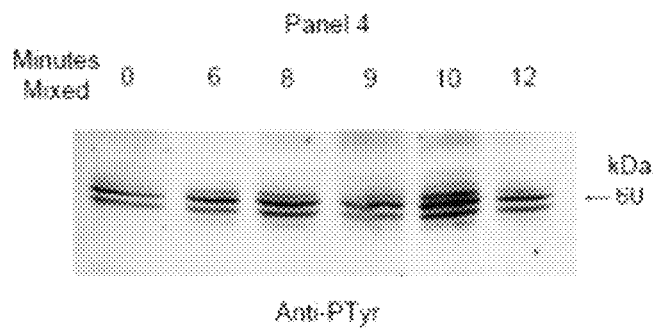
b   In-vitro phosphorylation following Anti-Src treatment
β-APP-transfected DAMI + PS-1-transfected DAMI
Mixed Cell Extracts
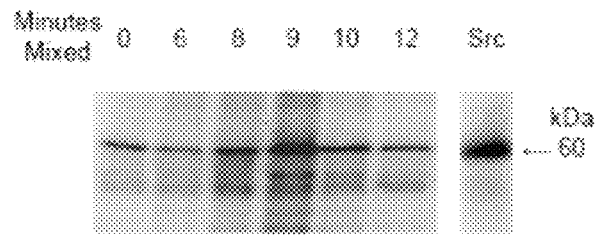

Figure 10
β-APP-transfected DAMI + PS-2-transfected DAMI Mixed Cell Extracts
a  Western blot hybridization
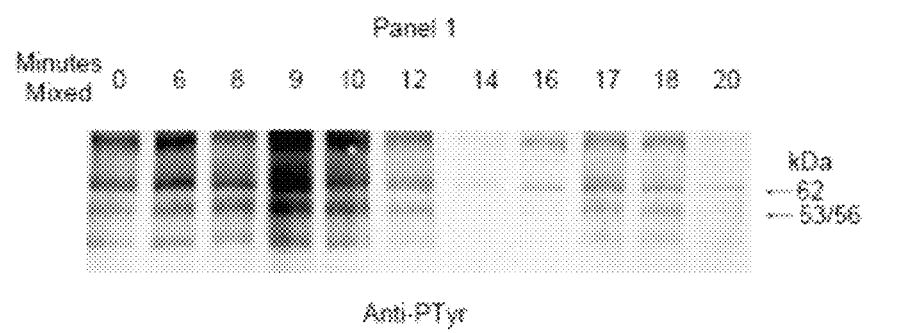
Anti-PTyr
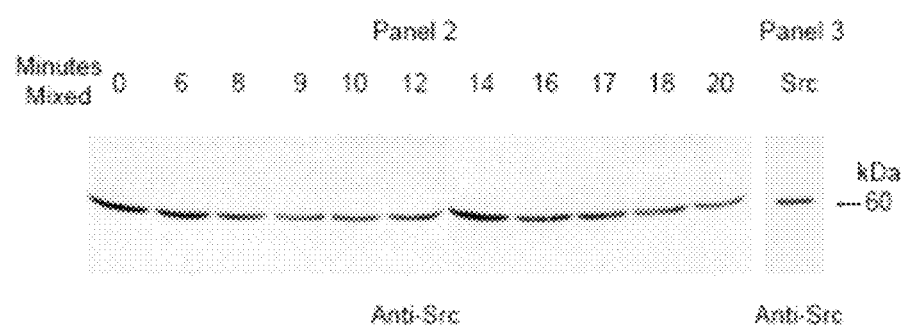
Anti-Src          Anti-Src
b  In-vitro phosphorylation following Anti-Src treatment

Figure 11
β-APP-transfected DAMI + PS-2-transfected DAMI Mixed Cell Extracts
a  Western blot hybridization
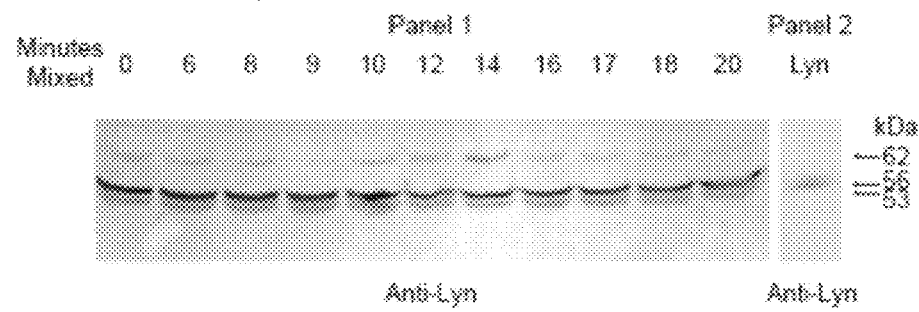
b  Western blot hybridization
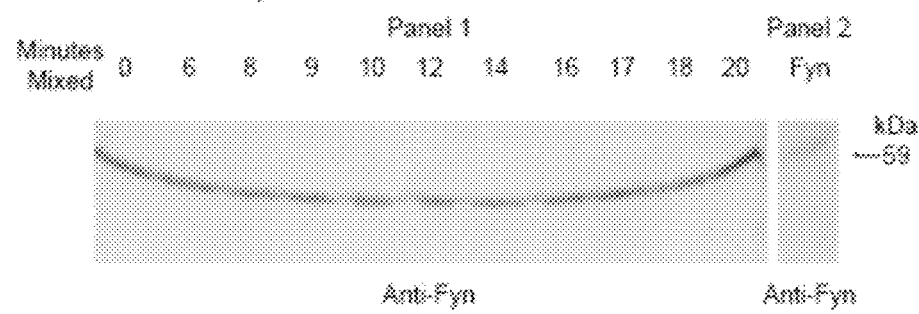
c  In-vitro phosphorylation following Anti-Lyn treatment
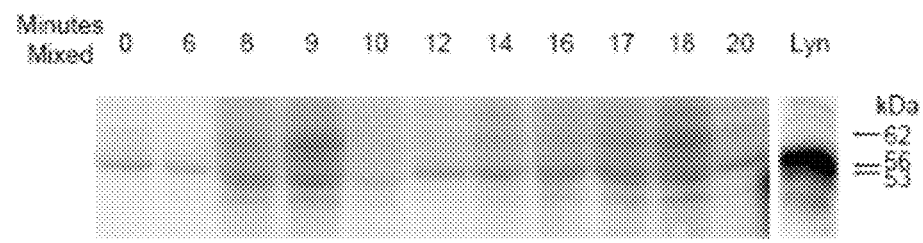
d  In-vitro phosphorylation following Anti-Fyn treatment
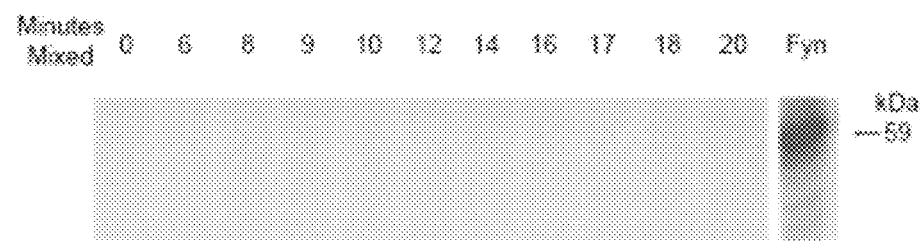

4 kDa —
Aβ
     1    2    3    4    5    6

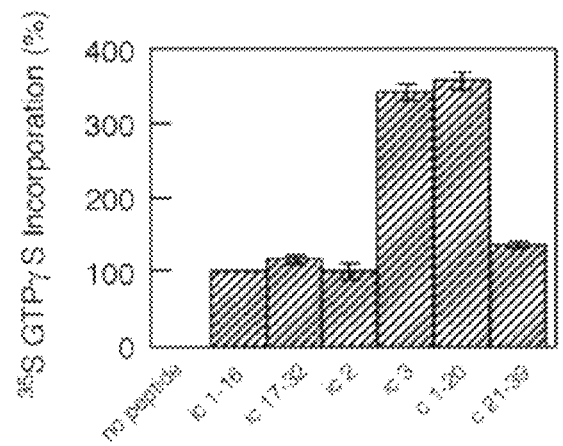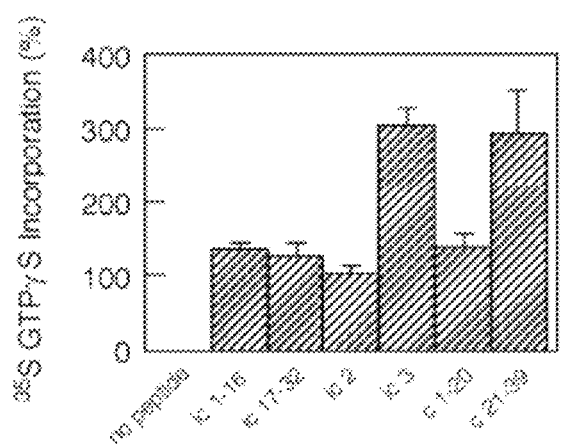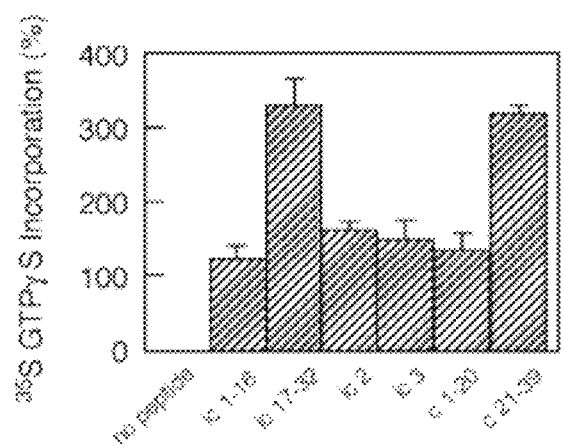
FIGURE 25

METHODS AND COMPOSITIONS FOR TREATING NEURODEGENERATIVE DISORDERS AND ALZHEIMER'S DISEASE AND IMPROVING NORMAL MEMORY

CROSS REFERENCE TO RELATED APPLICATIONS

This application is a continuation of U.S. patent application Ser. No. 12/464,850, filed May 12, 2009 (now U.S. Pat. No. 8,129,334), which is a continuation-in-part and claims priority to U.S. patent application Ser. No. 12/264,872, filed Nov. 4, 2008 (abandoned), which application is a continuation-in-part of U.S. application Ser. No. 11/693,926, filed Mar. 30, 2007 (now U.S. Pat. No. 7,851,228), which application claims priority to U.S. Provisional Application Ser. No. 60/788,524 filed Mar. 31, 2006, the disclosures of which are incorporated herein by reference.

STATEMENT REGARDING FEDERAL SPONSORED RESEARCH

This invention was made with Government support under Grant Nos. AG017888, NS055161, NS27580, and NS44768 awarded by the National Institutes of Health. The Government has certain rights in the invention.

FIELD OF THE DISCLOSURE

The invention relates generally to treating neurodegenerative disorders and more specifically to a group of presenilin/G-protein/c-src binding polypeptides and small molecule drugs designed to modulate the physiologic interactions of polypeptides required for the production of β-amyloid (Aβ).

BACKGROUND

Alzheimer's disease (AD) is a degenerative disorder of the human central nervous system characterized by progressive memory impairment and cognitive and intellectual decline during mid to late adult life. The disease is accompanied by a variety of neuropathologic features principal among which are the presence in the brain of amyloid plaques and the neurofibrillary degeneration of neurons. The etiology of this disease is complex, although in about 10% of AD cases it appears to be familial, being inherited as an autosomal dominant trait. Among these inherited forms of AD, there are at least four different genes, some of whose mutants confer inherited susceptibility to this disease. The σ4 (Cys112Arg) allelic polymorphism of the Apolipoprotein E (ApoE) gene has been associated with AD in a significant proportion of cases with onset late in life. A very small proportion of familial cases with onset before age 65 years have been associated with mutations in the β-amyloid precursor protein (APP) gene on chromosome 21. A third locus associated with a larger proportion of cases with early onset AD has recently been mapped to chromosome 14q24.3. The majority (70-80%) of heritable, early-onset AD maps to chromosome 14 and appears to result from one of more than 20 different amino-acid substitutions within the protein presenilin-1 (PS1). A similar, although less common, AD-risk locus on chromosome 1 encodes a protein, presenilin-2 (PS-2, highly homologous to PS-1). Based upon mRNA detection, the presenilins appear to be ubiquitously expressed proteins, suggesting that they are normally housekeeping proteins required by many cell types.

Presenilin 1 is a 43-45 kDa polypeptide and presenilin 2 is a 53-55 kDa polypeptide. Presenilins are integral proteins of membranes present in high molecular weight complexes that are detergent sensitive. Three protein components of the complexes in addition to presenilin are known.

SUMMARY

The disclosure provides methods and compositions for identifying agents that modulate activity of presenilins. Accordingly, the methods and compositions provided herein may be used to modulate the production of Aβ in the brain by (1): interfering with the binding of the extra-cellular N-terminal domain of β-APP with PS-1 or PS-2; or (2) by using as an inhibiting agent a small peptidomimetic molecule, or a small fragment of an antibody molecule directed to an epitope on either the interacting surfaces of the β-APP or PS molecules. In one aspect, the peptide is a soluble N-terminal domain of PS-1 or -2.

In one embodiment, a method of identifying an agent that modulates presenilin G-protein coupled receptor (GPCR) activity is provided. The method includes a) contacting presenilin, or fragment thereof, with a G-protein under conditions that would permit binding of the G-protein to presenilin; b) prior to, simultaneously with, or subsequent to a), contacting presenilin, or fragment thereof, with an agent; c) monitoring presenilin-mediated binding to the G-protein; and d) determining whether the agent modulates presenilin binding to the G-protein thereby identifying an agent that modulates presenilin G-protein coupled receptor (GPCR) activity. In some aspects the modulating is by inhibition of presenilin binding to the G-protein. In other aspects, the modulating is by activating presenilin binding to the G-protein. The presenilin can be presenilin-1 (PS-1) or presenilin-2 (PS-2). The G-protein can be $G_o$, $G_s$, $G_i$, $G_z$ or $G_q$.

The disclosure further provides methods of treating Alzheimer's Disease or inhibiting the onset of Alzheimer's Disease comprising contacting a subject with an agent identified by the methods described above.

In some aspects, the agent includes a naturally occurring or synthetic polypeptide or oligopeptide, a peptidomimetic, a small organic molecule, a polysaccharide, a lipid, a fatty acid, a polynucleotide, an RNAi or siRNA, an asRNA, or an oligonucleotide.

The methods provided herein may be conducted in vitro or in vivo. In some aspects, a method further includes contacting the presenilin with β-APP prior to, simultaneously with, or subsequent to contacting the presenilin with the G-protein.

In another embodiment, a method of identifying an agent that modulates presenilin-mediated Src protein kinase activity is provided. The method includes a) contacting presenilin, or fragment thereof, with β-APP under conditions that would permit binding of β-APP to presenilin; b) prior to, simultaneously with, or subsequent to a), contacting presenilin, or fragment thereof, with an agent; c) monitoring presenilin-mediated Src protein kinase activity; and d) determining whether the agent modulates presenilin-mediated Src protein kinase activity.

Also provided herein are compositions and methods for treating neurodegenerative disorders, and more specifically to a group of presenilin/G-protein/c-src binding polypeptides and small molecule drugs designed to modulate the physiologic interactions of polypeptides required for the production of β-amyloid (Aβ), the oligopeptide that is the primary neurotoxic agent in Alzheimer's disease (AD). The disclosure provides methods and compositions that reduce the amount of Aβ in the brain to an extent that significantly decreases the neurotoxicity in AD, or delays the onset, or decreases the severity of the disease. Such methods and compositions are useful for modulating signaling and progression of Alzheimer's Disease and improve memory.

The disclosure also provides a method of inhibiting the production of Aβ with a small molecule agent that inhibits the interaction of PS-1 or PS-2 with the G-proteins $G_{oA}$ and $G_{oB}$. The cytoplasmic C-terminal and other domains of PS-1 or PS-2 have been shown to be the sites of interaction of $G_{oA}$ and/or $G_{oB}$ with PS, and that this $G_o$-PS intracellular binding is required for subsequent Aβ production, presumably via the downstream results of this binding process.

The disclosure similarly provides a method of inhibiting the production of Aβ by contacting a cell expressing a PS-1 and/or PS-2 with an agent that interferes with the downstream results of PS-1 and/or PS-2 binding to $G_o$ such as $G_o$ activation with phospholipase C.

The disclosure also provides a method of inhibiting the production of Aβ by the use of small molecules, peptides or antibodies selected to interfere with the activities of members of the Src family of tyrosine kinases.

The disclosure also provides a method of inhibiting the production of Aβ by the use of small molecules, peptides or antibodies selected to interfere with the interaction between a PS-1 and/or PS-2 and a β-APP.

The disclosure further provides a method of assaying for inhibitors of Aβ production in a cell culture system consisting of a first transfected cell type expressing β-APP but no PS mixed with a second cell type expressing PS but no β-APP. The inhibitory effect of an agent added to this mixed cell culture would be measured from the activities of several likely downstream effects of (a) the $G_{oA}$ and $G_{oB}$ interaction with PS-1 and PS-2; or (b) the Src family of tyrosine kinases; or (c) the interaction of N-terminal domain of βAPP with the N-terminal domain of PS-1 and/or PS-2.

The disclosure provides an isolated polypeptide consisting essentially of the amino acid sequence of an N-terminal fragment of a Presenilin-1 or -2 polypeptide. In one embodiment, the isolated polypeptide consists essentially of an amino acid sequence selected from the group consisting of: (i) N-DEEEDEEL-COOH (SEQ ID NO:5), (ii) SEQ ID NO:5 further including 1-50 additional amino acids at either the N- or C-terminal end wherein the peptide inhibits cell-cell interaction, inhibits Aβ production or binds to a β-APP, (iii) N-RRSLGHPEPLSNGRP-COOH (SEQ ID NO:6), (iv) SEQ ID NO:6 further including 1-5 conservative amino acid substitutions, wherein the peptide inhibits cell-cell interaction, inhibits Aβ production or binds to a β-APP, (v) a sequence of (iii) or (iv) further including 1-50 additional amino acids at the N- or C-terminus, wherein the peptide inhibits cell-cell interaction, inhibits Aβ production or binds to a β-APP, (vi) N—RRSLGHPEPLSNGRPQGN-SRQVVEQDEEEDEELTLKYGAK-COOH (SEQ ID NO:7), (vii) SEQ ID NO:7 further including 1-5 conservative amino acid substitutions, wherein the peptide inhibits cell-cell interaction, inhibits Aβ production or binds to a β-APP, (viii) a sequence consisting of (vi) or (vii) further including 1-50 additional amino acids at the N- or C-terminus, wherein the peptide inhibits cell-cell interaction, inhibits Aβ production or binds to a β-APP, and (ix) any of the foregoing comprising an unnatural amino acid or D-amino acid wherein the peptide inhibits cell-cell interaction, inhibits Aβ production or binds to a β-APP. In one embodiment, the peptide comprise an amino acid sequence of the N-terminal fragment of about 5-80 amino acids in length and having a sequence as set forth in SEQ ID NO:2 or 4 from amino acid 1 to about amino acid 80. In another embodiment, the peptide may be linked to a second peptide useful for purification, or formation of oligomers.

In another embodiment the disclosure provides an oligomer comprising at least two peptide that interact with a presenilin or β-APP. The at least two peptides may be the same or different or may be directly fused/linked or fused/linked by a linking domain or peptide.

The disclosure also provides an isolated polynucleotide consisting essentially of a nucleotide sequence encoding a peptide or oligomer described herein. The polynucleotide can be incorporated in to an expression vector. The polynucleotide or expression vector may be transfected or transformed into a host cell.

The disclosure provides a method for expressing a polypeptide as described above and herein, comprising culturing a recombinant host cell into which a polynucleotide encoding the polypeptide has been introduced.

The disclosure also provides a method of inhibiting the production of Aβ comprising contacting a cell with an interfering agent that interferes with the intercellular binding of β-APP and presenilin-1 (PS-1) and/or presenilin-2 (PS-2) or the activation of a G-protein. In one embodiment, the interfering agent comprises an extracellular domain of a presenilin-1 or -2. In another embodiment, the extracellular domain comprises an N-terminal region of PS-1 or PS-2, or oligomers thereof. In yet another embodiment, the interfering agent comprises a soluble N-terminal domain of PS-1 or -2. In yet another embodiment, the interfering agent comprises an amino acid sequence selected from the group consisting of: (i) N-DEEEDEEL-COOH (SEQ ID NO:5), (ii) SEQ ID NO:5 further including 1-50 additional amino acids at either the N- or C-terminal end wherein the peptide inhibits cell-cell interaction, inhibits Aβ production or binds to a β-APP, (iii) N-RRSLGHPEPLSNGRP-COOH (SEQ ID NO:6), (iv) SEQ ID NO:6 further including 1-5 conservative amino acid substitutions, wherein the peptide inhibits cell-cell interaction, inhibits Aβ production or binds to a β-APP, (v) a sequence of (iii) or (iv) further including 1-50 additional amino acids at the N- or C-terminus, wherein the peptide inhibits cell-cell interaction, inhibits Aβ production or binds to a β-APP, (vi) N—RRSLGHPEPLSNGRPQGN-SRQVVEQDEEEDEELTLKYGAK-COOH (SEQ ID NO:7), (vii) SEQ ID NO:7 further including 1-5 conservative amino acid substitutions, wherein the peptide inhibits cell-cell interaction, inhibits Aβ production or binds to a β-APP, (viii) a sequence consisting of (vi) or (vii) further including 1-50 additional amino acids at the N- or C-terminus, wherein the peptide inhibits cell-cell interaction, inhibits Aβ production or binds to a β-APP, and (ix) any of the foregoing comprising an unnatural amino acid or D-amino acid wherein the peptide inhibits cell-cell interaction, inhibits Aβ production or binds to a β-APP. The disclosure also provides a method of inhibiting the production of Aβ by contacting a cell expressing PS-1 and/or PS-2 with an agent that inhibits the interaction of PS-1 and/or PS-2 with a G-protein. In one embodiment, the agent interacts with the C-terminal tail and/or other cytoplasmic domain of PS-1 and/or 2 with a $G_{oA}$ and/or $G_{oB}$.

In another aspect, the disclosure provides a method of improving cognitive function and/or memory in a subject. The method includes administering an agent that inhibits the interaction of PS-1 and/or PS-2 with G-protein, $G_{oA}$ and $G_{oB}$. In one approach, the agent interacts with the C-terminal tail and/or other cytoplasmic domains of PS-1 and/or 2 that interact with $G_{oA}$ and/or $G_{oB}$. The agent may also interfere with the downstream results of PS-1 and/or PS-2 binding to $G_o$ such as $G_o$ activation with phospholipase C. In another approach, the agent inhibits the activity of members of the Src family of tyrosine kinases in cells expressing PS-1 and/or PS-2. In each case the agent would be administered in an amount to improve cognitive function and/or memory retention compared to a control subject.

DESCRIPTION OF DRAWINGS

FIG. 5 shows a plurality of panels of immunofluorescence microscopic labeling of fixed cells. Row a) Double immunofluorescence microscopic labeling of untransfected, fixed but not permeabilized, DAMI cells with primary rat Mab #1563 to human PS-1 N-terminal domain (Panel 1) and FITC conjugated anti-rat IgG secondary antibody shows cell-surface immunolabeling of endogenous PS-1 amino terminal domain. Panel 2 shows the same cells do not express appreciable amounts of cell-surface β-APP when labeled with Mab #348 to the β-APP extracellular domain and TRITC-conjugated anti-mouse IgG secondary antibody (red). Panel 3 shows the Nomarski images of cells in panels 1 and 2. Row b) Double Immunofluorescence microscopic labeling of β-APP-transfected, fixed but not permeabilized, DAMI cells shows cell-surface expressed β-APP when labeled with Mab #348 to the β-APP extracellular domain and TRITC-conjugated secondary antibody (Panel 2). Panels 1 and 3, the same cells treated as for FIG. 5 row a. Row c) Immunofluorescence microscopic labeling of PS-1-transfected, fixed but not permeabilized, DAMI cells shows high expression of cell-surface PS-1 (Panel 1) but not β-APP (Panel 2) when labeled with the same primary and secondary antibodies described in a. Panel 3 shows the Nomarski image of cells in panels 1 and 2. These experiments show that transfection of the DAMI cells with PS-1 does not call forth cell surface expression of β-APP. Row d) Immunofluorescence microscopic labeling of β-APP-transfected, fixed but not permeabilized ES cells, double-null for PS-1 and PS-2. Cells show cell-surface expressed β-APP when labeled with Mab #348 to the β-APP extracellular domain and TRITC-conjugated secondary antibody (Panel 2). Panel 1 shows the result of labeling with primary rat Mab #1563 to human PS-1 N-terminal domain and FITC conjugated appropriate secondary antibody, indicating the expected absence of PS-1 on the surfaces of ES double-null cells. Panel 3 shows Nomarski image of cells in Panels 1 and 2. Row e) Immunofluorescence microscopic labeling of untransfected, fixed but not permeabilized ES cells, double-null for PS-1 and PS-2. Cells show cell-surface expressed endogenous mouse β-APP when labeled with Mab #348 to the β-APP extracellular domain and TRITC-conjugated secondary antibody (Panel 2). Panels 1 and 3 labeled as in d; no cell surface labeling for PS-1 (Panel 1) is observed in these untransfected ES cells. Bar, 20 μm.

FIG. 6 shows that within minutes after mixing β-APP-only expressing transfected ES cells with PS-1 only expressing transfected DAMI cells, a transient protein tyrosine phosphorylation process arises in the mixed cell culture, as detected by ELISA analyses of the cell extracts. This activity peaked at ~8-10 mins after mixing line (a). The same experiment carried out in the presence of 25 μg purified soluble β-APP line (b) or 25 μg purified peptide of N-terminal domain of PS-1 fused to FLAG line (c) showed none of the increases observed in line (a). The addition of 25 μg of purified peptide of the non-specific N-terminal domain of PS-2 fused to FLAG line (d), however, resulted in very similar transient increases in protein tyrosine kinase activity to line (a).

FIG. 7A-D shows experiments to determine the nature of the tyrosine phosphorylating enzyme activity in FIG. 6. Src family kinase assay with synthetic peptides. a and b: β-APP: PS-1 interaction with separately transfected DAMI cells as a function of time after mixing. Src kinase activity was assayed using the Src family substrate peptide {lys19}cdc2(6-20)-NH$_2$ (black bars) and control peptides {lys19Phe15}cdc2(6-20)NH2 (white bars) and {lys19ser14val12}cdc2(6-20)NH2 (gray bars) for both the β-APP:PS-1 (a) and control pcDNA3: PS-1 (b) interactions. c and d: β-APP:PS-2 interaction with separately transfected DAMI cells as a function of time after mixing. Src kinase activity was assayed using the Src family substrate peptide {lys19}cdc2(6-20)-NH$_2$ (black bars) and control peptides {lys19Phe15}cdc2(6-20)NH2 (white bars) and {lys19ser14val12}cdc2(6-20)NH$_2$ (gray bars) for both the β-APP:PS-2 (c) and control pcDNA3:PS-2 (d) interactions.

FIG. 9A-B shows β-APP:PS-1 intercellular interaction: C-Src activity in extracts of mixed cells. a. Western Immunoblot. β-APP:PS-1 interactions with mixtures of separately transfected DAMI cells. Western immunoblot with primary anti-PTyr polyclonal antibodies (Panel 1) and anti-pp60c-src monoclonal antibodies (Panel 2) from the same experiment in which β-APP-transfected DAMI cells were mixed with PS-1-transfected DAMI cells for 0-12 mins. Panel 3: Antibody labeling of control pp60c-src protein with the pp60c-src antibodies. Panel 4: Western immunoblots with primary anti-PTyr antibodies, as in Panel 1, from experiments in which 13-APP-transfected ES double-null cells were interacted with PS-1-transfected DAMI cells. b. Autoradiograph of in-vitro phosphorylated proteins. Extracts of separately transfected β-APP and PS-1 DAMI cell mixtures at 0-12 mins after mixing were first immunoprecipitated with antibodies to c-Src and then phosphorylated in vitro with $\gamma^{32}$P-ATP. Autophosphorylation reactions were subjected to SDS-PAGE followed by autoradiography.

FIG. 10A-B shows β-APP:PS-2 intercellular interaction: C-Src activity in extracts of mixed cells. a. Western Immunoblot. β-APP:PS-2 interaction in extracts of separately transfected and mixed DAMI cells as a function of time after mixing. Panels 1 and 2: Same as FIG. 9a except that PS-2-transfected DAMI cells replaced PS-1-transfected cells in the intercellular interaction with β-APP and cells were mixed from 1-20 mins. b. Autoradiograph of in-vitro phosphorylated proteins. Same extracts as in part a. Same as 5b except that PS-2-transfected DAMI cells replaced PS-1-transfected DAMI cells in the intercellular interaction with β-APP.

FIG. 11A-D shows β-APP:PS-2 intercellular interaction: Activity of Lyn and Fyn in extracts of mixed cells. a and b. Western Immunoblots: β-APP:PS-2 interaction. Western immunoblot with primary anti-Lyn polyclonal antibodies (a, Panel 1) and anti-Fyn polyclonal antibodies (b, Panel 1) from the same experiment in which β-APP-transfected DAMI cells were mixed with PS-2-transfected DAMI cells for 0-20 mins and extracts made. No change with time in concentration of either Lyn or Fyn protein was observed. Panel 2: Antibody labeling of control Lyn (a) and Fyn (b) protein with their respective antibodies. c and d. Autoradiograph of in-vitro phosphorylated proteins: β-APP:PS-2 interaction. Extracts of mixtures of β-APP and PS-2 mixed transfected cells at 0-20 mins after mixing were first immunoprecipitated with antibodies to Lyn (c) or Fyn (d) and then phosphorylated in vitro with $^{32}$P-ATP. Autophosphorylation reaction products were subjected to SDS-PAGE followed by autoradiography.

FIG. 25A-C shows $^{35}$S-GTPγS incorporation in the presence of various intracellular domains for different G-Proteins. (a) G$\alpha_o$ (b) G$_q$, and (c) G$_s$.

DETAILED DESCRIPTION

Figure 1:
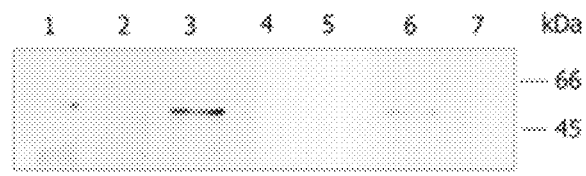
FIG. 1 shows a representative study to determine if PS-1 is a GPCR. Extracts of different cell cultures were analyzed in order to determine whether $G_o$ interacts with PS-1, including the necessary controls. In each lane, the particular cell extracts were first immunoprecipitated with a monoclonal Ab (MAb) directed to PS-1; the immunoprecipitate was then dissolved and subjected to SDS-PAGE electrophoresis, and the resulting gel was Western blotted with an antibody directed to $G_o$ (this antibody recognizes both $G_{oA}$ and $G_{oB}$) Lane 1 is a control of an extract of untransfected ES (PS-1$^{-/-}$/PS-2$^{-/-}$) cells. As expected, this extract showed that no $G_{oA}$ (or $G_{oB}$) was immunoprecipitated with Ab to PS-1. Lane 2 is an extract of ES cells, that had first been transfected with PS-1 only, but not with $G_{oA}$. No protein band was observed for $G_{oA}$; this was another control experiment. Lane 3 is an extract of the ES cells transfected with both PS-1 and $G_{oA}$. In this extract, $G_{oA}$ is immunoprecipitated along with the PS-1, showing that PS-1 was bound to $G_{oA}$, but not $G_{oB}$. If PS-1 without its C-terminal "tail" (lane 4), which protrudes from the membrane into the aqueous intracellular compartment), is transfected into ES double null cells along with $G_{oA}$ (lane 6), little or no $G_{oA}$ is immunoprecipitated along with the PS-1 tailless, showing that the C-terminal domain of PS-1 is the principal region of $G_{oA}$ binding to PS-1.

As used herein, the singular forms "a," "and," and "the" include plural referents unless the context clearly dictates otherwise. Thus, for example, reference to "a protein" includes a plurality of such proteins and reference to "the cell" includes reference to one or more cells known to those skilled in the art, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

The publications discussed above and throughout the text are provided solely for their disclosure prior to the filing date of the present application. Nothing herein is to be construed as an admission that the inventors are not entitled to antedate such disclosure by virtue of prior disclosure.

The disclosure provides methods and compositions useful for treating Alzheimer's Disease and disorders as well as neuronal development and activity modulated by the interaction of a Presenilin with β-APP. The disclosure demonstrates that interaction of Presenilin-1 and/or -2 with β-APP results in the generation of Aβ. Furthermore that Presenilins activate G-proteins upon binding β-APP.

The disclosure demonstrates that the β-amyloid precursor protein, β-APP, and PS-1 or -2 are components of an intercellular signaling system. One or more forms of β-APP can specifically bind either to PS-1, or PS-2, via their extracellular domains that protrude from their respective cell membranes. This binding in vivo induces an intercellular signaling event of significance to normal neural physiology or development. A by-product of this transcellular molecular binding, processes of vesicle formation, cellular internalization, and proteolytic degradation are set in motion that result in the formation and cellular release of Aβ and its slow accumulation in regions of the brain.

The disclosure demonstrates that PS-1, PS-2 and β-APP play a role in intracellular signaling. These three proteins have been examined for their respective roles in the proteolytic fragmentation of β-APP to Aβ that involves the PS proteins either directly or indirectly. In addition, one or more forms of β-APP on one cell surface and PS-1 (or PS-2) on another may be specific ligand and receptor components of an intercellular signaling system with a role in normal physiology. The disclosure provides evidence that intercellular surface binding of β-APP to the PS proteins functions in normal physiology to induce a signaling process within one, or both, of the adherent cells, leading ultimately to a developmental outcome significant for the organism.

The term "amyloid beta peptide" means amyloid beta peptides processed from the amyloid beta precursor protein (APP). The most common peptides include amyloid beta peptides 1-40, 1-42, 11-40 and 11-42. Other less prevalent amyloid beta peptide species are described as x-42, whereby x ranges from 2-10 and 12-17, and 1-y whereby y ranges from 24-39 and 41. For descriptive and technical purposes, "x" has a value of 2 to 17, and "y" has a value of 24 to 41.

The presenilins have a number of domains that can be identified by one or more different predictive algorithms or by experimental proteolytic lysis experiments, solubility assays, and the like. Presenilin-1 (PS-1) has a number of domains as set forth below. It will be recognized that the domains may vary from 1 to 5 amino acids at either end depending upon the organism that expresses the polypeptide. In one embodiment, a PS-1 N-terminal domain comprises residues x1 to about x2 of SEQ ID NO:2, wherein x1 comprises amino acid 1, 2, 3, 4 or 5 and x2 comprises amino acid 79, 80, 81, 82 or 83 of SEQ ID NO:2. In one embodiment, an N-terminal domain fragment comprises a peptide of between 5 and 81 amino acids in length (e.g., 5, 10, 20, 30, 40, 50, 60, 70 or 80 amino acids in length). Such peptide fragments (e.g., soluble fragments) are useful as βAPP binding agents or for the development of antibodies specific to an N-terminal extracellular domain of presenilin-1. The N-terminal domain may further comprise all or a fragment of the first transmembrane domain (TM-1) comprising amino acids 82-100. In one embodiment, the TM-1 domain comprises amino acid x2 to about amino acid x3 of SEQ ID NO:2, wherein x2 comprises amino acid 79, 80, 81, 82, or 83 of SEQ ID NO:2 and x3 comprises amino acid 98, 99, 100, 101 or 102 of SEQ ID NO:2. An N-terminal fragment of presenilin 1 further comprising a fragment of the first TM domain of presenilin-1 can be used to produce a membrane bound competitive inhibitor, which lacks an active G-protein domain.

The first cytoplasmic loop 1 of presenilin-1 comprises amino acid x3 to about x4 of SEQ ID NO:2, wherein x3 comprises amino acid 98, 99, 100, 101, or 102 of SEQ ID NO:2 and x4 comprises amino acid 130, 131, 132, 133 or 134. The second transmembrane loop of presenilin-1 (TM-2) comprises amino acids x4 to about x5 of SEQ ID NO:2, wherein x4 comprises amino acid 130, 131, 132, 133 or 134 of SEQ ID NO:2 and x5 comprises amino acid 152, 153, 154, 155 or 156 of SEQ ID NO:2. The presenilin-1 polypeptide further comprises a second extracellular domain (exoplasmic 1) comprises amino acids x5 to about x6 of SEQ ID NO:2, wherein x5 comprises amino acid 152, 153, 154, 155 or 156 of SEQ ID NO:2 and x6 comprises amino acid 161, 162, 163, 164, or 165 of SEQ ID NO:2. Presenilin-1 further includes a third transmembrane domain (TM-3) comprising amino acids x6 to about x7 of SEQ ID NO:2, wherein x6 comprises amino acid 161, 162, 163, 164 or 165 of SEQ ID NO:2 and x7 comprises amino acid 182, 183, 184, 185, or 186. Presenilin-1 comprises a second cytoplasmic loop (loop 3/cytoplasmic loop 2) comprising amino acids x7 to about x8 of SEQ ID NO:2, wherein x7 comprises amino acid 182, 183, 184, 185 or 186 of SEQ ID NO:2 and x8 comprises amino acid 192, 193, 194, 195 or 196 of SEQ ID NO:2. A fourth transmembrane domain (TM-4) of presenilin-1 can be generally described as comprising amino acids x8 to about x9 of SEQ ID NO:2, wherein x8 comprises amino acid 192, 193, 194, 195 or 196 of SEQ ID NO:2 and x9 comprises amino acid 211, 212, 213, 214 or 215 of SEQ ID NO:2. Presenilin-1 includes a third extracellular domain (Loop4/exoplasmic loop 2) comprising from about x9 to about x10 of SEQ ID NO:2, wherein x9 comprises amino acid 211, 212, 213, 214 or 215 of SEQ ID NO:2 and x10 comprises amino acid 217, 218, 219, 220 or 221 of SEQ ID NO:2. A fifth transmembrane domain (TM-5) of presenilin-1 can be generally described as comprising amino acids x10 to about x11 of SEQ ID NO:2, wherein x10 comprises amino acid 217, 218, 219, 220 or 221 of SEQ ID NO:2 and x11 comprises amino acid 236, 237, 238, 239 or 240 of SEQ ID NO:2. Presenilin-1 further includes a third cytoplasmic domain (loop5/cytoplasmic 3) comprising amino acids x11 to x12 of SEQ ID NO:2, wherein x11 comprises amino acid 236, 237, 238, 239 or 240 of SEQ ID NO:2 and x12 comprises amino acid 241, 242, 243, 244 or 245 of SEQ ID NO:2. A sixth transmembrane domain (TM-6) is generally referred to by the sequence comprising x12 to about x13 of SEQ ID NO:2, wherein x12 comprises amino acid 241, 242, 243, 244 or 245 of SEQ ID NO:2 and x13 comprises amino acid 260, 261, 262, 263 or 264 of SEQ ID NO:2. Presenilin-1 further includes a third cytoplasmic domain (loop 6/exoplasmic 3) comprising a sequence x13 to about x14 of SEQ ID NO:2, wherein x13 comprises amino acid 260, 261, 262, 263 or 264 of SEQ ID NO:2 and x14 comprises amino acid 405, 406, 407, 408 or 409 of SEQ ID NO:2. Presenilin-1 further includes a seventh transmembrane domain (TM-7) comprising a sequence x14 to about x15 of SEQ ID NO:2, wherein x14 comprises amino acid 405, 406, 407, 408 or 409 of SEQ ID NO:2 and x15 comprises amino acid 427, 428, 429, 430 or 431 of SEQ ID NO:2. The C-terminal cytoplasmic tail (C-tail/cytoplasmic) includes a sequence x15 to about x16 of SEQ ID NO:2, wherein x15 comprises amino acid 427, 428, 429, 430 or 431 of SEQ ID NO:2 and x16 comprises amino acid 462, 463, 464, 465, 466 or 467 of SEQ ID NO:2.

| PS-1 | | |
|---|---|---|
| Domain | Residue Numbers* | Sequence |
| NH2 | 1-81 | MTELPAPLSYFQNAQMSEDNHLSNTVR SQNDNRERQEHNDRESLGHPEPLSNGRP QGNSRQVVEQDEEEDEELTLKYGAKH |
| TM-1 | 82-100 | VIMLFVPVTLCMVVVVATI |
| Loop 1 (Cytoplasmic 1) | 101-132 | KSVSFYTRKDGQLIYTPFTEDTETVGQRALHS |
| TM-2 | 133-154 | ILNAAIMISVIVVMTILLVVLY |
| Loop 2 (Exoplasmic 1) | 155-163 | KYRCYKVIH |
| TM-3 | 164-184 | AWLIISSLLLLFFFSFIYLGE |
| Loop 3 (Cytoplasmic 2) | 185-194 | VFKTYNVAVD |
| TM-4 | 195-213 | YITVALLIWNFGVVGMISI |
| Loop 4 (Exoplasmic 2) | 214-219 | HWKGPL |
| TM-5 | 220-238 | RLQQAYLIMISALMALVFI |
| Loop 5 (Cytoplasmic 3) | 239-243 | KYLPE |
| TM-6 | 244-262 | WTAWLILAVISVYDLVAVL |

PS-1 (continued)

| Domain | Residue Numbers* | Sequence |
|---|---|---|
| Loop 6 (Exoplasmic 3) | 263-407 | CPKGPLRMLVETAQERNETLFPALIYSS TMVWLVNMAEGDPEAQRRVSKNSKYN AESTERESQDTVAENDDGGFSEEWEAQR DSHLGPHRSTPESRAAVQELSSSILAGEDP EERGVKLGLGDFIFYSVLVGKASATASGDWNTT |
| TM-7 | 408-429 | IACFVAILIGLCLTLLLLAIF |
| C- Tail (Cytoplasmic) | 430-467 | KKALPALPISITFGLVFYFATDYLVQPFMDQ |

*Refer to SEQ ID NO: 2

Presenilin-2 (PS-2) has a number of domains as set forth below. It will be recognized that the domains may vary from 1 to 5 amino acids at either end depending upon the organism that expresses the polypeptide. In one embodiment, a PS-2 N-terminal domain comprises residues x1 to about x2 of SEQ ID NO:4, wherein x1 comprises amino acid 1, 2, 3, 4 or 5 and x2 comprises amino acid 85, 86, 87, 88 or 90 of SEQ ID NO:4. In one embodiment, an N-terminal domain fragment comprises a peptide of between 5 and 87 amino acids in length (e.g., 5, 10, 20, 30, 40, 50, 60, 70 or 80 amino acids in length). Such peptide fragments (e.g., soluble fragments) are useful as βAPP binding agents or for the development of antibodies specific to an N-terminal extracellular domain of presenilin-2. The N-terminal domain may further comprise all or a fragment of the first transmembrane domain (TM-1) comprising amino acids 87-106. In one embodiment, the TM-1 domain comprises amino acid x2 to about amino acid x3 of SEQ ID NO:4, wherein x2 comprises amino acid 85, 86, 87, 88 or 90 of SEQ ID NO:4 and x3 comprises amino acid 104, 105, 106, 107 or 108 of SEQ ID NO:4. An N-terminal fragment of presenilin 1 further comprising a fragment of the first TM domain of presenilin-2 can be used to produce a membrane bound competitive inhibitor, which lacks an active G-protein domain.

The first cytoplasmic loop 1 of presenilin-2 comprises amino acid x3 to about x4 of SEQ ID NO:4, wherein x3 comprises amino acid 104, 105, 106, 107 or 108 of SEQ ID NO:4 and x4 comprises amino acid 136, 137, 138, 139 or 140 of SEQ ID NO:4. The second transmembrane loop of presenilin-2 (TM-2) comprises amino acids x4 to about x5 of SEQ ID NO:4, wherein x4 comprises amino acid 136, 137, 138, 139 or 140 of SEQ ID NO:4 and x5 comprises amino acid 158, 159, 160, 161 or 162 of SEQ ID NO:4. The presenilin-2 polypeptide further comprises a second extracellular domain (exoplasmic 1) comprises amino acids x5 to about x6 of SEQ ID NO:4, wherein x5 comprises amino acid 158, 159, 160, 161 or 162 of SEQ ID NO:4 and x6 comprises amino acid 167, 168, 169, 170 or 171 of SEQ ID NO:4. Presenilin-2 further includes a third transmembrane domain (TM-3) comprising amino acids x6 to about x7 of SEQ ID NO:4, wherein x6 comprises amino acid 167, 168, 169, 170 or 171 of SEQ ID NO:4 and x7 comprises amino acid 187, 188, 189, 190 or 191 of SEQ ID NO:4. Presenilin-2 comprises a second cytoplasmic loop (loop 3/cytoplasmic loop 2) comprising amino acids x7 to about x8 of SEQ ID NO:4, wherein x7 comprises amino acid 187, 188, 189, 190 or 191 of SEQ ID NO:4 and x8 comprises amino acid 198, 199, 200, 201 or 202 of SEQ ID NO:4. A fourth transmembrane domain (TM-4) of presenilin-2 can be generally described as comprising amino acids x8 to about x9 of SEQ ID NO:4, wherein x8 comprises amino acid 198, 199, 200, 201 or 202 of SEQ ID NO:4 and x9 comprises amino acid 217, 218, 219, 220 or 221 of SEQ ID NO:4. Presenilin-2 includes a third extracellular domain (Loop4/exoplasmic loop 2) comprising from about x9 to about x10 of SEQ ID NO:4, wherein x9 comprises amino acid 217, 218, 219, 220 or 221 of SEQ ID NO:4 and x10 comprises amino acid 223, 224, 225, 226 or 227 of SEQ ID NO:4. A fifth transmembrane domain (TM-5) of presenilin-2 can be generally described as comprising amino acids x10 to about x11 of SEQ ID NO:4, wherein x10 comprises amino acid 223, 224, 225, 226 or 227 of SEQ ID NO:4 and x11 comprises amino acid 242, 243, 244, 245 or 246 of SEQ ID NO:4. Presenilin-2 further includes a third cytoplasmic domain (loop5/cytoplasmic 3) comprising amino acids x11 to x12 of SEQ ID NO:4, wherein x11 comprises amino acid 242, 243, 244, 245 or 246 of SEQ ID NO:4 and x12 comprises amino acid 247, 248, 249, 250 or 251 of SEQ ID NO:4. A sixth transmembrane domain (TM-6) is generally referred to by the sequence comprising x12 to about x13 of SEQ ID NO:4, wherein x12 comprises amino acid 247, 248, 249, 250 or 251 of SEQ ID NO:4 and x13 comprises amino acid 266, 267, 268, 269 or 270 of SEQ ID NO:4. Presenilin-2 further includes a third cytoplasmic domain (loop 6/exoplasmic 3) comprising a sequence x13 to about x14 of SEQ ID NO:4, wherein x13 comprises amino acid 266, 267, 268, 269 or 270 of SEQ ID NO:4 and x14 comprises amino acid 385, 386, 387, 388 or 389 of SEQ ID NO:4. Presenilin-2 further includes a seventh transmembrane domain (TM-7) comprising a sequence x14 to about x15 of SEQ ID NO:4, wherein x14 comprises amino acid 385, 386, 387, 388 or 389 of SEQ ID NO:4 and x15 comprises amino acid 407, 408, 409, 410 or 411 of SEQ ID NO:4. The C-terminal cytoplasmic tail (C-tail/cytoplasmic) includes a sequence x15 to about x16 of SEQ ID NO:4, wherein x15 comprises amino acid 407, 408, 409, 410 or 411 of SEQ ID NO:4 and x16 comprises amino acid 443, 444, 445, 446, 447 or 448 of SEQ ID NO:4.

PS-2

| Domain | Residue Numbers* | Sequence |
|---|---|---|
| NH2 | 1-87 | MLTFMASDSEEEVCDERTSLMSAESPTPRS CQEGRQGPEDGENTAQWRSQENEEDGEED PDRYVCSGVPGRPPGLEEELTLKYGAKH |

PS-2

| Domain | Residue Numbers* | Sequence |
|---|---|---|
| TM-1 | 88-106 | VIMLFVPVTLCMIVVVATI |
| Loop 1 (Cytoplasmic 1) | 107-138 | KSVRFYTEKNGQLIYTTFTEDTPSVGQRLLNS |
| TM-2 | 139-160 | VLNTLIMISVIVVMTIFLVVLY |
| Loop 2 (Exoplasmic 1) | 161-169 | KYRCYKFIH |
| TM-3 | 170-189 | GWLIMSSLMLLFLFTYIYLG |
| Loop 3 (Cytoplasmic 2) | 190-200 | EVLKTYNVAMD |
| TM-4 | 201-219 | YPTLLLTVWNFGAVGMVCI |
| Loop 4 (Exoplasmic 2) | 220-225 | HWKGPL |
| TM-5 | 226-244 | VLQQAYLIMISALMALVFI |
| Loop 5 (Cytoplasmic 3) | 245-249 | KYLPE |
| TM-6 | 250-268 | WSAWVILGAISVYDLVAVL |
| Loop 6 (Exoplasmic 3) | 269-387 | CPKGPLRMLVETAQERNEPIF PALIYSSAMVWTVGMAKLDPSSQGALQLPYDPE MEEDSYDSFGEPSYPEVFEPPLTGYPGEELEEEEE RGVKLGLGDFIFYSVLVGKAAATGSGDWNT |
| TM-7 | 388-409 | TLACFVAILIGLCLTLLLLAVF |
| C- Tail (Cytoplasmic) | 410-448 | KKALPALPISITFGLIFYFSTDNL VRPFMDTLASHQLYI |

*Refer to SEQ ID NO: 4

The skilled artisan will recognize that the boundaries of these domain are approximate and that the precise boundaries of such domains, as for example the boundaries of the transmembrane domains, may differ in 1-5 amino acids from those predicted herein.

The most C-terminal residues of the cytoplasmic tail domains (along with other cytoplasmic domains) of Presenilin polypeptides are believed to be involved with interaction with G-proteins, such that substitutions of those residues are likely be associated with an altered G-protein activation or binding function, or with a lack of that function, for the polypeptide.

As used herein, "β-APP binding polypeptide or peptide" includes human Presenilin-1 (SEQ ID NO:2), variants (e.g., Presenilin-2; SEQ ID NO:4) and species homologues such as murine Presenilin-1 and fragments of these Presenilin polypeptides and their species homologues. Presenilin polypeptides of the disclosure have biological activities and functions that are consistent with those of the other Presenilin family polypeptides. Polypeptides of the Presenilin family are expressed in cell types including neuronal cells throughout development. Typical biological activities or functions associated with this family of polypeptides are β-APP binding, G-protein activation and Aβ peptide formation. β-APP binding activity is found on the N-terminal domain and the extracellular loops of the Presenilin polypeptide. G-protein activation is associated with the C-terminal cytoplasmic tail domain and other cytoplasmic domains of Presenilin polypeptides.

Presenilin polypeptides such as human Presenilin-1 have heterotypic binding activity; each of these binding activities is associated with the extracellular loop domains of Presenilin polypeptides. Thus, for uses requiring heterotypic binding Presenilin polypeptides of the disclosure will include those having at least one extracellular loop domain and exhibiting at least one such binding activity. Presenilin polypeptides also have G-Protein binding activity associated with the cytoplasmic domains (including the cytoplasmic tail domain) of Presenilin polypeptides. Thus, for uses requiring G-protein activation or binding Presenilin polypeptides of the disclosure will include those having a cytoplasmic tail domain and exhibiting G-protein binding activity. Presenilin polypeptides of the disclosure further include oligomers or fusion polypeptides comprising at least one extracellular loop domain and/or cytoplasmic tail domain of one or more Presenilin polypeptides of the disclosure, and fragments of any of these polypeptides that have heterotypic binding and/or G-protein domain binding activity. The binding activity or activities of human Presenilin-1 and species homologues and other Presenilin family polypeptides may be determined, for example, in a yeast two-hybrid assay, or in an in vitro assay that measures binding between a Presenilin polypeptide and one β-APP and/or G-protein domain-containing binding partners, where either the Presenilin polypeptide or its binding partner is labeled with a radioactive, fluorescent, or bioluminescent protein such that binding can be detected.

The term "human Presenilin polypeptide activity," as used herein, includes β-APP binding and interactions and G-protein binding or activation. The degree to which Presenilin polypeptides of the disclosure and fragments and other derivatives of these polypeptides exhibit these activities can be determined by standard assay methods. Exemplary assays are disclosed herein; those of skill in the art will appreciate that other, similar types of assays can be used to measure the biological activities of Presenilin polypeptides of the disclosure and other Presenilin family members.

One aspect of the biological activity of Presenilin polypeptides including human Presenilin-1 is the ability of members of this polypeptide family to bind particular binding partners such heterotypic polypeptides (including β-APP) and G-protein domain-containing polypeptides, with the extracellular loop domains binding, for example, to β-APP, and the cytoplasmic tail domain binding to G-protein domain-containing polypeptides. The term "binding partner," as used herein, includes ligands, receptors, substrates, antibodies, other Presenilin polypeptides, and any other molecule that interacts with a human Presenilin-1 polypeptide through contact or proximity between particular portions of the binding partner and the human Presenilin-1 or -2 polypeptide. Because the extracellular N-terminal and loop domains of Presenilin polypeptides of the disclosure bind to heterotypic polypeptides, a derivative polypeptide comprising f fragment of the N-terminal 80 amino acids and/or one or more extracellular loop domains when expressed as a separate fragment from the rest of a human Presenilin-1 polypeptide, or as a soluble polypeptide, fused for example to an immunoglobulin Fc domain, is expected to disrupt the binding of Presenilin polypeptides of the disclosure to its binding partners (e.g., β-APP). By binding to one or more binding partners, the separate extracellular domain(s) polypeptide prevents binding by the native human Presenilin-1 polypeptide(s), and so acts in a dominant negative fashion to inhibit the biological activities mediated via binding of Presenilin polypeptides of the disclosure heterotypic polypeptides (e.g., β-APP), thereby, in one aspect, preventing the formation of Aβ. The biological activities and partner-binding properties of human Presenilin-1 and other Presenilin family polypeptides may be assayed by standard methods and by those assays described herein.

As described herein, Presenilin-1 and -2 has been shown GPCRs related transmembrane proteins that, when activated cause production of Aβ peptides. Therefore, Presenilin-1 and -2 are involved in conditions and disorders Alzheimer's Disease development and disorders related thereto, including memory modification. Blocking or inhibiting the interactions between Presenilin polypeptides of the disclosure and their substrates, ligands, receptors, binding partners, and or other interacting polypeptides is an aspect of the disclosure and provides methods for treating or ameliorating these diseases and conditions through the use of inhibitors of human Presenilin-1 and -2 activity. Examples of such inhibitors or antagonists are described in more detail below.

In one embodiment, a Presenilin-1 or -2 polypeptide or polynucleotide plays a role normal memory and Alzheimer's Disease development and progression. In one embodiment, the methods and compositions of the disclosure include antagonists of Presenilin-1 or -2 activity comprising a peptide, peptidomimetic, small molecule or other agent the prevents the interaction of a Presenilin with β-App or activation of a G-protein.

A human Presenilin-1 polypeptide is a polypeptide that (a) has a sequence as set forth in SEQ ID NO:2; (b) shares a sufficient degree of amino acid identity or similarity to a Presenilin-1 polypeptide comprising an amino acid sequence as set forth in SEQ ID NO:2; (c) is identified by those of skill in the art as a polypeptide likely to share particular structural domains with a Presenilin-1 polypeptide of SEQ ID NO:2; (d) has biological activities in common with a Presenilin polypeptide; and/or (e) binds to antibodies that also specifically bind to a Presenilin-1 polypeptide having a sequence as set forth in SEQ ID NO:2. A human Presenilin-2 polypeptide is a polypeptide that (a) has a sequence as set forth in SEQ ID NO:4; (b) shares a sufficient degree of amino acid identity or similarity to a Presenilin-2 polypeptide comprising an amino acid sequence as set forth in SEQ ID NO:4; (c) is identified by those of skill in the art as a polypeptide likely to share particular structural domains with a Presenilin-2 polypeptide of SEQ ID NO:4; (d) has biological activities in common with a Presenilin polypeptide; and/or (e) binds to antibodies that also specifically bind to a Presenilin-2 polypeptide having a sequence as set forth in SEQ ID NO:4. Presenilin polypeptides of the disclosure may be isolated from naturally occurring sources, or be recombinantly produced such that a recombinant Presenilin polypeptide has the same structure as naturally occurring Presenilin polypeptides, or may be produced to have structures that differ from naturally occurring Presenilin polypeptides. Polypeptides derived from any human Presenilin-1 or -2 polypeptide by any type of alteration (for example, but not limited to, insertions, deletions, or substitutions of, for example, 1-10 or more amino acids; changes in the state of glycosylation of the polypeptide; refolding or isomerization to change its three-dimensional structure or self-association state; and changes to its association with other polypeptides or molecules) are also Presenilin polypeptides of the disclosure. Therefore, the polypeptides provided by the disclosure include polypeptides characterized by amino acid sequences similar to those of the Presenilin polypeptides of the disclosure described herein, but into which modifications are naturally provided or deliberately engineered. A polypeptide that shares biological activities in common with Presenilin polypeptides of the disclosure is a polypeptide having Presenilin-1 activity. Examples of biological activities exhibited by members of the Presenilin polypeptide family include, without limitation, β-APP and G-protein activation.

An isolated polypeptide or peptide refers to a molecule comprising a sequence of amino acids and which may have, in addition to said amino acid sequence, additional material covalently linked to either or both ends of the polypeptide or peptide, said additional material between 1-10, 10-20, 20-30 or 40-50 additional amino acids covalently linked to either end, each end, or both ends of polypeptide and which polypeptide is removed from its natural state or is recombinantly produced using molecular biology or peptide synthesis techniques.

The disclosure provides both full-length and mature forms of Presenilin polypeptides of the disclosure. Full-length polypeptides are those having the complete primary amino acid sequence of the polypeptide as initially translated. The amino acid sequences of full-length polypeptides can be obtained, for example, by translation of the complete open reading frame ("ORF") of a cDNA molecule. Several full-length polypeptides may be encoded by a single genetic locus if multiple mRNA forms are produced from that locus by alternative splicing or by the use of multiple translation initiation sites. The "mature form" of a polypeptide refers to a polypeptide that has undergone post-translational processing steps such as cleavage of the signal sequence or proteolytic cleavage to remove a prodomain. Multiple mature forms of a particular full-length polypeptide may be produced, for example by cleavage of the signal sequence at multiple sites, or by differential regulation of proteases that cleave the polypeptide. The mature form(s) of such polypeptide may be obtained by expression, in a suitable mammalian cell or other host cell, of a polynucleotide molecule that encodes the full-length polypeptide. The sequence of the mature form of the polypeptide may also be determinable from the amino acid sequence of the full-length form, through identification of signal sequences or protease cleavage sites. The Presenilin polypeptides of the disclosure also include those that result from post-transcriptional or post-translational processing events such as alternate mRNA processing which can yield a truncated but biologically active polypeptide, for example, a naturally occurring soluble form of the polypeptide. Also encompassed within the disclosure are variations attributable to proteolysis such as differences in the N- or C-termini upon expression in different types of host cells, due to proteolytic removal of one or more terminal amino acids from the polypeptide (generally from 1 to 5 terminal amino acids).

The disclosure further includes Presenilin polypeptides of the disclosure with or without associated native-pattern glycosylation. Polypeptides expressed in yeast or mammalian expression systems (e.g., COS-1 or CHO cells) can be similar to or significantly different from a native polypeptide in molecular weight and glycosylation pattern, depending upon the choice of expression system. Expression of polypeptides of the disclosure in bacterial expression systems, such as $E.$ $coli$, provides non-glycosylated molecules. Further, a given preparation can include multiple differentially glycosylated species of the polypeptide. Glycosyl groups can be removed through conventional methods, in particular those utilizing glycopeptidase. In general, glycosylated polypeptides of the disclosure can be incubated with a molar excess of glycopeptidase (Boehringer Mannheim).

Species homologues of Presenilin polypeptides of the disclosure (e.g., the Presenilin-1 human and murine forms) and of polynucleotides encoding them are encompassed by the disclosure. As used herein, a "species homologue" is a polypeptide or polynucleotide with a different species of origin from that of a given polypeptide or polynucleotide, but with significant sequence similarity to the given polypeptide or polynucleotide, as determined by those of skill in the art. Species homologues may be isolated and identified by making suitable probes or primers from polynucleotides encoding the amino acid sequences provided herein and screening a suitable nucleic acid source from the desired species. The disclosure also encompasses allelic variants of Presenilin polypeptides of the disclosure and polynucleotides encoding them; that is, naturally-occurring alternative forms of such polypeptides and polynucleotides in which differences in amino acid or nucleotide sequence are attributable to genetic polymorphism (allelic variation among individuals within a population).

Fragments of the Presenilin polypeptides of the disclosure may be in linear form or cyclized using known methods, for example, as described in H. U. Saragovi, et al., Bio/Technology 10, 773-778 (1992) and in R. S. McDowell, et al., J. Amer. Chem. Soc. 114 9245-9253 (1992), both of which are incorporated by reference herein. Polypeptides and polypeptide fragments of the disclosure, and polynucleotides encoding them, include polypeptides and polynucleotides with amino acid or nucleotide sequence lengths that are at least 25% (e.g., at least 50%, or at least 60%, or at least 70%, or at least 80%) of the length of a Presenilin-1 polypeptide and have at least 60% sequence identity (e.g., at least 70%, at least 75%, at least 80%, at least 85%, at least 90%, at least 95%, at least 97.5%, or at least 99%, or at least 99.5%) with a Presenilin-1 polypeptide or encoding polynucleotide, where sequence identity is determined by comparing the amino acid sequences of the polypeptides when aligned so as to maximize overlap and identity while minimizing sequence gaps. Also included in the disclosure are polypeptides and polypeptide fragments, and polynucleotides encoding them, that contain or encode a segment typically comprising at least 8, or at least 10, or at least 15, or at least 20, or at least 30, or at least 40 contiguous amino acids. Such polypeptides and polypeptide fragments may also contain a segment that shares at least 70% sequence identity (or at least 70%, at least 75%, at least 80%, at least 85%, at least 90%, at least 95%, at least 97.5%, at least 99%, or at least 99.5%) with any such segment of any of the Presenilin polypeptides of the disclosure, where sequence identity is determined by comparing the amino acid sequences of the polypeptides when aligned so as to maximize overlap and identity while minimizing sequence gaps. The percent identity can be determined by visual inspection and mathematical calculation. Alternatively, the percent identity of two amino acid or two polynucleotide sequences can be determined by comparing sequence information using the GAP computer program, version 6.0 described by Devereux et al. (Nucl. Acids Res. 12:387, 1984) and available from the University of Wisconsin Genetics Computer Group (UWGCG). The typical default parameters for the GAP program include: (1) a unary comparison matrix (containing a value of 1 for identities and 0 for non-identities) for nucleotides, and the weighted comparison matrix of Gribskov and Burgess, Nucl. Acids Res. 14:6745, 1986, as described by Schwartz and Dayhoff, eds., Atlas of Polypeptide Sequence and Structure, National Biomedical Research Foundation, pp. 353-358, 1979; (2) a penalty of 3.0 for each gap and an additional 0.10 penalty for each symbol in each gap; and (3) no penalty for end gaps. Other programs used by those skilled in the art of sequence comparison may also be used, such as, for example, the BLASTN program version 2.0.9, available for use via the National Library of Medicine website ncbi.nlm.nih.gov/gorf/wblast2.cgi, or the UW-BLAST 2.0 algorithm. Standard default parameter settings for UW-BLAST 2.0 are described at the following Internet webpage: blast.wustl.edu/blast/README.html#References. In addition, the BLAST algorithm uses the BLOSUM64 amino acid scoring matrix, and optional parameters that may be used are as follows: (A) inclusion of a filter to mask segments of the query sequence that have low compositional complexity (as determined by the SEG program of Wootton & Federhen (Computers and Chemistry, 1993); also see Wootton J C and Federhen S, 1996, Analysis of compositionally biased regions in sequence databases, Methods Enzymol. 266: 554-71) or segments consisting of short-periodicity internal repeats (as determined by the XNU program of Clayerie & States (Computers and Chemistry, 1993)), and (B) a statistical significance threshold for reporting matches against database sequences, or E-score (the expected probability of matches being found merely by chance, according to the stochastic model of Karlin and Altschul (1990); if the statistical significance ascribed to a match is greater than this E-score threshold, the match will not be reported.); typical E-score threshold values are 0.5, or 0.25, 0.1, 0.05, 0.01, 0.001, 0.0001, 1e-5, 1e-10, 1e-15, 1e-20, 1e-25, 1e-30, 1e-40, 1e-50, 1e-75, or 1e-100.

The disclosure also provides for soluble forms of Presenilin polypeptides of the disclosure comprising certain fragments or domains of these polypeptides, and particularly those comprising the extracellular domain or one or more fragments of the extracellular domain. Soluble polypeptides are polypeptides that are capable of being secreted from the cells in which they are expressed. In such forms part or all of the intracellular and transmembrane domains of the polypeptide are deleted such that the polypeptide is fully secreted from the cell in which it is expressed. The intracellular and transmembrane domains of polypeptides of the disclosure can be identified in accordance with known techniques for determination of such domains from sequence information. Soluble Presenilin polypeptides of the disclosure also include those polypeptides which include part of the transmembrane region, provided that the soluble Presenilin-1 polypeptide is capable of being secreted from a cell, and which typically retains a human Presenilin-1 activity (e.g., such as the ability to bind to or interact with a β-APP. Soluble Presenilin polypeptides of the disclosure further include oligomers or fusion polypeptides comprising the extracellular portion of at least one Presenilin-1 or -2 polypeptide, and fragments that have Presenilin-1 or -2 activity. A secreted soluble polypeptide may be identified (and distinguished from its non-soluble membrane-bound counterparts) by separating intact cells which express the desired polypeptide from the culture medium, e.g., by centrifugation, and assaying the medium (supernatant) for the presence of the desired polypeptide. The presence of the desired polypeptide in the medium indicates that the polypeptide was secreted from the cells and thus is a soluble form of the polypeptide. Purification of the polypeptides from recombinant host cells is facilitated, since the soluble polypeptides are secreted from the cells. Moreover, soluble polypeptides are generally more suitable than membrane-bound forms for parenteral administration and for many enzymatic procedures.

In another aspect of the disclosure, polypeptides comprise various combinations of Presenilin-1 polypeptide domains, such as the cytoplasmic tail domain and the extracellular loop domain or a cytoplasmic tail and a cytoplasmic loop domain. Accordingly, polypeptides of the disclosure and polynucleotides encoding them include those comprising or encoding two or more copies of a domain such as the cytoplasmic tail domain, two or more copies of a domain such as the extracellular loop domain, or at least one copy of each domain, and these domains may be presented in any order within such polypeptides.

Further modifications in the peptide or DNA sequences can be made by those skilled in the art using known techniques. Modifications of interest in the polypeptide sequences may include the alteration, substitution, replacement, insertion or deletion of a selected amino acid. For example, one or more of the cysteine residues may be deleted or replaced with another amino acid to alter the conformation of the molecule, an alteration which may involve preventing formation of incorrect intramolecular disulfide bridges upon folding or renaturation. Techniques for such alteration, substitution, replacement, insertion or deletion are well known to those skilled in the art (see, e.g., U.S. Pat. No. 4,518,584). As another example, N-glycosylation sites in the polypeptide extracellular domain can be modified to preclude glycosylation, allowing expression of a reduced carbohydrate analog in mammalian and yeast expression systems. N-glycosylation sites in eukaryotic polypeptides are characterized by an amino acid triplet Asn-X—Y, wherein X is any amino acid except Pro and Y is Ser or Thr. Appropriate substitutions, additions, or deletions to the nucleotide sequence encoding these triplets will result in prevention of attachment of carbohydrate residues at the Asn side chain. Alteration of a single nucleotide, chosen so that Asn is replaced by a different amino acid, for example, is sufficient to inactivate an N-glycosylation site. Alternatively, the Ser or Thr can be replaced with another amino acid, such as Ala. Known procedures for inactivating N-glycosylation sites in polypeptides include those described in U.S. Pat. No. 5,071,972 and EP 276,846, hereby incorporated by reference. Additional variants within the scope of the disclosure include polypeptides that can be modified to create derivatives thereof by forming covalent or aggregative conjugates with other chemical moieties, such as glycosyl groups, lipids, phosphate, acetyl groups and the like. Covalent derivatives can be prepared by linking the chemical moieties to functional groups on amino acid side chains or at the N-terminus or C-terminus of a polypeptide. Conjugates comprising diagnostic (detectable) or therapeutic agents attached thereto are contemplated herein. Preferably, such alteration, substitution, replacement, insertion or deletion retains the desired activity of the polypeptide or a substantial equivalent thereof. One example is a variant that binds with essentially the same binding affinity as does the native form. Binding affinity can be measured by conventional procedures, e.g., as described in U.S. Pat. No. 5,512,457 and as set forth herein.

Other derivatives include covalent or aggregative conjugates of the polypeptides with other polypeptides or polypeptides, such as by synthesis in recombinant culture as N-terminal or C-terminal fusions. Examples of fusion polypeptides are discussed below in connection with oligomers. Further, fusion polypeptides can comprise peptides added to facilitate purification and identification. Such peptides include, for example, poly-His or the antigenic identification peptides described in U.S. Pat. No. 5,011,912 and in Hopp et al., Bio/Technology 6:1204, 1988. One such peptide is the FLAG® peptide, which is highly antigenic and provides an epitope reversibly bound by a specific monoclonal antibody, enabling rapid assay and facile purification of expressed recombinant polypeptide. A murine hybridoma designated 4E11 produces a monoclonal antibody that binds the FLAG® peptide in the presence of certain divalent metal cations, as described in U.S. Pat. No. 5,011,912, hereby incorporated by reference. The 4E11 hybridoma cell line has been deposited with the American Type Culture Collection under accession no. HB 9259. Monoclonal antibodies that bind the FLAG® peptide are available from Eastman Kodak Co., Scientific Imaging Systems Division, New Haven, Conn.

Encompassed by the disclosure are oligomers or fusion polypeptides that contain a Presenilin-1 or -2 polypeptide, one or more fragments of Presenilin polypeptides of the disclosure, or any of the derivative or variant forms of Presenilin polypeptides of the disclosure as disclosed herein. In particular embodiments, the oligomers comprise soluble Presenilin polypeptides of the disclosure. Oligomers can be in the form of covalently linked or non-covalently-linked multimers, including dimers, trimers, or higher oligomers. In one aspect of the disclosure, the oligomers maintain the binding ability of the polypeptide components and provide therefor, bivalent, trivalent, etc., binding sites. In an alternative embodiment the disclosure is directed to oligomers comprising multiple Presenilin polypeptides of the disclosure joined via covalent or non-covalent interactions between peptide moieties fused to the polypeptides, such peptides having the property of promoting oligomerization. Leucine zippers and certain polypeptides derived from antibodies are among the peptides that can promote oligomerization of the polypeptides attached thereto, as described in more detail below.

In embodiments where variants of the Presenilin polypeptides of the disclosure are constructed to include a membrane-spanning domain, they will form a membrane-spanning polypeptide. Membrane-spanning Presenilin polypeptides of the disclosure can be fused with extracellular domains of receptor polypeptides for which the ligand is known. Such fusion polypeptides can then be manipulated to control the intracellular signaling pathways triggered by the membrane-spanning Presenilin-1 polypeptide. Presenilin polypeptides of the disclosure that span the cell membrane can also be fused with agonists or antagonists of cell-surface receptors, or cellular adhesion molecules to further modulate Presenilin-1 intracellular effects. In another aspect of the disclosure, interleukins can be situated between Presenilin-1 polypeptide fragment and other fusion polypeptide domains.

Immunoglobulin-based Oligomers. The polypeptides of the disclosure or fragments thereof may be fused to molecules such as immunoglobulins for many purposes, including increasing the valency of polypeptide binding sites. For example, fragments of a Presenilin-1 or -2 polypeptide may be (a) fused directly or through a linker peptide to the Fc portion of an immunoglobulin, or (b) fused directly or through a linker peptide to another Presenilin-1 polypeptide. For a bivalent form of the polypeptide, such a fusion could be to the Fc portion of an IgG molecule. Other immunoglobulin isotypes may also be used to generate such fusions. For example, a polypeptide-IgM fusion would generate a decavalent form of the polypeptide of the disclosure. The term "Fc polypeptide" as used herein includes native and mutein forms of polypeptides made up of the Fc region of an antibody comprising any or all of the CH domains of the Fc region. Truncated forms of such polypeptides containing the hinge region that promotes dimerization are also included. Useful Fc polypeptides comprise an Fc polypeptide derived from a human IgG1 antibody. As one alternative, an oligomer is prepared using polypeptides derived from immunoglobulins. Preparation of fusion polypeptides comprising certain heterologous polypeptides fused to various portions of antibody-derived polypeptides (including the Fc domain) has been described, e.g., by Ashkenazi et al. (PNAS USA 88:10535, 1991); Byrn et al. (Nature 344:677, 1990); and Hollenbaugh and Aruffo ("Construction of Immunoglobulin Fusion Polypeptides", in Current Protocols in Immunology, Suppl. 4, pages 10.19.1-10.19.11, 1992). Methods for preparation and use of immunoglobulin-based oligomers are well known in the art. One embodiment of the disclosure is directed to a dimer comprising two fusion polypeptides created by fusing a polypeptide of the disclosure to an Fc polypeptide derived from an antibody. A gene fusion encoding the polypeptide/Fc fusion polypeptide is inserted into an appropriate expression vector. Polypeptide/Fc fusion polypeptides are expressed in host cells transformed with the recombinant expression vector, and allowed to assemble much like antibody molecules, whereupon interchain disulfide bonds form between the Fc moieties to yield divalent molecules. One suitable Fc polypeptide, described in PCT application WO 93/10151 (hereby incorporated by reference), is a single chain polypeptide extending from the N-terminal hinge region to the native C-terminus of the Fc region of a human IgG1 antibody. Another useful Fc polypeptide is the Fc mutein described in U.S. Pat. No. 5,457,035 and in Baum et al., (EMBO J. 13:3992-4001, 1994) incorporated herein by reference. The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors. The above-described fusion polypeptides comprising Fc moieties (and oligomers formed therefrom) offer the advantage of facile purification by affinity chromatography over Polypeptide A or Polypeptide G columns. In other embodiments, the polypeptides of the disclosure can be substituted for the variable portion of an antibody heavy or light chain. If fusion polypeptides are made with both heavy and light chains of an antibody, it is possible to form an oligomer with as many as four Presenilin-1 extracellular regions.

Alternatively, the oligomer is a fusion polypeptide comprising multiple Presenilin polypeptides of the disclosure, with or without peptide linkers (spacer peptides). Among the suitable peptide linkers are those described in U.S. Pat. Nos. 4,751,180 and 4,935,233, which are hereby incorporated by reference. An oligonucleotide sequence encoding a desired peptide linker can be inserted between, and in the same reading frame as a Presenilin polynucleotide of the disclosure, using any suitable conventional technique. For example, a chemically synthesized oligonucleotide encoding a peptide linker can be ligated between the sequences. In particular embodiments, a fusion polypeptide comprises from two to four soluble Presenilin polypeptides of the disclosure, separated by peptide linkers. Suitable peptide linkers, their combination with other polypeptides, and their use are well known by those skilled in the art Another method for preparing the oligomers of the disclosure involves use of a leucine zipper. Leucine zipper domains are peptides that promote oligomerization of the polypeptides in which they are found. Leucine zippers were originally identified in several DNA-binding polypeptides (Landschulz et al., Science 240:1759, 1988), and have since been found in a variety of different polypeptides. Among the known leucine zippers are naturally occurring peptides and derivatives thereof that dimerize or trimerize. The zipper domain (also referred to herein as an oligomerizing, or oligomer-forming, domain) comprises a repetitive heptad repeat, often with four or five leucine residues interspersed with other amino acids. Use of leucine zippers and preparation of oligomers using leucine zippers are well known in the art.

Other fragments and derivatives of the sequences of polypeptides which would be expected to retain polypeptide activity in whole or in part and may thus be useful for screening or other immunological methodologies may also be made by those skilled in the art given the disclosures herein. Such modifications are encompassed by the disclosure.

The disclosure provides soluble peptide fragments useful for treating AD by binding to β-APP and preventing β-APP interaction with the full length native Presenilin-1 or -2. Useful fragments include, but are not limited to: (i) a sequence consisting of N-DEEEDEEL-COOH (SEQ ID NO:5), (ii) a sequence consisting of SEQ ID NO:5 further including 1-50 additional amino acids at either the N- or C-terminal end so long as the peptide is capable of binding to a β-APP, (iii) the sequence N-RRSLGHPEPLSNGRP-COOH (SEQ ID NO:6), (iv) a sequence consisting of SEQ ID NO:6 further including 1-5 conservative amino acid substitutions, (v) a sequence consisting of (iii) or (iv) further including 1-50 additional amino acids at the N- or C-terminus, (vi) the sequence N-RRSLGHPEPLSNGRPQGN-SRQVVEQDEEEDEELTLKYGAK-COOH (SEQ ID NO:7), (vii) a sequence consisting of SEQ ID NO:7 further including 1-5 conservative amino acid substitutions, (viii) a sequence consisting of (vi) or (vii) further including 1-50 additional amino acids at the N- or C-terminus, and (ix) any of the foregoing comprising an unnatural amino acid or D-amino acid so long as the peptide are capable of interacting or binding to a β-APP. The disclosure demonstrates that PS-1 domains within the 80 amino-acid N-terminal fragment can specifically inhibit the production of Aβ when added to co-cultures of β-APP and PS-1 expressing cells. These peptides all inhibit Aβ production in 13-APP transgenic mice. The disclosure further demonstrates that if cell-cell interaction is inhibited, then both G-protein activation and Aβ production are also inhibited.

The disclosure also provides inhibitors of G-protein activation induced by interaction of β-APP and PS-1 or PS-2. For example, if the G-protein activation is inhibited (by the presence of PTx in the β-APP:PS-1 co-cultures), then Aβ production is also inhibited. Accordingly, the disclosure provides the sequence of the PS-1 intracellular domain required for G-protein activation and GoA binding. In one embodiment, the disclosure provides a C-terminal tail sequence comprising the first 20 amino acids of PS-1 (N—KKALPALPISITFGLV- FYFA-COOH; SEQ ID NO:8). In addition, the disclosure identifies intracellular loop 3 (KYLPE; SEQ ID NO:2 amino acids 239-243) of PS-1 (which has identity to the corresponding domain in PS-2) and peptides that binds $Go_4$ binding, including for example, N-MALVFIKYLPE-COOH; SEQ ID NO:9.

Encompassed within the disclosure are polynucleotides encoding such Presenilin polypeptides or peptides of the disclosure. These polynucleotides can be identified in several ways, including isolation of genomic or cDNA molecules from a suitable source. Nucleotide sequences corresponding to the amino acid sequences described herein, to be used as probes or primers for the isolation of polynucleotides or as query sequences for database searches, can be obtained by "back-translation" from the amino acid sequences, or by identification of regions of amino acid identity with polypeptides for which the coding DNA sequence has been identified. The well-known polymerase chain reaction (PCR) procedure can be employed to isolate and amplify a DNA sequence encoding a human Presenilin-1 or -2 polypeptide or a desired combination of human Presenilin-1 or -2 polypeptide fragments. Oligonucleotides that define the desired termini of the combination of DNA fragments are employed as 5' and 3' primers. The oligonucleotides can additionally contain recognition sites for restriction endonucleases, to facilitate insertion of the amplified combination of DNA fragments into an expression vector. PCR techniques are described in Saiki et al., Science 239:487 (1988); Recombinant DNA Methodology, Wu et al., eds., Academic Press, Inc., San Diego (1989), pp. 189-196; and PCR Protocols: A Guide to Methods and Applications, Innis et al., eds., Academic Press, Inc. (1990).

Polynucleotide molecules of the disclosure include DNA and RNA in both single-stranded and double-stranded form, as well as the corresponding complementary sequences. DNA includes, for example, cDNA, genomic DNA, chemically synthesized DNA, DNA amplified by PCR, and combinations thereof. The polynucleotide molecules of the disclosure include full-length genes or cDNA molecules as well as a combination of fragments thereof. The polynucleotides of the disclosure can be derived from human sources, but the disclosure includes those derived from non-human species, as well.

An "isolated polynucleotide" is a polynucleotide that has been separated from adjacent genetic sequences present in the genome of the organism from which the polynucleotide was isolated, in the case of polynucleotides isolated from naturally occurring sources. In the case of polynucleotides synthesized enzymatically from a template or chemically, such as PCR products, cDNA molecules, or oligonucleotides for example, it is understood that the polynucleotides resulting from such processes are isolated polynucleotides. An isolated polynucleotide refers to a polynucleotide in the form of a separate fragment or as a component of a larger polynucleotide construct. In one embodiment, the disclosure relates to certain isolated polynucleotides that are substantially free from contaminating endogenous material. The polynucleotide has preferably been derived from DNA or RNA isolated at least once in substantially pure form and in a quantity or concentration enabling identification, manipulation, and recovery of its component nucleotide sequences by standard biochemical methods (such as those outlined in Sambrook et al., Molecular Cloning. A Laboratory Manual, 2nd ed., Cold Spring Harbor Laboratory, Cold Spring Harbor, N.Y. (1989)). Such sequences are typically provided and/or constructed in the form of an open reading frame uninterrupted by internal non-translated sequences, or introns, that are typically present in eukaryotic genes. Sequences of non-translated DNA can be present 5' or 3' from an open reading frame, where the same do not interfere with manipulation or expression of the coding region.

Methods for making Presenilin polypeptides of the disclosure are described below. Expression, isolation, and purification of the polypeptides and fragments of the disclosure can be accomplished by any suitable technique, including but not limited to, the following methods. The isolated nucleic acid of the disclosure can be operably linked to an expression control sequence such as the pDC409 vector (Giri et al., 1990, EMBO J. 13: 2821) or the derivative pDC412 vector (Wiley et al., 1995, Immunity 3: 673). The pDC400 series vectors are useful for transient mammalian expression systems, such as CV-1 or 293 cells. Alternatively, the isolated nucleic acid of the disclosure can be linked to expression vectors such as pDC312, pDC316, or pDC317 vectors. The pDC300 series vectors all contain the SV40 origin of replication, the CMV promoter, the adenovirus tripartite leader, and the SV40 polyA and termination signals, and are useful for stable mammalian expression systems, such as CHO cells or their derivatives. Other expression control sequences and cloning technologies can also be used to produce the polypeptide recombinantly, such as the pMT2 or pED expression vectors (Kaufman et al., 1991, Nucleic Acids Res 19: 4485-4490; and Pouwels et al., 1985, Cloning Vectors. A Laboratory Manual, Elsevier, New York) and the GATEWAY Vectors (Life Technologies; Rockville, Md.). The isolated nucleic acid of the disclosure, flanked by attB sequences, can be recombined through an integrase reaction with a GATEWAY vector such as pDONR201 containing attP sequences, providing an entry vector for the GATEWAY system containing the isolated nucleic acid of the disclosure. This entry vector can be further recombined with other suitably prepared expression control sequences, such as those of the pDC400 and pDC300 series described above. Many suitable expression control sequences are known in the art. General methods of expressing recombinant polypeptides are also described in Kaufman, 1990, Methods in Enzymology 185, 537-566. As used herein "operably linked" means that a polynucleotide of the disclosure and an expression control sequence are situated within a construct, vector, or cell in such a way that a polypeptide encoded by a polynucleotide is expressed when appropriate molecules (such as polymerases) are present. As one embodiment of the disclosure, at least one expression control sequence is operably linked to a polynucleotide of the disclosure in a recombinant host cell or progeny thereof, the polynucleotide and/or expression control sequence having been introduced into the host cell by transformation or transfection, for example, or by any other suitable method. As another embodiment of the disclosure, at least one expression control sequence is integrated into the genome of a recombinant host cell such that it is operably linked to a polynucleotide sequence encoding a polypeptide of the disclosure. In a further embodiment of the disclosure, at least one expression control sequence is operably linked to a polynucleotide of the disclosure through the action of a trans-acting factor such as a transcription factor, either in vitro or in a recombinant host cell.

In addition, a sequence encoding an appropriate signal peptide (native or heterologous) can be incorporated into expression vectors. The choice of signal peptide or leader can depend on factors such as the type of host cells in which the recombinant polypeptide is to be produced. To illustrate, examples of heterologous signal peptides that are functional in mammalian host cells include the signal sequence for interleukin-7 (IL-7) described in U.S. Pat. No. 4,965,195; the signal sequence for interleukin-2 receptor described in Cosman et al., Nature 312:768 (1984); the interleukin-4 receptor signal peptide described in EP 367,566; the type I interleukin-1 receptor signal peptide described in U.S. Pat. No. 4,968,607; and the type II interleukin-1 receptor signal peptide described in EP 460,846. A DNA sequence for a signal peptide (secretory leader) can be fused in frame to a polynucleotide of the disclosure so that the DNA is initially transcribed, and the mRNA translated, into a fusion polypeptide comprising the signal peptide. A signal peptide that is functional in the intended host cells promotes extracellular secretion of the polypeptide. The signal peptide is cleaved from the polypeptide upon secretion of polypeptide from the cell. The skilled artisan will also recognize that the position(s) at which the signal peptide is cleaved can differ from that predicted by computer program, and can vary according to such factors as the type of host cells employed in expressing a recombinant polypeptide. A polypeptide preparation can include a mixture of polypeptide molecules having different N-terminal amino acids, resulting from cleavage of the signal peptide at more than one site.

Established methods for introducing DNA into mammalian cells have been described (Kaufman, 1990, Large Scale Mammalian Cell Culture, pp. 15-69). Additional protocols using commercially available reagents, such as Lipofectamine lipid reagent (Gibco/BRL) or Lipofectamine-Plus lipid reagent, can be used to transfect cells (Felgner et al., 1987, Proc. Natl. Acad. Sci. USA 84: 7413-7417). In addition, electroporation can be used to transfect mammalian cells using conventional procedures, such as those in Sambrook et al. (Molecular Cloning: A Laboratory Manual, 2 ed. Vol. 1-3, Cold Spring Harbor Laboratory Press, 1989). Selection of stable transformants can be performed using methods known in the art such as, for example, resistance to cytotoxic drugs. Kaufman et al., Meth. in Enzymology 185:487-511, 1990, describes several selection schemes, such as dihydrofolate reductase (DHFR) resistance. A suitable strain for DHFR selection can be CHO strain DX-B11, which is deficient in DHFR (Urlaub and Chasin, Proc. Natl. Acad. Sci. USA 77:4216-4220, 1980). A plasmid expressing the DHFR cDNA can be introduced into strain DX-B11, and only cells that contain the plasmid can grow in the appropriate selective media. Other examples of selectable markers that can be incorporated into an expression vector include cDNAs conferring resistance to antibiotics, such as G418 and hygromycin B. Cells harboring the vector can be selected on the basis of resistance to these compounds.

Alternatively, gene products can be obtained via homologous recombination, or "gene targeting," techniques. Such techniques employ the introduction of exogenous transcription control elements (such as the CMV promoter or the like) in a particular predetermined site on the genome, to induce expression of the endogenous polynucleotide sequence of interest. The location of integration into a host chromosome or genome can be easily determined by one of skill in the art, given the known location and sequence of the gene. In one embodiment, the disclosure also contemplates the introduction of exogenous transcriptional control elements in conjunction with an amplifiable gene, to produce increased amounts of the gene product, again, without the need for isolation of the gene itself from the host cell. The practice of homologous recombination or gene targeting is explained by Schimke, et al. "Amplification of Genes in Somatic Mammalian cells," Methods in Enzymology 151:85-104 (1987), as well as by Capecchi, et al., "The New Mouse Genetics. Altering the Genome by Gene Targeting," TIG 5:70-76 (1989).

A number of types of cells may act as suitable host cells for expression of a polypeptide. Mammalian host cells include, for example, the COS-7 line of monkey kidney cells (ATCC CRL 1651) (Gluzman et al., Cell 23:175, 1981), L cells, C127 cells, 3T3 cells (ATCC CCL 163), Chinese hamster ovary (CHO) cells, HeLa cells, BHK (ATCC CRL 10) cell lines, the CV1/EBNA cell line derived from the African green monkey kidney cell line CV1 (ATCC CCL 70) as described by McMahan et al. (EMBO J. 10: 2821, 1991), human kidney 293 cells, human epidermal A431 cells, human Colo205 cells, other transformed primate cell lines, normal diploid cells, cell strains derived from in vitro culture of primary tissue, primary explants, HL-60, U937, HaK or Jurkat cells. Alternatively, it may be possible to produce a polypeptide in lower eukaryotes such as yeast or in prokaryotes such as bacteria. Potentially suitable yeast strains include *Saccharomyces cerevisiae, Schizosaccharomyces pombe, Kluyveromyces strains, Candida*, or any yeast strain capable of expressing heterologous polypeptides. Potentially suitable bacterial strains include *Escherichia coli, Bacillus subtilis, Salmonella typhimurium*, or any bacterial strain capable of expressing heterologous polypeptides. If the polypeptide is made in yeast or bacteria, it may be necessary to modify the polypeptide produced therein, for example by phosphorylation or glycosylation of the appropriate sites, in order to obtain the functional polypeptide. Such covalent attachments may be accomplished using known chemical or enzymatic methods. The polypeptide may also be produced by operably linking an isolated polynucleotide of the disclosure to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBac® kit), and such methods are well known in the art, as described in Summers and Smith, Texas Agricultural Experiment Station Bulletin No. 1555 (1987), and Luckow and Summers, Bio/Technology 6:47 (1988), incorporated herein by reference. As used herein, an insect cell capable of expressing a polynucleotide of the disclosure is "transformed." Cell-free translation systems could also be employed to produce polypeptides using RNAs derived from polynucleotide constructs disclosed herein. A host cell that comprises an isolated polynucleotide of the disclosure, typically operably linked to at least one expression control sequence, is a "recombinant host cell".

A polypeptide or peptide of the disclosure may be prepared by culturing transformed host cells under culture conditions suitable to express the recombinant polypeptide. The resulting expressed polypeptide may then be purified from such culture (e.g., from culture medium or cell extracts) using known purification processes, such as gel filtration and ion exchange chromatography. The purification of a polypeptide may also include an affinity column containing agents which will bind to the polypeptide; one or more column steps over such affinity resins as concanavalin A-agarose, heparin-Toyopearl® or Cibacrom blue 3GA Sepharose®; one or more steps involving hydrophobic interaction chromatography using such resins as phenyl ether, butyl ether, or propyl ether; or immunoaffinity chromatography. Alternatively, a polypeptide of the disclosure may also be expressed in a form that will facilitate purification. For example, it may be expressed as a fusion polypeptide, such as those of maltose binding polypeptide (MBP), glutathione-S-transferase (GST) or thioredoxin (TRX). Kits for expression and purification of such fusion polypeptides are commercially available from New England BioLab (Beverly, Mass.), Pharmacia (Piscataway, N.J.) and InVitrogen, respectively. A polypeptide can also be tagged with an epitope and subsequently purified by using a specific antibody directed to such epitope. One such epitope ("Flag") is commercially available from Kodak (New Haven, Conn.).

Finally, one or more reverse-phase high performance liquid chromatography (RP-HPLC) steps employing hydrophobic RP-HPLC media, e.g., silica gel having pendant methyl or other aliphatic groups, can be employed to further purify the polypeptide. Some or all of the foregoing purification steps, in various combinations, can also be employed to provide a substantially homogeneous isolated recombinant polypeptide. A polypeptide thus purified is substantially free of other mammalian polypeptides and is defined in accordance with the disclosure as a "purified polypeptide"; such purified polypeptides of the disclosure include purified antibodies that bind to Presenilin polypeptides of the disclosure, fragments, variants, binding partner, and the like. A polypeptide of the disclosure may also be expressed as a product of transgenic animals, e.g., as a component of the milk of transgenic cows, goats, pigs, or sheep which are characterized by somatic or germ cells containing a polynucleotide encoding the polypeptide.

It is also possible to utilize an affinity column comprising a polypeptide-binding polypeptide of the disclosure, such as a monoclonal antibody generated against polypeptides of the disclosure, to affinity-purify expressed polypeptides. These polypeptides can be removed from an affinity column using conventional techniques, e.g., in a high salt elution buffer and then dialyzed into a lower salt buffer for use or by changing pH or other components depending on the affinity matrix utilized, or be competitively removed using the naturally occurring substrate of the affinity moiety, such as a polypeptide derived from the disclosure. In this aspect of the disclosure, polypeptide-binding polypeptides, such as the anti-polypeptide antibodies of the disclosure or other polypeptides that can interact with a polypeptide of the disclosure, can be bound to a solid phase support such as a column chromatography matrix or a similar substrate suitable for identifying, separating, or purifying cells that express polypeptides of the disclosure on their surface. Adherence of polypeptide-binding polypeptides of the disclosure to a solid phase contacting surface can be accomplished by any number of techniques, for example, magnetic microspheres can be coated with these polypeptide-binding polypeptides and held in the incubation vessel through a magnetic field. Suspensions of cell mixtures are contacted with the solid phase that has such polypeptide-binding polypeptides thereon. Cells having polypeptides of the disclosure on their surface bind to the fixed polypeptide-binding polypeptide and unbound cells then are washed away. This affinity-binding method is useful for purifying, screening, or separating such polypeptide-expressing cells from solution. Methods of releasing positively selected cells from the solid phase are known in the art and encompass, for example, the use of enzymes. Such enzymes are preferably non-toxic and non-injurious to the cells and are directed to cleaving the cell-surface binding partner. Alternatively, mixtures of cells suspected of containing polypeptide-expressing cells of the disclosure can first be incubated with a biotinylated polypeptide-binding polypeptide of the disclosure. Incubation periods are typically at least one hour in duration to ensure sufficient binding to polypeptides of the disclosure. The resulting mixture then is passed through a column packed with avidin-coated beads, whereby the high affinity of biotin for avidin provides the binding of the polypeptide-binding cells to the beads. Use of avidin-coated beads is known in the art (see, e.g., Berenson, et al. J. Cell. Biochem., 10D:239, 1986). Wash of unbound material and the release of the bound cells is performed using conventional methods A polypeptide may also be produced by known conventional chemical synthesis. Methods for constructing polypeptides of the disclosure by synthetic means are known to those skilled in the art. The synthetically constructed polypeptides, by virtue of sharing primary, secondary or tertiary structural and/or conformational characteristics with native polypeptides may possess biological properties in common therewith, including polypeptide activity. Thus, they may be employed as biologically active or immunological substitutes for natural, purified polypeptides in screening of therapeutic compounds and in immunological processes for the development of antibodies.

The desired degree of purity depends on the intended use of a polypeptide. A relatively high degree of purity is desired when a polypeptide is to be administered in vivo, for example. In such a case, polypeptides are purified such that no polypeptide bands corresponding to other polypeptides are detectable upon analysis by SDS-polyacrylamide gel electrophoresis (SDS-PAGE). It will be recognized by one skilled in the pertinent field that multiple bands corresponding to the polypeptide can be visualized by SDS-PAGE, due to differential glycosylation, differential post-translational processing, and the like. A polypeptide of the disclosure is purified to substantial homogeneity, as indicated by a single polypeptide band upon analysis by SDS-PAGE. The polypeptide band can be visualized by silver staining, Coomassie blue staining, or (if the polypeptide is radiolabeled) by autoradiography.

Any method that neutralizes Presenilin polypeptides of the disclosure or inhibits expression of a Presenilin-1 or -2 gene (either transcription or translation) or which inhibits the interaction of a Presenilin with β-APP can be used to modify memory and/or the onset or progression of Alzheimer's Disease. In particular embodiments, antagonists inhibit the binding of at least one Presenilin-1 polypeptide to binding partners expressed on cells, thereby inhibiting biological activities induced by the binding of those Presenilin polypeptides of the disclosure to the cells. In certain other embodiments of the disclosure, antagonists can be designed to reduce the level of endogenous Presenilin-1 or 2 gene expression, e.g., using well-known antisense or ribozyme approaches to inhibit or prevent translation of Presenilin-1 or -2 mRNA transcripts; triple helix approaches to inhibit transcription of Presenilin-1 genes; or targeted homologous recombination to inactivate or "knock out" a Presenilin-1 or -2 gene or their endogenous promoters or enhancer elements. Such antisense, ribozyme, and triple helix antagonists may be designed to reduce or inhibit either unimpaired, or if appropriate, mutant Presenilin-1 or -2 gene activity. Techniques for the production and use of such molecules are well known to those of skill in the art.

Antisense RNA and DNA molecules act to directly block the translation of mRNA by hybridizing to targeted mRNA and preventing polypeptide translation. Antisense approaches involve the design of oligonucleotides (either DNA or RNA) that are complementary to a Presenilin-1 mRNA. The antisense oligonucleotides will bind to the complementary target gene mRNA transcripts and prevent translation. Absolute complementarity, although preferred, is not required. A sequence "complementary" to a portion of a polynucleotide, as referred to herein, means a sequence having sufficient complementarity to be able to hybridize with the polynucleotide, forming a stable duplex (or triplex, as appropriate). In the case of double-stranded antisense nucleic acids, a single strand of the duplex DNA may thus be tested, or triplex formation may be assayed. The ability to hybridize will depend on both the degree of complementarity and the length of the antisense nucleic acid. Oligonucleotides that are complementary to the 5' end of the message, e.g., the 5' untranslated sequence up to and including the AUG initiation codon, should work most efficiently at inhibiting translation.

However, oligonucleotides complementary to either the 5'- or 3'-non-translated, non-coding regions of a Presenilin-1 or -2 gene transcript could be used in an antisense approach to inhibit translation of endogenous Presenilin-1 or -2 mRNA. Oligonucleotides complementary to the 5' untranslated region of the mRNA should include the complement of the AUG start codon. Antisense nucleic acids should be at least six nucleotides in length, and typically range from 6 to about 50 nucleotides in length. In specific aspects the oligonucleotide is at least 10 nucleotides, at least 17 nucleotides, at least 25 nucleotides or at least 50 nucleotides. The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, and the like. The oligonucleotide may include other appended groups such as peptides (e.g., for targeting host cell receptors in vivo), or agents facilitating transport across the cell membrane (see, e.g., Letsinger et al., 1989, Proc. Natl. Acad. Sci. U.S.A. 86:6553-6556; Lemaitre et al., 1987, Proc. Natl. Acad. Sci. 84:648-652; PCT Publication No. WO88/09810, published Dec. 15, 1988), or hybridization-triggered cleavage agents or intercalating agents (see, e.g., Zon, 1988, Pharm. Res. 5:539-549). The antisense molecules should be delivered to cells that express a human Presenilin-1 or -2 transcript in vivo. A number of methods have been developed for delivering antisense DNA or RNA to cells; e.g., antisense molecules can be injected directly into the tissue or cell derivation site, or modified antisense molecules, designed to target the desired cells (e.g., antisense linked to peptides or antibodies that specifically bind receptors or antigens expressed on the target cell surface) can be administered systemically. However, it is often difficult to achieve intracellular concentrations of the antisense molecule sufficient to suppress translation of endogenous mRNAs. Therefore one approach utilizes a recombinant DNA construct in which the antisense oligonucleotide is placed under the control of a strong pol III or pol II promoter. The use of such a construct to transfect target cells in a subject will result in the transcription of sufficient amounts of single stranded RNAs that will form complementary base pairs with the endogenous Presenilin-1 gene transcripts and thereby prevent translation of the Presenilin-1 or -2 mRNA. For example, a vector can be introduced in vivo such that it is taken up by a cell and directs the transcription of an antisense RNA. Such a vector can remain episomal or become chromosomally integrated, so long as it can be transcribed to produce the desired antisense RNA. Such vectors can be constructed by recombinant DNA technology methods standard in the art. Vectors can be plasmid, viral, or others known in the art used for replication and expression in mammalian cells.

Ribozyme molecules designed to catalytically cleave Presenilin-1 or -2 mRNA transcripts can also be used to prevent translation of Presenilin-1 or -2 mRNA thereby inhibiting expression of Presenilin polypeptides of the disclosure (see, e.g., PCT International Publication WO90/11364, published Oct. 4, 1990; U.S. Pat. No. 5,824,519). The ribozymes that can be used in the disclosure include hammerhead ribozymes (Haseloff and Gerlach, 1988, Nature, 334:585-591), RNA endoribonucleases (hereinafter "Cech-type ribozymes") such as the one which occurs naturally in Tetrahymena Thermophila (known as the IVS, or L-19 IVS RNA) and which has been extensively described by Thomas Cech and collaborators (International Patent Application No. WO 88/04300; Been and Cech, 1986, Cell, 47:207-216). As in the antisense approach, the ribozymes can be composed of modified oligonucleotides (e.g. for improved stability, targeting, and the like) and should be delivered to cells which express the human Presenilin-1 polypeptide in vivo. A typical method of delivery involves using a DNA construct coding for the ribozyme under the control of a strong constitutive pol II or pol III promoter, so that transfected cells will produce sufficient quantities of the ribozyme to destroy endogenous Presenilin-1 or -2 messages and inhibit translation. Because ribozymes, unlike antisense molecules, are catalytic, a lower intracellular concentration is required for efficiency.

Alternatively, endogenous Presenilin-1 or -2 gene expression can be reduced by targeting deoxyribonucleotide sequences complementary to the regulatory region of the target gene (e.g., the target gene's promoter and/or enhancers) to form triple helical structures that prevent transcription of a Presenilin-1 gene (see generally, Helene, 1991, Anticancer Drug Des., 6(6):569-584; Helene, et al., 1992, Ann. N.Y. Acad. Sci., 660, 27-36; and Maher, 1992, Bioassays 14(12):807-815).

Antisense nucleic acids, ribozyme, and triple helix molecules of the disclosure may be prepared by any method known in the art for the synthesis of DNA and RNA molecules. These include techniques for chemically synthesizing oligodeoxyribonucleotides and oligoribonucleotides well known in the art such as, for example, solid phase phosphoramidite chemical synthesis. Oligonucleotides can be synthesized by standard methods known in the art, e.g. by use of an automated DNA synthesizer (such as are commercially available from Biosearch, Applied Biosystems, and the like). As examples, phosphorothioate oligonucleotides may be synthesized by the method of Stein et al., 1988, Nucl. Acids Res. 16:3209. Methylphosphonate oligonucleotides can be prepared by use of controlled pore glass polymer supports (Sarin et al., 1988, Proc. Natl. Acad. Sci. U.S.A. 85:7448-7451). Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Organisms that have enhanced, reduced, or modified expression of the gene(s) corresponding to the polynucleotide sequences disclosed herein are provided. The desired change in gene expression can be achieved through the use of antisense nucleic acids or ribozymes that bind and/or cleave the mRNA transcribed from the gene (Albert and Morris, 1994, Trends Pharmacol. Sci. 15(7):250-254; Lavarosky et al., 1997, Biochem. Mol. Med. 62(1):11-22; and Hampel, 1998, Prog. Nucleic Acid Res. Mol. Biol. 58:1-39; all of which are incorporated by reference herein). Transgenic animals that have multiple copies of the gene(s) corresponding to the polynucleotide sequences disclosed herein, produced by transformation of cells with genetic constructs that are stably maintained within the transformed cells and their progeny, are provided. Transgenic animals that have modified genetic control regions that increase or reduce gene expression levels, or that change temporal or spatial patterns of gene expression, are also provided (see, e.g., European Patent No. 0 649 464 B1, incorporated by reference herein). In addition, organisms are provided in which the gene(s) corresponding to the polynucleotide sequences disclosed herein have been partially or completely inactivated, through insertion of extraneous sequences into the corresponding gene(s) or through deletion of all or part of the corresponding gene(s). Partial or complete gene inactivation can be accomplished through insertion, followed by imprecise excision, of transposable elements (Plasterk, 1992, Bioessays 14(9):629-633; Zwaal et al., 1993, Proc. Natl. Acad. Sci. USA 90(16):7431-7435; Clark et al., 1994, Proc. Natl. Acad. Sci. USA 91(2):719-722; all of which are incorporated by reference herein), or through homologous recombination which can be detected by positive/negative genetic selection strategies (Mansour et al., 1988, Nature 336:348-352; U.S. Pat. Nos. 5,464,764; 5,487,992; 5,627,059; 5,631,153; 5,614,396; 5,616,491; and 5,679,523; all of which are incorporated by reference herein). These organisms with altered gene expression are eukaryotes and typically are mammals. Such organisms are useful for the development of non-human models for the study of disorders involving the corresponding gene(s), and for the development of assay systems for the identification of molecules that interact with the polypeptide product(s) of the corresponding gene(s).

The Presenilin polypeptides of the disclosure themselves can also be employed in inhibiting a biological activity of Presenilin-1 or -2 in in vitro or in vivo procedures. Encompassed within the disclosure are extracellular loop domains of Presenilin polypeptides of the disclosure that act as "dominant negative" inhibitors of native Presenilin-1 or -2 polypeptide function when expressed as fragments or as components of fusion polypeptides. For example, a purified polypeptide domain of the disclosure can be used to inhibit binding of Presenilin polypeptides of the disclosure to endogenous binding partners. Such use would effectively block Presenilin-1 or -2 polypeptide interactions with β-APP and inhibit Presenilin-1 or -2 polypeptide activities. In still another aspect of the disclosure, a soluble form of a Presenilin-1 or -2 binding partner, which is expressed on epithelial and/or endothelial cells, is used to bind to and competitively inhibit activation of an endogenous Presenilin-1 or -2 polypeptide. Furthermore, antibodies which bind to Presenilin polypeptides of the disclosure can inhibit Presenilin-1 or -2 activity and act as antagonists, or as agonists. For example, antibodies that specifically recognize one or more epitopes of Presenilin polypeptides of the disclosure, or epitopes of conserved variants of Presenilin polypeptides of the disclosure, or peptide fragments of a Presenilin-1 polypeptide can be used in the disclosure to inhibit Presenilin-1 or -2 activity (e.g., antagonistic antibodies). Agonistic antibodies bind to Presenilin polypeptides of the disclosure or binding partners and increase Presenilin-1 or -2 polypeptide activity by causing constitutive intracellular signaling (or "ligand mimicking"), or by preventing the binding of a native inhibitor of Presenilin-1 or -2 polypeptide activity. Antibodies which bind to Presenilin-1 or -2 polypeptides include, but are not limited to, polyclonal antibodies, monoclonal antibodies (mAbs), human (also called "fully human") antibodies, humanized or chimeric antibodies, single chain antibodies, Fab fragments, F(ab')2 fragments, fragments produced by a Fab expression library, anti-idiotypic (anti-Id) antibodies, and epitope-binding fragments of any of the above. Alternatively, purified and modified Presenilin polypeptides of the disclosure can be administered to modulate interactions between Presenilin polypeptides of the disclosure and Presenilin-1 or -2 binding partners that are not membrane-bound. Such an approach will allow an alternative method for the modification of human Presenilin-1-influenced bioactivity.

Polypeptides of the disclosure may be used to identify antagonists and agonists from cells, cell-free preparations, chemical libraries, and natural product mixtures. The antagonists and agonists may be natural or modified substrates, ligands, enzymes, receptors, etc. of the polypeptides of the instant disclosure, or may be structural or functional mimetics of the polypeptides. Potential antagonists of the instant disclosure may include small molecules, peptides and antibodies that bind to and occupy a binding site of the inventive polypeptides or a binding partner thereof, causing them to be unavailable to bind to their natural binding partners and therefore preventing normal biological activity. Potential agonists include small molecules, peptides and antibodies which bind to the instant polypeptides or binding partners thereof, and elicit the same or enhanced biologic effects as those caused by the binding of the polypeptides of the instant disclosure. Peptide agonists and antagonists of the polypeptides of the disclosure can be identified and utilized according to known methods (see, for example, WO 00/24782 and WO 01/83525, which are incorporated by reference herein).

An approach to development of therapeutic agents is peptide library screening. The interaction of a protein ligand with its receptor often takes place at a relatively large interface. However, as demonstrated for human growth hormone and its receptor, only a few key residues at the interface contribute to most of the binding energy (Clackson et al., 1995; Science 267: 383-386). The bulk of the protein ligand merely displays the binding epitopes in the right topology or serves functions unrelated to binding. Thus, molecules of only "peptide" length (2 to 90 amino acids) can bind to the receptor protein or binding partner of even a large protein ligand such as a polypeptide of the disclosure. Such peptides may mimic the bioactivity of the large protein ligand ("peptide agonists") or, through competitive binding, inhibit the bioactivity of the large protein ligand ("peptide antagonists"). Exemplary peptide agonists and antagonists of polypeptides of the disclosure may comprise a domain of a naturally occurring molecule or may comprise randomized sequences. The term "randomized" as used to refer to peptide sequences refers to fully random sequences (e.g., selected by phage display methods or RNA-peptide screening) and sequences in which one or more residues of a naturally occurring molecule is replaced by an amino acid residue not appearing in that position in the naturally occurring molecule. Phage display peptide libraries have emerged as a powerful method in identifying such peptide agonists and antagonists. See, for example, Scott et al., 1990, Science 249: 386; Devlin et al., 1990, Science 249: 404; U.S. Pat. No. 5,223,409; U.S. Pat. No. 5,733,731; U.S. Pat. No. 5,498,530; U.S. Pat. No. 5,432,018; U.S. Pat. No. 5,338,665; U.S. Pat. No. 5,922,545; WO 96/40987; and WO 98/15833 (each of which is incorporated by reference in its entirety). In such libraries, random peptide sequences are displayed by fusion with coat proteins of filamentous phage. Typically, the displayed peptides are affinity-eluted against an antibody-immobilized extracellular domain of a receptor. The retained phages may be enriched by successive rounds of affinity purification and repropagation. The best binding peptides may be sequenced to identify key residues within one or more structurally related families of peptides. The peptide sequences may also suggest which residues may be safely replaced by alanine scanning or by mutagenesis at the DNA level. Mutagenesis libraries may be created and screened to further optimize the sequence of the best binders (Lowman, 1997, Ann. Rev. Biophys. Biomol. Struct. 26: 401-424). Another biological approach to screening soluble peptide mixtures uses yeast for expression and secretion (Smith et al., 1993, Mol. Pharmacol. 43: 741-748) to search for peptides with favorable therapeutic properties. Hereinafter, this and related methods are referred to as "yeast-based screening." A peptide library can also be fused to the carboxyl terminus of the lac repressor and expressed in E. coli. Another E. coli-based method allows display on the cell's outer membrane by fusion with a peptidoglycan-associated lipoprotein (PAL). Hereinafter, these and related methods are collectively referred to as "E. coli display." In another method, translation of random RNA is halted prior to ribosome release, resulting in a library of polypeptides with their associated RNA still attached. Hereinafter, this and related methods are collectively referred to as "ribosome display." Other methods employ peptides linked to RNA; for example, PROfusion technology, Phylos, Inc. (see, for example, Roberts and Szostak, 1997, Proc. Natl. Acad. Sci. USA 94: 12297-12303). Hereinafter, this and related methods are collectively referred to as "RNA-peptide screening." Chemically derived peptide libraries have been developed in which peptides are immobilized on stable, non-biological materials, such as polyethylene rods or solvent-permeable resins. Another chemically derived peptide library uses photolithography to scan peptides immobilized on glass slides. Hereinafter, these and related methods are collectively referred to as "chemical-peptide screening." Chemical-peptide screening may be advantageous in that it allows use of D-amino acids and other unnatural analogues, as well as non-peptide elements. Both biological and chemical methods are reviewed in Wells and Lowman, 1992, Curr. Opin. Biotechnol. 3: 355-362.

In the case of known bioactive peptides, rational design of peptide ligands with favorable therapeutic properties can be completed. In such an approach, one makes stepwise changes to a peptide sequence and determines the effect of the substitution upon bioactivity or a predictive biophysical property of the peptide (e.g., solution structure). Hereinafter, these techniques are collectively referred to as "rational design." In one such technique, one makes a series of peptides in which one replaces a single residue at a time with alanine. This technique is commonly referred to as an "alanine walk" or an "alanine scan." When two residues (contiguous or spaced apart) are replaced, it is referred to as a "double alanine walk." The resultant amino acid substitutions can be used alone or in combination to result in a new peptide entity with favorable therapeutic properties. Structural analysis of protein-protein interaction may also be used to suggest peptides that mimic the binding activity of large protein ligands. In such an analysis, the crystal structure may suggest the identity and relative orientation of critical residues of the large protein ligand, from which a peptide may be designed (see, e.g., Takasaki et al., 1997, Nature Biotech. 15: 1266-1270). Hereinafter, these and related methods are referred to as "protein structural analysis." These analytical methods may also be used to investigate the interaction between a receptor protein and peptides selected by phage display, which may suggest further modification of the peptides to increase binding affinity.

Peptide agonists and antagonists of polypeptides of the disclosure may be covalently linked to a vehicle molecule. The term "vehicle" refers to a molecule that prevents degradation and/or increases half-life, reduces toxicity, reduces immunogenicity, or increases biological activity or uptake of a therapeutic protein. Exemplary vehicles include an Fc domain or a linear polymer (e.g., polyethylene glycol (PEG), polylysine, dextran, etc.); a branched-chain polymer (see, for example, U.S. Pat. No. 4,289,872; U.S. Pat. No. 5,229,490; WO 93/21259); a lipid; a cholesterol group (such as a steroid); a carbohydrate or oligosaccharide (e.g., dextran); or any natural or synthetic protein, polypeptide or peptide that binds to a salvage receptor or protein transduction domains.

Antibodies that are immunoreactive with the polypeptides of the disclosure are provided herein. Such antibodies specifically bind to the polypeptides via the antigen-binding sites of the antibody (as opposed to non-specific binding). In the disclosure, specifically binding antibodies are those that will specifically recognize and bind with Presenilin polypeptides of the disclosure, homologues, and variants, but not with other molecules. In one embodiment, the antibodies are specific for the polypeptides of the disclosure and do not cross-react with other polypeptides. In this manner, the Presenilin polypeptides of the disclosure, fragments, variants, fusion polypeptides, and the like, as set forth above, can be employed as "immunogens" in producing antibodies immunoreactive therewith.

More specifically, the polypeptides, fragment, variants, fusion polypeptides, and the like contain antigenic determinants or epitopes that elicit the formation of antibodies. These antigenic determinants or epitopes can be either linear or conformational (discontinuous). Linear epitopes are composed of a single section of amino acids of the polypeptide, while conformational or discontinuous epitopes are composed of amino acids sections from different regions of the polypeptide chain that are brought into close proximity upon polypeptide folding (C. A. Janeway, Jr. and P. Travers, Immuno Biology 3:9 (Garland Publishing Inc., 2nd ed. 1996)). Because folded polypeptides have complex surfaces, the number of epitopes available is quite numerous; however, due to the conformation of the polypeptide and steric hinderances, the number of antibodies that actually bind to the epitopes is less than the number of available epitopes (C. A. Janeway, Jr. and P. Travers, Immuno Biology 2:14 (Garland Publishing Inc., 2nd ed. 1996)). Epitopes can be identified by any of the methods known in the art. Thus, one aspect of the disclosure relates to the antigenic epitopes of the polypeptides of the disclosure. Such epitopes are useful for raising antibodies, in particular monoclonal antibodies, as described in more detail below. Additionally, epitopes from the polypeptides of the disclosure can be used as research reagents, in assays, and to purify specific binding antibodies from substances such as polyclonal sera or supernatants from cultured hybridomas. Such epitopes or variants thereof can be produced using techniques well known in the art such as solid-phase synthesis, chemical or enzymatic cleavage of a polypeptide, or using recombinant DNA technology.

As to the antibodies that can be elicited by the epitopes of the polypeptides of the disclosure, whether the epitopes have been isolated or remain part of the polypeptides, both polyclonal and monoclonal antibodies can be prepared by conventional techniques. See, for example, Monoclonal Antibodies, Hybridomas: A New Dimension in Biological Analyses, Kennet et al. (eds.), Plenum Press, New York (1980); and Antibodies. A Laboratory Manual, Harlow and Land (eds.), Cold Spring Harbor Laboratory Press, Cold Spring Harbor, N.Y., (1988); Kohler and Milstein, (U.S. Pat. No. 4,376,110); the human B-cell hybridoma technique (Kosbor et al., 1983, Immunology Today 4:72; Cole et al., 1983, Proc. Natl. Acad. Sci. USA 80:2026-2030); and the EBV-hybridoma technique (Cole et al., 1985, Monoclonal Antibodies And Cancer Therapy, Alan R. Liss, Inc., pp. 77-96). Hybridoma cell lines that produce monoclonal antibodies specific for the polypeptides of the disclosure are also contemplated herein. Such hybridomas can be produced and identified by conventional techniques. The hybridoma producing the mAb of this disclosure may be cultivated in vitro or in vivo. Production of high titers of mAbs in vivo makes this the most common method of production. One method for producing such a hybridoma cell line comprises immunizing an animal with a polypeptide; harvesting spleen cells from the immunized animal; fusing said spleen cells to a myeloma cell line, thereby generating hybridoma cells; and identifying a hybridoma cell line that produces a monoclonal antibody that binds the polypeptide. For the production of antibodies, various host animals may be immunized by injection with one or more of the following: a Presenilin-1 polypeptide, a fragment of a Presenilin-1 polypeptide, a functional equivalent of a Presenilin-1 polypeptide, or a mutant form of a Presenilin-1 polypeptide. Such host animals may include, but are not limited to rabbits, mice and rats. Various adjuvants may be used to increase the immunological response, depending on the host species, including, but not limited to, Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*. The monoclonal antibodies can be recovered by conventional techniques. Such monoclonal antibodies may be of any immunoglobulin class including IgG, IgM, IgE, IgA, IgD, and any subclass thereof.

In addition, techniques developed for the production of "chimeric antibodies" (Takeda et al., 1985, Nature, 314:452-454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a porcine mAb and a human immunoglobulin constant region. The monoclonal antibodies of the disclosure also include humanized versions of murine monoclonal antibodies. Such humanized antibodies can be prepared by known techniques and offer the advantage of reduced immunogenicity when the antibodies are administered to humans. In one embodiment, a humanized monoclonal antibody comprises the variable region of a murine antibody (or just the antigen-binding site thereof) and a constant region derived from a human antibody. Alternatively, a humanized antibody fragment can comprise the antigen-binding site of a murine monoclonal antibody and a variable region fragment (lacking the antigen-binding site) derived from a human antibody. Procedures for the production of chimeric and further engineered monoclonal antibodies include those described in Riechmann et al. (Nature 332:323, 1988), Liu et al. (PNAS 84:3439, 1987), Larrick et al. (Bio/Technology 7:934, 1989), and Winter and Harris (TIPS 14:139, Can, 1993). Procedures to generate antibodies transgenically can be found in GB 2,272,440, U.S. Pat. Nos. 5,569,825 and 5,545,806 and related patents claiming priority therefrom, all of which are incorporated by reference herein. Preferably, for use in humans, the antibodies are human or humanized; techniques for creating such human or humanized antibodies are also well known and are commercially available from, for example, Medarex Inc. (Princeton, N.J.) and Abgenix Inc. (Fremont, Calif.).

Antigen-binding antibody fragments that recognize specific epitopes may be generated by known techniques. For example, such fragments include, but are not limited to: the F(ab')2 fragments which can be produced by pepsin digestion of the antibody molecule and the Fab fragments which can be generated by reducing the disulfide bridges of the (ab')$_2$ fragments. Alternatively, Fab expression libraries may be constructed (Huse et al., 1989, Science, 246:1275-1281) to allow rapid and easy identification of monoclonal Fab fragments with the desired specificity. Techniques described for the production of single chain antibodies (U.S. Pat. No. 4,946,778; Bird, 1988, Science 242:423-426; Huston et al., 1988, Proc. Natl. Acad. Sci. USA 85:5879-5883; and Ward et al., 1989, Nature 334:544-546) can also be adapted to produce single chain antibodies against Presenilin-1 gene products. Single chain antibodies are formed by linking the heavy and light chain fragments of the Fv region via an amino acid bridge, resulting in a single chain polypeptide. In addition, antibodies to a Presenilin-1 polypeptide can, in turn, be utilized to generate anti-idiotype antibodies that "mimic" a Presenilin-1 or -2 polypeptide and that may bind to a Presenilin-1 or -2 polypeptide using techniques well known to those skilled in the art (see, e.g., Greenspan & Bona, 1993, FASEB J 7(5):437-444; and Nissinoff, 1991, J. Immunol. 147(8): 2429-2438).

Screening procedures by which such antibodies can be identified are well known, and can involve immunoaffinity chromatography, for example. Antibodies can be screened for agonistic (i.e., ligand-mimicking) properties. Such antibodies, upon binding to cell surface Presenilin-1, induce biological effects (e.g., transduction of biological signals) similar to the biological effects induced when a Presenilin-1 or -2 binding partner binds to a cell surface Presenilin-1 or -2. Agonistic antibodies can be used to induce Presenilin-1 or -2-mediated activities, such as epithelial barrier formation, stimulatory pathways, or intercellular communication. Those antibodies that can block binding of the Presenilin polypeptides of the disclosure to binding partners for Presenilin-1 can be used to inhibit Presenilin-1 or -2-mediated epithelial barrier formation, intercellular communication, or co-stimulation that results from such binding. Such blocking antibodies can be identified using any suitable assay procedure, such as by testing antibodies for the ability to inhibit binding of Presenilin-1 or -2 to certain cells expressing a Presenilin-1 or -2 binding partner. Alternatively, blocking antibodies can be identified in assays for the ability to inhibit a biological effect that results from binding of a Presenilin-1 or -2 to target cells, such as epithelial barrier formation, using assays described herein. Such an antibody can be employed in an in vitro procedure, or administered in vivo to inhibit a biological activity mediated by the entity that generated the antibody. Disorders caused or exacerbated (directly or indirectly) by the interaction of Presenilin-1 or -2 with cell surface binding partner receptor thus can be treated. A therapeutic method involves in vivo administration of a blocking antibody to a mammal in an amount effective in inhibiting Presenilin-1 or -2 binding partner-mediated biological activity. Human or humanized antibodies can be used in such therapeutic methods. In one embodiment, an antigen-binding antibody fragment is employed. Compositions comprising an antibody that is directed against Presenilin-1 or -2, and a physiologically acceptable diluent, excipient, or carrier, are provided herein. Suitable components of such compositions are as described below for compositions containing Presenilin polypeptides of the disclosure.

Also provided herein are conjugates comprising a detectable (e.g., diagnostic) or a therapeutic agent, attached to the antibody. Examples of such agents are presented above. The conjugates find use in in vitro or in vivo procedures. The antibodies of the disclosure can also be used in assays to detect the presence of the polypeptides or fragments of the disclosure, either in vitro or in vivo. The antibodies also can be employed in purifying polypeptides or fragments of the disclosure by immunoaffinity chromatography.

The goal of rational drug design is to produce structural analogs of biologically active polypeptides of interest or of small molecules with which they interact, e.g., inhibitors, agonists, antagonists, and the like. Any of these examples can be used to fashion drugs which are more active or stable forms of a polypeptide or which enhance or interfere with the function of a polypeptide in vivo (Hodgson J., 1991, Biotechnology 9:19-21, incorporated herein by reference). In one approach, the three-dimensional structure of a polypeptide of interest, or of a polypeptide-inhibitor complex, is determined by x-ray crystallography, by nuclear magnetic resonance, or by computer homology modeling or, most typically, by a combination of these approaches. Both the shape and charges of the polypeptide must be ascertained to elucidate the structure and to determine active site(s) of the polypeptide. Less often, useful information regarding the structure of a polypeptide may be gained by modeling based on the structure of homologous polypeptides. In both cases, relevant structural information is used to design analogous Presenilin-like molecules, to identify efficient inhibitors, or to identify small molecules that may bind a Presenilin of the disclosure. Useful examples of rational drug design may include molecules which have improved activity or stability as shown by Braxton S and Wells J A (1992, Biochemistry 31:7796-7801) or which act as inhibitors, agonists, or antagonists of native peptides as shown by Athauda S B et al. (1993, J Biochem 113:742-746), incorporated herein by reference. The use of Presenilin-1 polypeptide structural information in molecular modeling software systems to assist in inhibitor design and inhibitor-Presenilin-1 polypeptide interaction is also encompassed by the disclosure. A particular method of the disclosure comprises analyzing the three-dimensional structure of Presenilin polypeptides of the disclosure for likely binding sites of substrates, synthesizing a new molecule that incorporates a predictive reactive site, and assaying the new molecule as described further herein.

It is also possible to isolate a target-specific antibody, selected by functional assay, as described further herein, and then to solve its crystal structure. This approach, in principle, yields a pharmacore upon which subsequent drug design can be based. It is possible to bypass polypeptide crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced peptides. The isolated peptides would then act as the pharmacore.

The polypeptides and peptides of the disclosure also find use as carriers for delivering agents attached thereto to cells bearing identified binding partners. The polypeptides thus can be used to deliver diagnostic or therapeutic agents to such cells (or to other cell types found to express binding partners on the cell surface) in in vitro or in vivo procedures. Detectable (diagnostic) and therapeutic agents that can be attached to a polypeptide include, but are not limited to, toxins, other cytotoxic agents, drugs, radionuclides, chromophores, enzymes that catalyze a colorimetric or fluorometric reaction, and the like, with the particular agent being chosen according to the intended application. Among the toxins are ricin, abrin, diphtheria toxin, *Pseudomonas aeruginosa* exotoxin A, ribosomal inactivating polypeptides, mycotoxins such as trichothecenes, and derivatives and fragments (e.g., single chains) thereof. Radionuclides suitable for diagnostic use include, but are not limited to, $^{123}$I, $^{131}$I, $^{99m}$Tc, $^{111}$In, and $^{76}$Br. Examples of radionuclides suitable for therapeutic use are $^{131}$I, $^{211}$At, $^{77}$Br, $^{186}$Re, $^{188}$Re, $^{212}$Pb, $^{212}$Bi, $^{109}$Pd, $^{64}$Cu, and $^{67}$Cu. Such agents can be attached to the polypeptide by any suitable conventional procedure. The polypeptide comprises functional groups on amino acid side chains that can be reacted with functional groups on a desired agent to form covalent bonds, for example. Alternatively, the polypeptide or agent can be derivatized to generate or attach a desired reactive functional group. The derivatization can involve attachment of one of the bifunctional coupling reagents available for attaching various molecules to polypeptides (Pierce Chemical Company, Rockford, Ill.). A number of techniques for radiolabeling polypeptides are known. Radionuclide metals can be attached to polypeptides by using a suitable bifunctional chelating agent, for example. Conjugates comprising polypeptides and a suitable diagnostic or therapeutic agent (preferably covalently linked) are thus prepared. The conjugates are administered or otherwise employed in an amount appropriate for the particular application.

Agents identified by methods provided herein and the peptides of the disclosure may be administered therapeutically or prophylactically to treat diseases associated with amyloid fibril formation, aggregation or deposition, regardless of the clinical setting. The compounds of the disclosure may act to modulate the course of an amyloid related disease using any of the following mechanisms, such as, for example but not limited to: slowing the rate of amyloid fibril formation or deposition; lessening the degree of amyloid deposition; inhibiting, reducing, or preventing amyloid fibril formation; inhibiting amyloid induced inflammation; enhancing the clearance of amyloid from, for example, the brain; or protecting cells from amyloid induced (oligomers or fibrillar) toxicity.

"Modulation" of amyloid deposition includes both inhibition, as defined above, and enhancement of amyloid deposition or fibril formation. The term "modulating" is intended, therefore, to encompass prevention or stopping of amyloid formation or accumulation, inhibition or slowing down of further amyloid aggregation in a subject with ongoing amyloidosis, e.g., already having amyloid aggregates, and reducing or reversing of amyloid aggregates in a subject with ongoing amyloidosis; and enhancing amyloid deposition, e.g., increasing the rate or amount of amyloid deposition in vivo or in vitro. Amyloid-enhancing compounds may be useful in animal models of amyloidosis, for example, to make possible the development of amyloid deposits in animals in a shorter period of time or to increase amyloid deposits over a selected period of time. Amyloid-enhancing compounds may be useful in screening assays for compounds which inhibit amyloidosis in vivo, for example, in animal models, cellular assays and in vitro assays for amyloidosis. Such compounds may be used, for example, to provide faster or more sensitive assays for compounds. In some cases, amyloid enhancing compounds may also be administered for therapeutic purposes, e.g., to enhance the deposition of amyloid in the lumen rather than the wall of cerebral blood vessels to prevent CAA. Modulation of amyloid aggregation is determined relative to an untreated subject or relative to the treated subject prior to treatment.

"Inhibition" of amyloid deposition includes preventing or stopping of amyloid formation, e.g., fibrillogenesis, clearance of soluble Aβ from brain, inhibiting or slowing down of further amyloid deposition in a subject with amyloidosis, e.g., already having amyloid deposits, and reducing or reversing amyloid fibrillogenesis or deposits in a subject with ongoing amyloidosis. Inhibition of amyloid deposition is determined relative to an untreated subject, or relative to the treated subject prior to treatment, or, e.g., determined by clinically measurable improvement, e.g., or in the case of a subject with brain amyloidosis, e.g., an Alzheimer's or cerebral amyloid angiopathy subject, stabilization of cognitive function or prevention of a further decrease in cognitive function (i.e., preventing, slowing, or stopping disease progression), or improvement of parameters such as the concentration of Aβ or tau in the CSF.

As used herein, "treatment" of a subject includes the application or administration of a composition comprising an agent identified by a method of the disclosure to a subject, or application or administration of a composition of the disclosure to a cell or tissue from a subject, who has a amyloid-β related disease or condition, has a symptom of such a disease or condition, or is at risk of (or susceptible to) such a disease or condition, with the purpose of curing, healing, alleviating, relieving, altering, remedying, ameliorating, improving, or affecting the disease or condition, the symptom of the disease or condition, or the risk of (or susceptibility to) the disease or condition. The term "treating" refers to any indicia of success in the treatment or amelioration of an injury, pathology or condition, including any objective or subjective parameter such as abatement; remission; diminishing of symptoms or making the injury, pathology or condition more tolerable to the subject; slowing in the rate of degeneration or decline; making the final point of degeneration less debilitating; improving a subject's physical or mental well-being; or, in some situations, preventing the onset of dementia. The treatment or amelioration of symptoms can be based on objective or subjective parameters; including the results of a physical examination or a psychiatric evaluation. For example, the methods of the disclosure successfully treat a subject's dementia by slowing the rate of or extent of cognitive decline.

While Alzheimer's disease of the familial or the sporadic type is the major dementia found in the aging population, other types of dementia are also found. These include but are not limited to: the fronto-temporal degeneration associated with Pick's disease, vascular dementia, senile dementia of Lewy body type, dementia of Parkinsonism with frontal atrophy, progressive supranuclear palsy and corticobasal degeneration and Downs syndrome associated Alzheimers'. Plaque formation is also seen in the spongiform encephalopathies such as CJD, scrapie and BSE. The disclosure is directed to treatment of such neurodegenerative diseases, particularly those involving neurotoxic protein plaques, eg. amyloid plaques.

Downs syndrome is a serious human disorder that occurs with an incidence of 1 in 800 live births. It is associated with the presence in affected individuals of an extra copy of chromosome 21 (trisomy 21). The β-amyloid precursor protein (β-APP) gene is encoded on chromosome 21, very close to the Down syndrome locus. All patients with Downs syndrome, if they survive beyond 40 years, develop Alzheimer's-like dementia and the deposition of Aβ in their brains. There is good reason, therefore, to propose that the over-production of Aβ is connected directly with the occurrence of the dementia in both AD and Downs syndrome. Therefore, the nature of the identification of therapeutic agents for the amelioration of the symptoms of AD will also be useful for the amelioration of the symptoms of Downs syndrome.

"Dementia" refers to a general mental deterioration due to organic or psychological factors; characterized by disorientation, impaired memory, judgment, and intellect, and a shallow labile affect. Dementia herein includes vascular dementia, ischemic vascular dementia (IVD), frontotemporal dementia (FTD), Lewy body dementia, Alzheimer's dementia, etc. The most common form of dementia among older people is Alzheimer's disease (AD).

The expressions "mild-moderate" or "early stage" AD are used as synonyms herein to refer to AD which is not advanced and wherein the signs or symptoms of disease are not severe. Subjects with mild-moderate or early stage AD can be identified by a skilled neurologist or clinician. In one embodiment, the subject with mild-moderate AD is identified using the Mini-Mental State Examination (MMSE). Herein, "moderate-severe" or "late stage" AD refer to AD which is advanced and the signs or symptoms of disease are pronounced. Such subjects can be identified by a skilled neurologist or clinician. Subjects with this form of AD may no longer respond to therapy with cholinesterase inhibitors, and my have a markedly reduced acetylcholine level. In one embodiment, the subject with moderate-severe AD is identified using the Mini-Mental State Examination (MMSE). "Familial AD" is an inherited form of AD caused by a genetic defect. A "symptom" of AD or dementia is any morbid phenomenon or departure from the normal in structure, function, or sensation, experienced by the subject and indicative of AD or dementia.

An agent may be administered therapeutically or prophylactically to treat diseases associated with amyloid fibril formation, aggregation or deposition. The agents of the disclosure may act to, ameliorate the course of fibril formation; inhibiting neurodegeneration or cellular toxicity induced by amyloid-β; inhibiting amyloid-β induced inflammation; enhancing the clearance of amyloid-β from the brain; or favoring greater catabolism of Aβ.

An agent may be effective in controlling amyloid-β deposition by acting directly on brain Aβ, e.g., by maintaining it in a non-fibrillar form or favoring its clearance from the brain. The compounds may slow down APP processing; may increase degradation of Aβ fibrils by macrophages or by neuronal cells; or may decrease Aβ production by activated microglia. These agents could also prevent Aβ in the brain from interacting with the cell surface and therefore prevent neurotoxicity, neurodegeneration, or inflammation.

An agent identified by a method provided herein may be used to treat Alzheimer's disease (e.g., sporadic or familial AD). The agent may also be used prophylactically or therapeutically to treat other clinical occurrences of amyloid-β deposition, such as in Down's syndrome individuals and in patients with cerebral amyloid angiopathy ("CAA"), hereditary cerebral hemorrhage, or early Alzheimer's disease.

The agent may be used to treat mild cognitive impairment. Mild Cognitive Impairment ("MCI") is a condition characterized by a state of mild but measurable impairment in thinking skills, which is not necessarily associated with the presence of dementia. MCI frequently, but not necessarily, precedes Alzheimer's disease.

Additionally, abnormal accumulation of APP and of amyloid-β protein in muscle fibers has been implicated in the pathology of sporadic inclusion body myositis (IBM) (Askanas, V., et al. (1996) Proc. Natl. Acad. Sci. USA 93: 1314-1319; Askanas, V. et al. (1995) Current Opinion in Rheumatology 7: 486-496). Accordingly, agents identified by a method provided herein amy be used prophylactically or therapeutically in the treatment of disorders in which amyloid-β protein is abnormally deposited at non-neurological locations, such as treatment of EBM by delivery of the compounds to muscle fibers.

Additionally, it has been shown that Aβ is associated with abnormal extracellular deposits, known as drusen, that accumulate along the basal surface of the retinal pigmented epithelium in individuals with age-related macular degeneration (ARMD). ARMD is a cause of irreversible vision loss in older individuals. It is believed that Aβ deposition could be an important component of the local inflammatory events that contribute to atrophy of the retinal pigmented epithelium, drusen biogenesis, and the pathogenesis of ARMD (Johnson, et al., Proc. Natl. Acad. Sci. USA 99(18), 11830-5 (2002)).

Accordingly, the disclosure relates generally to methods of treating or preventing an amyloid-related disease in a subject (preferably a human) comprising administering to the subject a therapeutic amount of an agent or compound identified by a method provided herein, such that amyloid fibril formation or deposition, neurodegeneration, or cellular toxicity is reduced or inhibited. In another embodiment, the disclosure relates to a method of treating or preventing an amyloid-related disease in a subject (preferably a human) comprising administering to the subject a therapeutic amount of a compound identified by a method described herein, such that cognitive function is improved or stabilized or further deterioration in cognitive function is prevented, slowed, or stopped in patients with brain amyloidosis, e.g., Alzheimer's disease, Down's syndrome or cerebral amyloid angiopathy. These compounds can also improve quality of daily living in these subjects.

Further, the disclosure relates to pharmaceutical compositions comprising agents for the treatment of an amyloid-related disease, as well as methods of manufacturing such pharmaceutical compositions.

In general, the agents identified by methods provided herein may be prepared by any method known to the skilled artisan. The agents of the disclosure may be supplied in a solution with an appropriate solvent or in a solvent-free form (e.g., lyophilized). In another aspect of the disclosure, the agents and buffers necessary for carrying out the methods of the disclosure may be packaged as a kit. The kit may be commercially used according to the methods described herein and may include instructions for use in a method of the disclosure. Additional kit components may include acids, bases, buffering agents, inorganic salts, solvents, antioxidants, preservatives, or metal chelators. The additional kit components are present as pure compositions, or as aqueous or organic solutions that incorporate one or more additional kit components. Any or all of the kit components optionally further comprise buffers.

The therapeutic agent may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

To administer the therapeutic agent by other than parenteral administration, it may be necessary to coat the agent with, or co-administer the agent with, a material to prevent its inactivation. For example, the therapeutic agent may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., J. Neuroimmunol. 7, 27 (1984)).

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi.

Suitable pharmaceutically acceptable vehicles include, without limitation, any non-immunogenic pharmaceutical adjuvants suitable for oral, parenteral, nasal, mucosal, transdermal, intravascular (IV), intraarterial (IA), intramuscular (IM), and subcutaneous (SC) administration routes, such as phosphate buffer saline (PBS).

The vehicle can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, isotonic agents are included, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic agent in the required amount in an appropriate solvent with one or a combination of ingredients enumerated above, as required, followed by filtered sterilization. Generally, dispersions are prepared by incorporating the therapeutic agent into a sterile vehicle which contains a basic dispersion medium and the required other ingredients from those enumerated above. In the case of sterile powders for the preparation of sterile injectable solutions, the methods of preparation are vacuum drying and freeze-drying which yields a powder of the active ingredient (i.e., the therapeutic agent) plus any additional desired ingredient from a previously sterile-filtered solution thereof.

The therapeutic agent can be orally administered, for example, with an inert diluent or an assimilable edible carrier. The therapeutic agent and other ingredients may also be enclosed in a hard or soft shell gelatin capsule, compressed into tablets, or incorporated directly into the subject's diet. For oral therapeutic administration, the therapeutic agent may be incorporated with excipients and used in the form of ingestible tablets, buccal tablets, troches, capsules, elixirs, suspensions, syrups, wafers, and the like. The percentage of the therapeutic agent in the compositions and preparations may, of course, be varied. The amount of the therapeutic agent in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic agent calculated to produce the desired therapeutic effect in association with the required pharmaceutical vehicle. The specification for the dosage unit forms of the disclosure are dictated by and directly dependent on (a) the unique characteristics of the therapeutic agent and the particular therapeutic effect to be achieved, and (b) the limitations inherent in the art of compounding such a therapeutic agent for the treatment of amyloid deposition in subjects.

The disclosure therefore includes pharmaceutical formulations comprising agents identified by methods described herein, including pharmaceutically acceptable salts thereof, in pharmaceutically acceptable vehicles for aerosol, oral and parenteral administration. Also, the disclosure includes such agents, or salts thereof, which have been lyophilized and which may be reconstituted to form pharmaceutically acceptable formulations for administration, as by intravenous, intramuscular, or subcutaneous injection. Administration may also be intradermal or transdermal.

In accordance with the disclosure, an agent, and pharmaceutically acceptable salts thereof, may be administered orally or through inhalation as a solid, or may be administered intramuscularly or intravenously as a solution, suspension or emulsion. Alternatively, the agents or salts may also be administered by inhalation, intravenously or intramuscularly as a liposomal suspension.

Pharmaceutical formulations are also provided which are suitable for administration as an aerosol, by inhalation. These formulations comprise a solution or suspension of the desired agent, or a salt thereof, or a plurality of solid particles of the agent or salt. The desired formulation may be placed in a small chamber and nebulized. Nebulization may be accomplished by compressed air or by ultrasonic energy to form a plurality of liquid droplets or solid particles comprising the agents or salts. The liquid droplets or solid particles should have a particle size in the range of about 0.5 to about 5 microns. The solid particles can be obtained by processing the solid agent, or a salt thereof, in any appropriate manner known in the art, such as by micronization. The size of the solid particles or droplets will be, for example, from about 1 to about 2 microns. In this respect, commercial nebulizers are available to achieve this purpose.

A pharmaceutical formulation suitable for administration as an aerosol may be in the form of a liquid, the formulation will comprise a water-soluble agent, or a salt thereof, in a carrier which comprises water. A surfactant may be present which lowers the surface tension of the formulation sufficiently to result in the formation of droplets within the desired size range when subjected to nebulization.

Peroral compositions also include liquid solutions, emulsions, suspensions, and the like. The pharmaceutically acceptable vehicles suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, tragacanth, and sodium alginate; typical-wetting agents include lecithin and polysorbate 80; and typical preservatives include methyl paraben and sodium benzoate. Peroral liquid compositions may also contain one or more components such as sweeteners, flavoring agents and colorants disclosed above.

Pharmaceutical compositions may also be coated by conventional methods, typically with pH or time-dependent coatings, such that the subject agent is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, waxes, and shellac.

Other compositions useful for attaining systemic delivery of the subject agents include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

The compositions of this disclosure can also be administered topically to a subject, e.g., by the direct laying on or spreading of the composition on the epidermal or epithelial tissue of the subject, or transdermally via a "patch". Such compositions include, for example, lotions, creams, solutions, gels and solids. These topical compositions may comprise an effective amount, usually at least about 0.1%, or even from about 1% to about 5%, of an agent of the disclosure. Suitable carriers for topical administration typically remain in place on the skin as a continuous film, and resist being removed by perspiration or immersion in water. Generally, the carrier is organic in nature and capable of having dispersed or dissolved therein the therapeutic agent. The carrier may include pharmaceutically acceptable emolients, emulsifiers, thickening agents, solvents and the like.

As described above and further in the Examples below, the disclosure supports that specific adhesion between β-APP-presenting and PS-presenting cells have different physiological consequences, one a transcellular (juxtacrine) signaling process associated with the normal function of these proteins, and the other resulting eventually in the proteolysis of β-APP to form Aβ, leading to the pathology of Alzheimer's disease.

G-protein coupled receptors (GPCRs) share a common structural motif. Generally, GPCRs have seven sequences of between 22 to 24 hydrophobic amino acids that form seven alpha helices, each of which spans the membrane. The transmembrane helices are joined by strands of amino acids between transmembrane-2 and transmembrane-3, transmembrane-4 and transmembrane-5, transmembrane-6 and transmembrane-7 on the exterior, or "extracellular" side, of the cell membrane (these are referred to as "extracellular" regions 1, 2 and 3 (EC-1, EC-2 and EC-3), respectively). The transmembrane helices are also joined by strands of amino acids between transmembrane-1 and transmembrane-2, transmembrane-3 and transmembrane-4, and transmembrane-5 and transmembrane-6 on the interior, or "intracellular" side, of the cell membrane (these are referred to as "intracellular" regions 1, 2 and 3 (IC-1, IC-2 and IC-3), respectively). The "carboxy" ("C") terminus of the receptor lies in the intracellular space within the cell, and the "amino" ("N") terminus of the receptor lies in the extracellular space outside of the cell.

Generally, when a ligand binds with the receptor (often referred to as "activation" of the receptor), there is a change in the conformation of the intracellular region that allows for coupling between the intracellular region and an intracellular "G-protein." It has been reported that GPCRs are "promiscuous" with respect to G proteins, i.e., that a GPCR can interact with more than one G protein. See, Kenakin, T., 43 Life Sciences 1095 (1988). Although other G proteins exist, currently, Gq, Gs, Gi, Gz and Go are G proteins that have been identified. Endogenous ligand-activated GPCR coupling with the G-protein begins a signaling cascade process (referred to as "signal transduction"). Under normal conditions, signal transduction ultimately results in cellular activation or cellular inhibition. It is thought that the IC-3 loop as well as the carboxy terminus of the receptor interact with the G protein.

Receptor activated G proteins are bound to the inside surface of the cell membrane. They consist of the Gα and the tightly associated Gβγ subunits. When a ligand activates the G protein-coupled receptor, it induces a conformation change in the receptor (a change in shape) that allows the G protein to now bind to the receptor. The G protein then releases its bound GDP from the Gα subunit, and binds a new molecule of GTP. This exchange triggers the dissociation of the Gα subunit, the Gβγ dimer, and the receptor. Both, Gα-GTP and Gβγ, can then activate different signalling cascades (or second messenger pathways) and effector proteins, while the receptor is able to activate the next G protein. The Gα subunit will eventually hydrolyze the attached GTP to GDP by its inherent enzymatic activity, allowing it to reassociate with Gβγ and starting a new cycle.

The alpha subunit of the guanine nucleotide-binding protein $G_o$ ("o" for other) mediates signal transduction between a variety of receptors and effectors. Two forms of Go alpha subunit have been isolated from brain tissue libraries. These two forms, $G_{oA}$ alpha and $G_{oB}$ alpha (also referred to as $G_{oA}$ and $G_{oB}$), are the products of alternative splicing. $G_{oA}$ alpha transcripts are present in a variety of tissues but are most abundant in brain. The $G_{oB}$ alpha transcript is expressed at highest levels in brain and testis.

GPCRs comprise one of the largest gene families in the human genome, and mediate a huge variety of cellular functions regulated by neurotransmitters, hormones, chemokines, and many other molecules. Timely uncoupling of GPCR signaling is crucial for maintaining appropriateness and integrity of the GPCR-mediated physiological functions. This uncoupling is primarily mediated by a much smaller gene family, currently numbering seven members of GPCR kinases (GRKs). The specificity for a few GRK members to regulate a huge numbers of GPCRs is controlled in an agonist-dependent manner. In another words, GRKs preferentially bind to and phosphorylate agonist-occupied GPCRs to uncouple receptor from corresponding G-protein, a process known as homologous desensitization. Based on structural similarities, seven known GRK members are classified into four subfamilies (GRK1, GRK2/3, GRK4/5/6 and GRK7), with GRK2/3 and GRK5/6 having ubiquitous distributions including brain. Dysregulation of GRK2, probably GRK5 as well, has been implicated in the pathogenesis of chronic heart failure, myocardial ischemia, and hypertension, and other cardiovascular disorders, where the GRKs have been extensively studied. Failure to desensitize rhodopsin signaling by GRK1 can lead to photoreceptor cell death, and is believed to contribute to retinitis pigmentosa. In addition, increased GRK2 levels have been associated with opiate addiction. Aside from these, however, roles of GRKs in many other pathological conditions potentially associated with GPCR deregulation, such as in AD, remain virtually unexplored.

Due to the membrane location of GPCRs, GRK's retention on the plasma membrane or in the cytosol physically affects its access and binding to GPCRs. In resting cells, GRK4 subfamily members (including GRK4/5/6) are tightly associated with the plasma membrane, while GRK2 subfamily members (GRK2/3) are primarily cytosolic and translocate to the membrane when cells are stimulated by GPCR agonists. However, in active cells, subcellular localization of GRKs appears to be determined by the content and capacity of GRK-binding factors in membrane versus cytosol. Phospholipids, particularly phosphatidylinositol-4,5-biphosphate, appear to play a role in GRKs adherence to the membrane and bind GPCRs, while phosphatidylserine may also enhance GRK2 binding to GPCRs on the membrane. On the other hand, calcium/calmodulin and other calcium-binding proteins, as well as actin, actinin, and the like may contribute to sequester GRKs in the cytosol and inhibit binding of GRKs to GPCRs.

In AD brains, significant membrane alterations, aberrant phosphoinositide metabolism, disrupted calcium homeostasis and disorganized cytoskeleton proteins could all influence the subcellular distribution of GRKs. In addition, increased β-amyloid, a hydrophobic peptide central to AD pathogenesis, has been shown to decrease membrane phosphatidylinositol-4,5-biphosphate and increase $[Ca^{2+}]_i$.

The disclosure is based, in part, upon the demonstration that Presenilins function as a type of G-protein coupled receptors (GPCRs), resulting in secondary messaging and downstream effects. Evidence of a 7-TM structure (like that of rhodopsin) for PS-1 and PS-2 has led to the examination regarding whether PS-1 and PS-2 belong to the G-Protein coupled receptor superfamily of proteins, which all share essentially a similar structure. Although PS does not exhibit any substantial amino acid homologies with any of the approximately 1,000 GPCR's so far examined, the fact that all of these GPCR's are 7-TM integral proteins, with many showing no sequence homologies with any others, allows for the possibility that PS molecules are also GPCRs.

GPCR activity of presenilins was identified using a N141I-PS-2 mutation. The mutation, linked with FAD in Volga German families, caused PC-12 cell death in a Pertussis toxin (PTx) sensitive manner. Other studies suggested that within the 39 amino acid residue carboxyl-terminal domain of PS-1 (located in the cytoplasm in almost all topographic models of PS-1 in the membrane) there exists a specific binding and regulating domain for the brain $G_o$ protein. This domain of PS-1 that binds $G_o$ in vitro also shows some local amino acid sequence homologies with the G-binding domains of two other GPCR proteins, the D2-dopaminergic, and the 5HT-1B receptors, as well as the G-protein activating oligopeptide, mastoparan. The possibility that PS-1 as a functional GPCR is further described herein.

The disclosure demonstrates that G-protein $G_o$ binds full-length PS-1, and is inhibited by Pertussis toxin (PTx). In addition, only $G_{oA}$ binds PS-1, not $G_{oB}$. Transfection of ES null cells with a tail-less construct of PS-1, demonstrates that most of the binding occurs at the carboxyl terminal tail of PS-1. However, these results indicate that other cytoplasmic loop regions may be involved in the binding, since very small amounts of binding occurred in the presence of tail-less PS-1. The disclosure also demonstrates that the G-protein binds not only to PS-1 but also PS-2 and that for PS-2, in addition to the binding of $G_{oA}$, $G_{oB}$ also binds intact PS-2. This binding is still present when tail-less PS-2 is used in place of full-length PS-2. These results suggest that $G_{oB}$ binds PS-2 at a cytoplasmic domain other than the C-tail. A greater than 700% increase in $^{35}$S-GTPγS—labeled $G\alpha_{oA}$ (but not $G\alpha_{oB}$) binding to PS-1. For PS-2 there is similarly a greater than 700% increase over basal levels of $^{35}$S-GTPγS-labeled $G\alpha_{oA}$ binding as well as ~300% increase in $^{35}$S-GTPγS-labeled $G\alpha_{oB}$. Treatment with PTx inhibits the incorporation of $^{35}$S-GTPγS to both $G_{oA}$ and $G_{oB}$.

Thus, $G_{oA}$ binds to both PS-1 and PS-2 at similar rates, whereas the binding of $G_{oB}$ to PS-2 is less than half that observed for $G_{oA}$ under the same experimental conditions. The data confirm a functional consequence of the G-protein coupling to PS-1 and PS-2 and further characterize the two presenilin proteins as G-protein coupled receptors (GPCRs).

PS-1 and PS-2 appear to have more features in common with family "3" GPCRs (as described above) than with either of the other two families—both have large extra-cellular domains (the N-terminal, and the hydrophilic loop between TM VI and VII), a feature of family 3 GPCRs. Ligand binding in family 3 GPCRs appears to take place exclusively via the extra-cellular domains, generally the amino terminal domain. The N-terminal domain of PS-1 or PS-2 is sufficient for in vitro binding of PS-1 or PS-2 respectively, to β-APP, a proposed ligand and possible agonist of presenilin GPCR activation. Some family 3 members form homodimers, usually by di-sulfide bonds via extra-cellular Cys residues. It is well known that PS-1 and PS-2 exist in the membrane as dimers. Further, they both have Cys residues in their extra-cellular domains (7-TM structure. Family 3 GPCRs all have the 3rd intracellular loop as the shortest loop and this is conserved among each type. Likewise, the third intracellular loop in PS-1 and PS-2 is the shortest loop, consisting of the sequence KYLPEW (SEQ ID NO:2 from amino acid 239 to 243 and SEQ ID NO:4 from amino acid 245 to 250), which is completely conserved. Some members of family 3 GPCRs interact directly via their carboxyl terminal PDZ binding domains with intracellular PDZ-domain proteins such as Homer. There is a PDZ binding domain in the carboxyl terminal tail of PS-1 which has been shown to bind to several PDZ proteins.

PS are expressible at the cell-surface and have 7-TM structures and PS-1 and PS-2 participate in a specific cell-cell interaction with β-APP; this β-APP:PS mediated intercellular interaction results in transient increase in tyrosine kinase activity and protein tyrosine phosphorylation. Furthermore, a 8-APP:PS mediated cell-cell interaction is required for at least the major part of the production of Aβ. The intercellular interaction between β-APP and PS activate G-protein binding to PS, due to cross-talk between protein tyrosine kinases and the G-protein signaling pathways.

Because the disclosure demonstrates $G_o$ activation by PS ultimately affects Aβ production, the disclosure provides, in one aspect, a drug therapy for AD using appropriately designed inhibitors of PS-$G_o$ specific binding.

As described herein, experiments were performed to detect such possible intercellular protein tyrosine phosphorylation signaling events. It was shown that when cultured DAMI (human megakaryoblast) cells that were transiently transfected with β-APP were mixed with DAMI cells transfected with PS-1, or PS-2, within several minutes after mixing, the cell extracts showed significant transient increases in protein tyrosine kinase activity and in phosphotyrosine (PTyr) modification of protein substrates, that did not appear in controls, or in cell mixtures containing inhibitors of the specific β-APP:PS binding. The downstream consequences of this signaling were different depending on whether PS-1 or PS-2 was engaged in the intercellular binding to β-APP, because the spectrum of proteins that showed enhanced tyrosine phosphorylation was altogether different in the two cases, suggesting a distinction between, rather than a redundancy of, the biochemical functions of the two closely homologous PS proteins.

Furthermore, the disclosure demonstrates the biological pathways described above by using embryonic stem (ES) cells derived from PS-1$^{-/-}$, PS-2$^{-/-}$ double null mice herein referred to as ES double-null cells, either untransfected in control experiments, or transfected with β-APP. In the latter case, the β-APP-transfected ES cells are mixed with either PS-1- or PS-2-transfected DAMI cells; the DAMI cells do not express significant amounts of endogenous β-APP on their surfaces. In this mixed cell-culture system, therefore, the β-APP-transfected ES double-null cells serve as the only source of cell-surface expressed β-APP, while the PS-transfected DAMI cells are the only source of cell-surface expressed PS. If a β-APP:PS specific signaling event occurs in this system, it is the result of a juxtacrine interaction between the two cell types. The disclosure demonstrates just such an interaction.

Evidence is provided that signaling is accompanied by transient elevations in Src family tyrosine kinase activity, and has identified the individual Src family member mediating the intercellular signaling between β-APP and PS-1 to be pp60c-src. In contrast, the β-APP:PS-2 signaling involves the Src family member Lyn. These signaling events affect normal physiology. For example, they may play a role in the physiological defects encountered in the development of β-APP null mice. The Src family of kinases are implicated in cancer, immune system dysfunction and bone remodeling diseases. For general reviews, see Thomas and Brugge, Annu. Rev. Cell Dev. Biol. 1997, 13, 513; Lawrence and Niu, Pharmacol. Ther. 1998, 77, 81; Tatosyan and Mizenina, Biochemistry (Moscow) 2000, 65, 49-58; Boschelli et al., Drugs of the Future 2000, 25(7), 717.

Members of the Src family include the following eight kinases in mammals: Src, Fyn, Yes, Fgr, Lyn, Hck, Lck, and Blk. These are nonreceptor protein kinases that range in molecular mass from 52 to 62 kD. All are characterized by a common structural organization that is comprised of six distinct functional domains: Src homology domain 4 (SH4), a unique domain, SH3 domain, SH2 domain, a catalytic domain (SH1), and a C-terminal regulatory region. Tatosyan et al. Biochemistry (Moscow) 2000, 65, 49-58. Based on published studies, Src kinases are considered as potential therapeutic targets for various human diseases.

GSK-3 activity is also associated with Alzheimer's disease. This disease is characterized by the presence of the well-known β-amyloid peptide and the formation of intracellular neurofibrillary tangles. The neurofibrillary tangles contain hyperphosphorylated Tau protein, in which Tau is phosphorylated on abnormal sites. GSK-3 has been shown to phosphorylate these abnormal sites in cell and animal models. Furthermore, inhibition of GSK-3 has been shown to prevent hyperphosphorylation of Tau in cells. In transgenic mice overexpressing GSK3, significant increased Tau hyperphosphorylation and abnormal morphology of neurons were observed. Active GSK3 accumulates in cytoplasm of pretangled neurons, which can lead to neurofibrillary tangles in brains of patients with AD. Inhibition of GSK-3 slows or halts the generation of neurofibrillary tangles and thus treats or reduces the severity of Alzheimer's disease. Evidence for the role GSK-3 plays in Alzheimer's disease has been shown in vitro (see, e.g., Aplin et al. (1996), J Neurochem 67:699; Sun et al. (2002), Neurosci Lett 321:61; Takashima et al. (1998), PNAS 95:9637; Kirschenbaum et al. (2001), J Biol Chem 276:7366; Takashima et al. (1998), Neurosci Res 31:317; Takashima et al. (1993), PNAS 90:7789; Suhara et al. (2003), Neurobiol Aging. 24:437; De Ferrari et al. (2003) Mol Psychiatry 8:195; and Pigino et al., J Neurosci, 23:4499, 2003). Evidence for the role GSK-3 plays in Alzheimer's disease has been shown in vivo (See, e.g., Yamaguchi et al. (1996), Acta Neuropathol 92:232; Pei et al. (1999), J Neuropath Exp Neurol 58:1010; Hernandez et al. (2002), J Neurochem 83:1529; De Ferrari et al. (2003) Mol Psychiatry 8:195; McLaurin et al., Nature Med, 8:1263, 2002; and Phiel et al. (2003) Nature 423:435.

Presenilin-1 and kinesin-1 are also substrates for GSK-3 and relate to another mechanism for the role GSK-3 plays in Alzheimer's disease, as was recently described by Pigino, G., et al., Journal of Neuroscience (23:4499, 2003). It was found that GSK3beta phosphorylates kinsesin-1 light chain, which results in a release of kinesin-1 from membrane-bound organelles, leading to a reduction in fast anterograde axonal transport. A mutation in PS-1 may deregulate and increase GSK-3 activity, which in turn, impairs axonal transport in neurons. The consequent reductions in axonal transport in affected neurons ultimately lead to neurodegeneration.

The disclosure supports that specific adhesion between β-APP-presenting and PS-presenting cells have different physiological consequences, one a transcellular (juxtacrine) signaling process associated with the normal function of these proteins, and the other resulting eventually in the proteolysis of β-APP to form Aβ, leading to the pathology of Alzheimer's disease. Evidence for a juxtacrine interaction in this system was obtained with cultured DAMI cells appropriately transfected with either 13-APP, or with PS-1 or PS-2; a specific β-APP:PS mediated cell-cell interaction led to rapid and transient increases in protein tyrosine kinase activity and protein tyrosine phosphorylation within most likely one, or possibly both, of the adhering cells. DAMI cells were employed because these cells do not normally express significant amounts of endogenous β-APP at the cell surface, and because they are easy to detach mechanically from the cell substratum. Thus, by transfecting ES double-null cells with β-APP, cells expressing only surface β-APP but not PS were made available, and by transfecting DAMI cells with either PS-1 or PS-2, additional cells were produced that expressed a PS protein at the surface, and no significant β-APP.

Mixing experiments between these transfected cells, as the results show, reveal signaling between β-APP and PS (FIG. 5), which result from a juxtacrine interaction; i.e., a reaction involving membrane-bound PS on one cell surface with β-APP on another. This interaction is specifically inhibited both by soluble β-APP (the exoplasmic domain of β-APP), and by the N-terminal domain of PS-1 fused to FLAG, demonstrating the dual specificity of the interaction of β-APP with PS.

The downstream consequences of this signaling are different depending on whether PS-1 or PS-2 is engaged in the intercellular binding to β-APP. The spectrum of proteins modified by tyrosine phosphorylation differed depending on whether PS-1 or PS-2 was involved in the specific intercellular binding to β-APP. The disclosure identifies c-Src as a protein that undergoes the major transient increases in phosphorylation when β-APP and PS-1 interact intercellularly. The Src kinase family member Lyn appears to be the predominant (or at least a major) Src kinase involved PS-2 intercellular binding to β-APP. Together these results show distinct signaling mechanisms that can result in different rather than redundant physiological functions for the two closely homologous presenilin proteins.

The disclosure demonstrates that juxtacrine signaling between β-APP and either PS-1 or PS-2 results in rapid transient tyrosine kinase activation that is different between the two PS proteins. C-Src or Lyn are recruited upon the binding of β-APP with PS-1 or PS-2, respectively. Recruitment would suggest that a signaling complex is formed transiently in vivo at sites of cell-cell contact, setting in motion a cascade of phosphorylation events that result in developmental consequences. Identifying the region(s) of Src necessary for association with the β-APP:PS-1 complex provides valuable information regarding the assembly and activation of a β-APP:PS-1 signaling complex and indicates whether or not the interaction between the β-APP:PS complex and the kinases is direct or indirect. β-APP is not known to be phosphorylated on cytoplasmic tyrosine residues, and neither is PS-1, so direct binding through the SH2 domain of c-Src is unlikely since this domain binds only at phosphorylated tyrosine residues.

Direct binding can occur via the SH3 domain of Src. SH3 domains recognize proline-rich sequences containing the core P—X—X—P (SEQ ID NO:10), where X denotes any amino acid. Ligands recognize the SH3 binding surface in one of two opposite orientations. Peptides that bind in a type 1 orientation conform to the consensus sequence R—X-L-P—X—Z—P (SEQ ID NO:11) where Z is normally a hydrophobic or Arg residue (Kay et al., 2000). Interestingly, both PS-1 and PS-2 have a conserved type 1 SH3 binding site (LPALP; see SEQ ID NO:2 from amino acid 432 to 436 or SEQ ID NO:4 from amino acid 413 to 417)) in the cytoplasmic carboxyl terminal region.

A number of agents that inhibit GPCR interactions are known in the art. In addition, a number of kinase (e.g., c-src, fln and the like) inhibitors are known in the art and can be used in the methods of the disclosure. Compositions comprising such agents in pharmaceutically acceptable carriers for treating AD or which can be used to modulate memory function are contemplated by the disclosure.

Specific GPCR screening assay techniques are known to the skilled artisan. For example, once candidate compounds are identified using the "generic" G protein-coupled receptor assay (e.g., an assay to select compounds that are antagonists, agonists, partial agonists, or inverse agonists), further screening to confirm that the compounds have interacted at the receptor site can be performed. For example, a compound identified by the "generic" assay may not bind to the receptor, but may instead merely "uncouple" the G protein from the intracellular domain.

G-protein activity can be determined by assaying enzymes associated with a G-protein. For example, $G_s$ stimulates the enzyme adenylyl cyclase. $G_i$ (and $G_z$ and $G_o$), on the other hand, inhibit this enzyme. Adenylyl cyclase catalyzes the conversion of ATP to cAMP; thus, constitutively activated GPCRs that couple the $G_s$ protein are associated with increased cellular levels of cAMP. On the other hand, constitutively activated GPCRs that couple $G_i$ (or $G_z$, $G_o$) protein are associated with decreased cellular levels of cAMP. See, generally, "Indirect Mechanisms of Synaptic Transmission," Chpt. 8, From Neuron To Brain (3rd Ed.) Nichols, J. G. et al eds. Sinauer Associates, Inc. (1992). Thus, assays that detect cAMP can be utilized to determine if a candidate compound is, e.g., an inverse agonist or antagonist to the receptor (i.e., such a compound would decrease the levels of cAMP). A variety of approaches known in the art for measuring cAMP can be utilized; a most preferred approach relies upon the use of anti-cAMP antibodies in an ELISA-based format. Another type of assay that can be utilized is a whole cell second messenger reporter system assay. Promoters on genes drive the expression of the proteins that a particular gene encodes. Cyclic AMP drives gene expression by promoting the binding of a cAMP-responsive DNA binding protein or transcription factor (CREB) that then binds to the promoter at specific sites called cAMP response elements and drives the expression of the gene. Reporter systems can be constructed which have a promoter containing multiple cAMP response elements before the reporter gene, e.g., β-galactosidase or luciferase. Thus, a constitutively activated Gs-linked receptor causes the accumulation of cAMP that then activates the gene and expression of the reporter protein. The reporter protein such as galactosidase or luciferase can then be detected using standard biochemical assays.

$G_q$ and $G_o$ are associated with activation of the enzyme phospholipase C, which in turn hydrolyzes the phospholipid $PIP_2$, releasing two intracellular messengers: diacycloglycerol (DAG) and inisitol 1,4,5-triphosphate ($IP_3$). Increased accumulation of $IP_3$ is associated with activation of $G_q$- and $G_o$-associated receptors. See, generally, "Indirect Mechanisms of Synaptic Transmission," Chpt. 8, From Neuron To Brain ($3^{rd}$ Ed.) Nichols, J. G. et al eds. Sinauer Associates, Inc. (1992). Assays that detect $IP_3$ accumulation can be utilized to determine if a candidate compound is, e.g., an inverse agonist to a $G_q$- or $G_o$-associated receptor (i.e., such a compound would decrease the levels of $IP_3$). $G_g$-associated receptors can also been examined using an AP1 reporter assay in that dependent phospholipase C causes activation of genes containing AP1 elements; thus, activated $G_g$-associated receptors will evidence an increase in the expression of such genes, whereby inverse agonists/antagonists thereto will evidence a decrease in such expression, and agonists will evidence an increase in such expression. Commercially available assays for such detection are available.

Similarly, agents or test compound or drug candidates that interact with an extracellular domain or PS-1, PS-2 and/or β-APP and prevent their natural intercellular interaction can be used to treat Alzheimer's Disease and/or reduce Aβ production. Both G-protein activation and Aβ production are inhibited by specific inhibition of β-APP:PS intercellular interaction. G-protein activation and Aβ production are inhibited by the presence in the co-culture of Pertussis toxin, an inhibitor of $G_o$ activation. Demonstrating that the G-protein activation that follows β-APP:PS-1 intercellular interaction is on the pathway of Aβ production from β-APP. These results support a direct role of PS in G-protein signaling and may provide new avenues for the development of drug candidates for AD.

As described herein a β-APP binding domain of Presenilin refers to either naturally occurring or synthetic, e.g., protein, oligopeptide (e.g., from about 5 to about 100 amino acids in length, typically from about 5 to 50, 5-20 or 5-15 amino acids in length) that binds to a β-APP extracellular domain.

An "agonist" refers to an agent that binds to a polypeptide or polynucleotide of the disclosure, stimulates, increases, activates, facilitates, enhances activation, sensitizes or up regulates the activity or expression of a polypeptide or polynucleotide of the disclosure.

An "antagonist" refers to an agent that inhibits expression of a polypeptide or polynucleotide of the disclosure or binds to, partially or totally blocks stimulation, decreases, prevents, delays activation, inactivates, desensitizes, or down regulates the activity of a polypeptide or polynucleotide of the disclosure.

A "small organic molecule" refers to an organic molecule, either naturally occurring or synthetic, that has a molecular weight of more than about 50 Daltons and less than about 2500 Daltons, preferably less than about 2000 Daltons, preferably between about 100 to about 1000 Daltons, more preferably between about 200 to about 500 Daltons.

"Determining the functional effect" refers to assaying for a compound that increases or decreases a parameter that is indirectly or directly under the influence of presenilin, e.g., measuring physical and chemical or phenotypic effects of e.g., presenilin interactions with a G-protein or β-APP. Such functional effects can be measured by any means known to those skilled in the art, e.g., changes in spectroscopic (e.g., fluorescence, absorbance, refractive index), hydrodynamic (e.g., shape), chromatographic, or solubility properties for the protein; measuring inducible markers or transcriptional activation of the protein; measuring binding activity or binding assays, e.g. binding to antibodies; measuring changes in ligand binding affinity; measurement of calcium influx; measurement of the accumulation of an enzymatic product of a polypeptide of the disclosure or depletion of an substrate; changes in enzymatic activity, measurement of changes in protein levels of a polypeptide of the disclosure; measurement of RNA stability; G-protein binding; GPCR phosphorylation or dephosphorylation; tau phosphorylation or dephosphorylation, signal transduction, e.g., receptor-ligand interactions, second messenger concentrations (e.g., cAMP, $IP_3$, or intracellular $Ca^{2+}$); identification of downstream or reporter gene expression (CAT, luciferase, beta-gal, GFP and the like), e.g., via chemiluminescence, fluorescence, colorimetric reactions, antibody binding, inducible markers, and ligand binding assays. In addition, β-APP binding to presenilin and Aβ production can also be used as determinants of a functional effect on presenilin activity.

The working examples provided below are to illustrate, not limit, the disclosure. Various parameters of the scientific methods employed in these examples are described in detail below and provide guidance for practicing the disclosure in general.

EXAMPLES

Example 1 cDNAs for G-proteins $G\alpha_{oA}$ and $G\alpha_{oB}$ in pcDNA3 were purchased from UMR cDNA Resource Center, Rolla, Mo.

Full-length human PS-1 and PS-2 cDNAs in pcDNA3 were cloned by PCR as already described. Tail-less constructs of PS-1 and PS-2 were constructed in pcDNA3 in which only the cytoplasmic domain of PS-1 or PS-2 immediately following the last TM-domain is deleted (this construct comprises of amino acids 1-430 of PS-1 and 1-410 of PS-2).

Cell culture: ES (PS-1$^{-/-}$/PS-2$^{-/-}$) cells were cultured according to published protocols.

Transfections: ES (PS-1$^{-/-}$/PS-2$^{-/-}$) were transiently transfected with 15 μg of pcDNA constructs of full-length human PS-1 or PS-2 and the cDNA of the desired G-proteins using the lipofectamine (Invitrogen) method. Briefly, the lipofectamine—DNA solution was be left at room temperature for 30 mins, mixed with enough serum-free medium and added to the cells. Cells were incubated for 5 h at 37° C. in a $CO_2$ incubator after which the medium was replenished with serum and cells harvested 12-24 hours after transfection.

Immunoprecipitations: 24 h after transfection, the culture medium was removed, and cells scraped in 200 μl of extraction buffer. Whole cell-extracts were made by sonication, using the solubilization conditions of 5 mine et al (50 mM HEPES/NaOH, pH 7.4, 1 mM EDTA, 1 mM DTT, 1% Triton X-100, 60 mM octylglycoside and protease inhibitors). 100 μg of each extract was immunoprecipitated using monoclonal antibodies to the large loop of PS-1 (MAB5232) or PS-2 (MA1-754). The immunoprecipitated proteins were next separated on 12% SDS PAGE and transferred to a membrane. Western blot hybridization against antibodies to the G protein $G_o$ (K-20, sc-387 from Santa Cruz Biotechnology, affinity purified; this polyclonal antibody recognizes both $G_{oA}$ and $G_{oB}$) was then carried out.

Western blot hybridizations: Immunoprecipitated proteins were boiled for 5 min in loading buffer (50 mM Tris, pH 6.8, 0.1 M DTT, 2% SDS, 0.1% bromophenol blue, 10% glycerol), separated electrophoretically on SDS-PAGE (12%) gels, and the proteins transferred onto nitrocellulose filters. Filters were incubated with the primary polyclonal rabbit G-protein antibodies followed by horse radish peroxidase-conjugated goat anti-rabbit IgG. Filter-bound peroxidase activity was detected by chemiluminescence.

Binding of G-protein $G_o$ to PS-1 ES (PS-1$^{-/-}$/PS-2$^{-/-}$) cells were transiently transfected with cDNA to full-length human PS-1 and the cDNA of the G-proteins $G_{oA}$ or $G_{oB}$ (UMR cDNA Resource Center, Rolla, Mo.). 24 h after transfection, whole cell-extracts were made by sonication, using the solubilization conditions of 5 mine et al (50 mM HEPES/NaOH, pH 7.4, 1 mM EDTA, 1 mM DTT, 1% Triton X-100, 60 mM octylglycoside and protease inhibitors). 100 μg of each extract was immunoprecipitated using monoclonal antibodies to the large loop, which is extracellular in the 7-TM model (Mab #5232, Chemicon, which was used in previous published work). The immunoprecipitated proteins were next separated on 12% SDS PAGE and transferred to a membrane. Western blot hybridization against antibodies to both, PS-1 and $G_o$ (K-20, sc-387 from Santa Cruz Biotechnology, affinity purified; this polyclonal antibody recognizes both $G_{oA}$ and $G_{oB}$) was then carried out.

Binding of G-protein $G_o$ to PS-2: ES (PS-1$^{-/-}$/PS-2$^{-/-}$) were transiently transfected with cDNA of full-length human PS-2 and the cDNA of the G-proteins $G_{oA}$ or $G_{oB}$ (UMR cDNA Resource Center, Rolla, Mo.). 24 h after transfection, whole cell-extracts were made by sonication, using the solubilization conditions of 5 mine et al (50 mM HEPES/NaOH, pH 7.4, 1 mM EDTA, 1 mM DTT, 1% Triton X-100, 60 mM octylglycoside and protease inhibitors). 100 μg of each extract was immunoprecipitated using mouse monoclonal antibodies to the large loop of PS-2 (MA1-754 from Affinity BioReagents). The immunoprecipitated proteins were next separated on 12% SDS PAGE and transferred to a membrane. Western blot hybridization against antibodies to both, PS-2 and $G_o$ was then carried out.

Pertussis Toxin Treatment: The PTx protomer was incubated with 10 mM DTT at 37° C. for 10 min to convert it to its enzymatically active form. 5 h after transfecting ES cells with PS-1 or PS-2 and the G-protein cDNAs, 500 ng/ml of activated PTx was added to the cells in culture medium in the presence of 1 mM NAD, 2 mM $MgCl_2$ and 1 mM EDTA and the cells incubated at 37° C. in the presence of 5% $CO_2$ for 12 h. Cells were then harvested and examined for [$^{35}$S]GTPγS incorporation as described below.

GTPγS Binding: Cells were harvested and proteins solubilized by sonication in solubilization buffer (50 mM HEPES/NaOH pH 7.4, 1 mM EDTA, 1 mM DTT, 1% Triton-X100, 60 mM octylglycoside, 1× Protease inhibitor mix). 100 μg of protein was mixed with an equal volume of Buffer B (50 mM HEPES/NaOH pH 7.4, 40 μM GDP, 50 mM $MgCl_2$, 100 mM NaCl) in a volume of 200 μl. The reaction was started with 50 nM [$^{35}$S]GTPγS (1250 Ci/mmol) and incubation carried out for 60 min at RT after which the reaction was stopped by the addition of 20 μl of 10× Stopping buffer (100 mM Tris-Hcl, pH 8, 25 mM $MgCl_2$, 100 mM NaCl, 20 mM GTP. The sample was then immunoprecipitated with anti-PS-1 loop monoclonal antibody (5 μl). The antibody-protein complex was subjected to binding to Protein A/G agarose for 90 min at RT and washed twice with washing buffer 1 (50 mM HEPES, pH 7.4, 1 mM EDTA, pH 8.0, 1% Triton X-100 1X protease inhibitor mix, 150 mM NaCl and 60 mM octyl-8-D-glucopyranoside), and once with each of washing buffers 2 (50 mM HEPES, pH 7.4, 1 mM EDTA, pH 8.0, 0.5% Triton X-100, 1× protease inhibitor mix and 50 mM NaCl) and 3 (50 mM HEPES, pH 7.4, 1 mM EDTA, pH 8.0 and 1× protease inhibitor mix. The washed agarose beads were then suspended in scintillation fluid (CytoScint, ICN) (5 ml) and counted in a Beckman Coulter LS 6000 SC scintillation counter for 3 min.

When 100 μg of extract of ES (PS-1$^{-/-}$/PS-2$^{-/-}$) cells co-transfected with cDNAs for full-length human PS-1 and the G-protein $G\alpha_{oA}$ or $G\alpha_{oB}$ were immunoprecipitated with MAb to the large hydrophilic loop of PS-1, followed by Western blot hybridization with affinity purified polyclonal antibody to $G_o$ (which recognizes both isoforms, $G_{oA}$ and $G_{oB}$), only the PS-1/$G_{oA}$ co-transfected cells gave a robust signal for $G_o$ at ~45 kDa (FIG. 1, lane 3), suggesting that $G_{oA}$, but not $G_{oB}$, binds to PS-1. Control untransfected cells or cells transfected with PS-1 alone did not show a $G_o$ band on Western blots when treated identically (FIG. 1).

Verification of the binding of G-protein $G_o$ to the cytoplasmic carboxyl terminus of PS-1. A tail-less construct of PS-1 was made in pcDNA3 in which only the cytoplasmic domain of PS-1 immediately following the last TM-domain is deleted (this construct comprises amino acids 1-430). This construct was used to transfect ES (PS-1$^{-/-}$/PS-2$^{-/-}$) cells. Tail-less PS-1 has been shown to integrate into the membrane and to be expressed at the cell surface. In an identical strategy to the one described above for full-length PS-1, ES (PS-1$^{-/-}$/PS-2$^{-/-}$) cells were transfected with cDNAs for tail-less PS-1 and the G-proteins $G_{oA}$ or $G_{oB}$. Cells extracts were then subjected to immunoprecipitation with PS-1 loop MAb #5232), separated on SDS PAGE and Western blotted with antibodies to $G_o$.

100 μg of extract of ES (PS-1$^{-/-}$/PS-2$^{-/-}$) cells co-transfected with cDNAs for tail-less PS-1 and the G-protein $G\alpha_{oA}$ or $G\alpha_{oB}$ were immunoprecipitated with MAb to the large hydrophilic loop of PS-1, followed by Western blot hybridization with affinity purified polyclonal antibody to $G_o$ (recognizes both isoforms, $G_{oA}$ and $G_{oB}$). Binding was detected (FIG. 1, lane 6) indicating that the carboxyl terminal 39 amino acids earlier identified to be the binding domain did not constitute the entire binding domain of PS-1 for $G_{oA}$. $G_{oB}$ showed no binding to tail-less PS-1 (FIG. 1, lane 7).

The results using the tail-less construct, which eliminated the major part of $G_{oA}$ binding to PS-1, show specificity for some PS-1:$G_{oA}$ binding to another region of PS-1 besides the PS-1 tail. They also rule out the possibility that $G_{oA}$ may have bound to other components of the PS-1 β-secretase complex, that may have co-immunoprecipitated with the PS-1 antibody.

Figure 3:
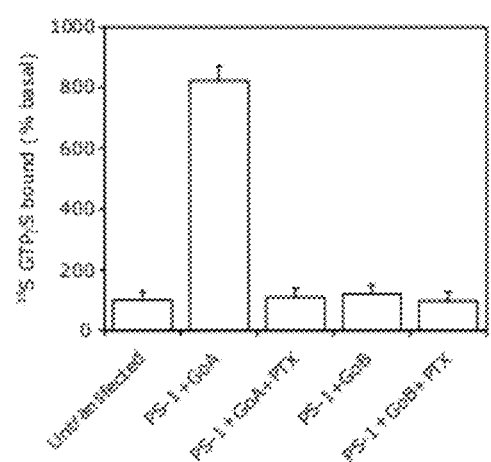
FIG. 3 involves an independent way of demonstrating $G_{oA}$ binding to PS-1. [$^{35}$S]-GTPγS, an analog of GTP, makes a covalent bond to the active site of a G-protein that is blocked by a prior reaction with Pertussis toxin (PTx). In column 2, there is shown an 8-fold increase in $^{35}$S-incorporation into $G_{oA}$ that is immunoprecipitated with antibody to PS-1, but not into $G_{oB}$ (lane 4). Therefore, PS-1 binds to $G_{oA}$ (that has reacted with [$^{35}$S]-GTPγS to identify it as a G-protein (column 2), but also to a lesser extent to $G_{oB}$ than to $G_{oA}$ (column 4). The $^{35}$S bindings to $G_{oA}$ and $G_{oB}$ are blocked by prior treatment with PTx (column 3 and 5).

Additional studies were performed to elucidate the binding of G-protein $G_o$ to intact PS-2. The 39 amino acid PS-1 C-terminal region identified to be the binding domain is completely conserved in the C-terminal tail of PS-2. Accordingly, it was believed that the C-terminal domain of PS-2 would also bind $G\alpha_o$. As with PS-1, $G_o$ was shown to bind to PS-2, but with distinct differences. The $G_o$ antibody, which recognizes both $G_{oA}$ and $G_{oB}$, showed a doublet on Western blots of PS-2 immunoprecipitates of extracts of cells co-transfected with PS-2 and $G_{oA}$ as well as PS-2 and $G_{oB}$ cDNAs. The doublet presumably represents binding of both isoforms of $G_o$ to PS-2 (FIG. 3, lanes 2 and 4). In contrast, PS-1 did not bind to $G_{oB}$ (FIG. 1, lane 4) and only showed a single band on Western blots with the same $G_o$ antibody (FIG. 1, lane 3).

Figure 2:
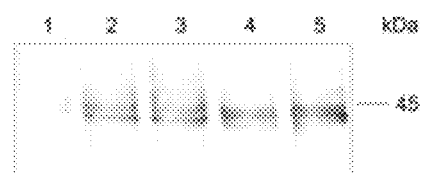
FIG. 2 shows a Western blot of a similar experiment to that of FIG. 1 but with PS-2 instead of PS-1. Lanes 2 and 4 show that tail-less PS-2, unlike tail-less PS-1, still binds $G_{oA}$ (and $G_{oB}$), and therefore that the binding sites for $G_{oA}$ and $G_{oB}$ are not confined to the C-terminal domain of PS-2, as is the case for PS-1 (FIG. 1) Lane 1 is untransfected ES (PS-1$^{-/-}$/PS-2$^{-/-}$). Lane 2 is PS-2+$G_{oA}$. Lane 3 is Tail-less PS-2+$G_{oA}$. Lane 4 is PS-2+$G_{oB}$. Lane 5 is Tail-less PS-2+$G_{oB}$.

The binding of G-protein $G_o$ to the cytoplasmic carboxyl terminus of PS-2 was investigated. As for PS-1, a tail-less construct of PS-2 was made in pcDNA3 in which only the cytoplasmic domain of PS-2 immediately following the last TM-domain was deleted (this construct comprised amino acids amino acids 1-410). This construct was used to transfect ES (PS-1$^{-/-}$/PS-2$^{-/-}$) cells and has been shown to integrate into the membrane and be expressed at the cell surface (FIG. 2). In an identical strategy to the one described above for full-length PS-1 and PS-2, ES (PS-1$^{-/-}$/PS-2$^{-/-}$) cells were transfected with cDNAs for tail-less PS-2 and the G-proteins $G_{oA}$ and $G_{oB}$. Cells extracts were then subjected to immunoprecipitation with PS-2 loop Mab #MA1-754), separated on SDS PAGE and Western blotted with antibodies to $G_o$.

When tail-less PS-2, co-expressed with $G_{oA}$ was immunoprecipitated with PS-2 MAb and Western blotted with anti $G_o$ antibody, as with results for PS-1, there was a decrease in band intensity, but the band was not totally absent. The intensity of the bands in the $G_{oB}$/PS-2 co-transfection sample, on the other hand, was unaltered for the tail-less sample suggesting that $G_{oB}$ binds PS-2 at an intracellular domain other than the carboxyl terminal tail FIG. 3, lanes 3 and 5). Therefore, PS-1 and PS-2 are discriminated not only by the $G_o$ isoforms that they bind to, but also the binding sites on the PS-1 and PS-2 that are not homologous to one another. It seems likely, therefore, that functional studies of PS-1 and PS-2 will give quite different results; i.e., PS-1 and PS-2 are not merely functionally redundant proteins.

Additional studies of PS mediated functional activation of $G\alpha_{oA}$ and $G\alpha_{oB}$ PS-1 and the G-proteins $G_{oA}$ and $G_{oB}$ were performed. Previous studies used GTP hydrolysis and GTPγS binding as one of several independent approaches to evaluate $G_o$ binding to the carboxyl terminus of PS-1. However, they carried out this assay with a synthesized peptide of residues 429-467 in the C-terminus of PS-1, along with three control peptides. The approach on the other hand was to evaluate the functional consequences of the binding of the G-proteins $G_{oA}$ and $G_{oB}$ to intact PS-1 and PS-2 in the co-transfected cell, by assaying for 35S-GTPγS incorporation in cell extracts.

Figure 4:
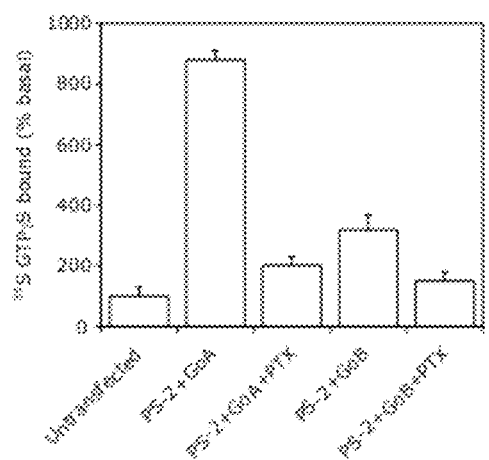
FIG. 4 is a graph depicting $^{35}$SGTPγS incorporation in extracts of ES cells transfected with cDNA for PS-2 and G-protein $G_{oA}$.

The $^{35}$S-GTPγS incorporation in extracts of ES cells that were co-transfected with cDNAs for PS-1 and the G-protein $G_{oA}$ was shown to be over 700% the value obtained for control untransfected ES (PS$^{-/-}$) cells (FIG. 4, lane 2). This increase was not seen when cells transfected with PS-1 and G$_{oA}$ cDNAs were first treated with PTx (FIG. 4, lane 3) showing an inhibition of function in the presence of the toxin. Cells transfected with cDNAs for PS-1 and G$_{oB}$ on the other hand did not show incorporation of $^{35}$S-GTPγS (FIG. 4 lane 4), consistent with previous results of a lack of binding of G$_{oB}$ to PS-1.

As with PS-1, PS-2 when co-expressed with G$_{oA}$ and assayed for $^{35}$S-GTPγS binding showed greater than 700% increase in S-GTPγS binding over untransfected control ES (PS$^{-/-}$) extracts (FIG. 4, lane 2). This was inhibited in the presence of PTx (FIG. 4, lane 3). Unlike the case for PS-1, G$_{oB}$ binding to PS-2 does give an increase in $^{35}$S-GTPγS incorporation. This novel finding is consistent with other data provided herein indicating that G$_{oB}$ binds to PS-2 but not PS-1. The increase in $^{35}$S-GTPγS incorporation is less than that observed for G$_{oA}$ (~300%) (FIG. 4, lane 4). This increase is inhibited in the presence of PTx. The results shown in FIG. 4 are representative of at least 3 independent experiments.

Example 2

ES PS double-null cells were cultured and plated overnight. The cells were transfected with a pcDNA3 construct of full-length human β-APP cDNA using lipofectamine (Invitrogen) according to the manufacturer's protocols. DAMI cells were cultured and transfected either with pcDNA3 or with a pcDNA3 construct of full-length human PS-1 or PS-2 cDNA.

Affinity-purified polyclonal rabbit anti-PTyr antibodies (Maher et al., 1985) were used in Western blots. A mouse monoclonal anti-PTyr antibody (4G10; Upstate Biotechnology, Lake Placid, N.Y.) was used in ELISA analyses. Mouse monoclonal antibody to human pp60c-src (Anti-Src, clone GD11) and rabbit polyclonal antibody to Lyn (Anti-Lyn) were purchased from Upstate Biotechnology. Rabbit polyclonal antibody to Fyn (Anti-Fyn, sc-16) was purchased from Santa Cruz Biotechnology, Santa Cruz, Calif. Primary rat anti-human PS-1 monoclonal antibody MAb #1563 directed to the N-terminal domain of PS-1 was purchased from Chemicon International, Temecula, Calif. It was raised to a fusion protein antigen containing part of the N-terminal domain of human PS-1 (residues 21-80) fused to GST. Primary mouse monoclonal antibody MAb #348 to the human β-APP extracellular domain was purchased from Chemicon International.

Fluorescein isothiocyanate (FITC)-conjugated affinity purified goat anti-rat IgG and tetramethylrhodamine B isothiocyanate (TRITC)-conjugated affinity purified donkey anti-mouse IgG secondary antibodies were purchased from Jackson ImmunoResearch, West Grove, Pa. Immunofluorescence labeling Transfected and untransfected DAMI cells were fixed with 4% paraformaldehyde in PBS for 10 mins and used without permeabilization. Cells were labeled in suspension with antisera to PS-1 (1:200 dilution), and β-APP (1:500 dilution) in PBS containing 1% BSA for 30 min at room temperature. After washing with PBS three times by centrifugation, the cells were resuspended in 1% BSA/PBS and incubated with appropriate fluorescent secondary antibodies. Incubation was carried out at room temperature for 20 min, after which the cells were washed with PBS and mounted onto slides in the presence of mounting medium (Vector Laboratories, Burlingame, Calif.).

Immunofluorescent microscopy was performed using oil immersion with a X60 objective lens. The slides were viewed using fluorescein isothiocyanate and tetramethylrhodamine β isothiocyanate filters and a Zeiss Photoscope III instrument, or with Nomarski optics.

N-terminal domains of PS-1 and PS-2 were obtained by PCR and cloned into the Tth 1111 and Xho-1 sites of the FLAG expression vector (Scientific Imaging Systems, IBI 13100) to produce a fusion protein with FLAG attached at the N-terminus of either the PS-1- or 2 N-terminal domains. The two FLAG-fusion proteins were grown separately in DH5α bacteria and affinity purified according to the manufacturer's protocols. The purified recombinant proteins were checked by Western blots using antibodies to both FLAG and either the N-terminal domain of PS-1 or PS-2.

DAMI:ES cells: Equal numbers (0.5×10$^6$/ml) of β-APP 695 (Selkoe and Podlisny, 2002)-transfected ES double-null cells and PS-1 transfected DAMI cells were co-cultured at 37° C. for various times between 0-20 mins.

All experiments after those in FIG. 7 (with the exception of FIG. 9a, Panel 4) were carried out with appropriately transfected DAMI cells only. Equal numbers (0.5×10$^6$/ml) of β-APP-transfected DAMI cells and either PS-1- or PS-2-transfected DAMI cells were mixed gently at room temperature, exactly as described (Dewji and Singer, 1998). In control experiments, DAMI cells transfected with pcDNA3 alone were substituted for the β-APP transfected cells.

At several times between 0 and 20 min after mixing, an aliquot of each cell mixture was rapidly centrifuged, the culture medium was removed, and the cell pellet was suspended in 200 μl of extraction buffer (50 mM Tris, pH 8.0/150 mM NaCl/0.5% Nonidet-P40) containing protease inhibitors (1 mM 4-(2-aminoethyl) benzene sulfonyl fluoride hydrochloride (AEBSF)/1 μg/ml antipain/0.1 μg/ml pepstatin A/0.1 μg/ml leupeptin) and the phosphatase inhibitor sodium orthovanadate (0.1 mM). The mixture was sonicated with three bursts of 20 sec duration and then centrifuged. These extract supernatants were then used for Western blot and ELISA analyses as described below.

Assays for Src family of protein tyrosine kinases in cell extracts were performed. The substrate peptide {[Lys19] cdc2 (6-20)-NH2} and control peptides {[Lys19Ser14Val12] cdc2 (6-20)} and {[Lys19Phe15]cdc2(6-20)} were purchased from Upstate Biotechnology Inc. Src kinase activity was measured in extracts of transfected DAMI cells (either β-APP- or pcDNA3-transfected) mixed with PS-1-transfected cells; and with β-APP— or pcDNA3-transfected cells mixed with PS-2-transfected cells, using all three peptides. Controls included experiments carried out using no substrate in the reaction mixture.

The substrate peptide (1.5 mM in 10 μl), Src kinase reaction buffer (100 mM Tris-HCl, pH 7.2, 125 mM MgCl$_2$, 25 mM MnCl$_2$, 2 mM EGTA, 0.25 mM sodium orthovanadate, 2 mM DTT) (10 μl), Src kinase (2-20 U of purified enzyme per assay or 10-200 μg protein lysate in 10 μl and [γ-$^{32}$P]ATP (NEN Dupont, Boston, Mass.) diluted with Mn$^{2+}$/ATP cocktail (10 μl), were incubated for 15-20 min at 30° C.

Aliquots of the extract supernatants described above (100 μg protein/lane) were boiled for 5 min in loading buffer (50 mM Tris, pH 6.8, 0.1 M DTT, 2% SDS, 0.1% bromophenol blue, 10% glycerol), separated electrophoretically on SDS-PAGE (10%) gels, and the proteins transferred onto nitrocellulose filters. Filters were incubated with the primary polyclonal rabbit anti-PTyr antibodies followed by the horse radish peroxidase-conjugated goat anti-rabbit IgG. Filter-bound peroxidase activity was detected by chemiluminescence.

Cell lysates were prepared in extraction buffer and clarified by micro-centrifugation at 4° C. for 15 mins.

Extracts were incubated with 4 µg antibodies specific for either c-Src, Lyn or Fyn followed by protein-A or G sepharose (40 µl of slurry). The antigen antibody-protein-A (or -G) sepharose complex was washed three times in RIPA (50 mM Tris-HCl, pH 7.2, 150 mM NaCl, 1% Triton X-100, 1% Na deoxycholate, 0.1% SDS, 1% trasylol, 25 µM leupeptin) containing 300 mM NaCl, once with RIPA containing 10 mM NaCl, twice with 40 mM Tris-HCl, pH 7.2 and once with kinase buffer containing 25 mM HEPES, pH 6.9, 3 mM $MnCl_2$ and 200 µM sodium orthovanadate.

Reactions were performed according to published protocols (Zisch et al., 1998) in 40 µl kinase buffer (25 mM Hepes, pH 6.9, 3 mM $MnCl_2$ and 200 µM sodium orthovanadate) containing 5 µCi [g32P] ATP (3000Ci/mmol) for 30 min at 37° C. The reaction beads were washed three times with kinase buffer and resuspended in 75 µl SDS gel loading buffer (250 mM Tris-HCl, pH 6.8, 4% SDS, 10% 2-mercaptoethanol, 0.02% bromophenol blue and 75% glycerol). Autophosphorylation reactions were subjected to SDS-PAGE followed by transfer of proteins onto PVDF membranes and autoradiography.

ELISAs Protein tyrosine kinase activity was measured by an Enzyme Linked Immunosorbent Assay (ELISA) using a tyrosine kinase assay kit (Upstate Biotechnology). A biotinylated substrate peptide containing tandem repeats of Poly (Glu4-Tyr) was incubated with supernatants of extracts of transfected cells mixed for different times (20 µg protein/well) in the presence of non-radioactive ATP and a $Mn^{2+}/Mg^{2+}$ co-factor cocktail according to the manufacturer's protocols. A phosphotyrosine specific mouse monoclonal antibody (4G10) conjugated to horseradish peroxidase was used to detect the phosphorylated substrate by ELISA.

Absence of cell surface expression of β-APP in untransfected and PS-1-transfected DAMI cells. Because the initial set of studies depends on the proposition that DAMI cells, after transfection with PS-1, continue to express only negligible amounts of β-APP on their surface, the following experiments were first carried out. Both untransfected and PS-1-transfected DAMI cells in the fixed but impermeable state were doubly immunofluorescently labeled for β-APP and PS-1. Untransfected fixed impermeable DAMI cells, as previously shown (Querfurth and Selkoe, 1994), do not express significant amounts of β-APP at the cell surface (FIG. 6a, Panel 2), whereas DAMI cells transfected with a pcDNA3 construct of β-APP show substantial cell-surface expression in fixed impermeable cells (FIG. 5b, Panel 2). FIGS. 6a and b, Panels 1 show, however, that untransfected fixed impermeable DAMI cells do express endogenous cell-surface PS-1. In FIG. 5c, Panel 1, this cell-surface expression of PS-1 is increased in fixed impermeable PS-1-transfected cells. FIG. 5c, Panel 2, shows that transfecting DAMI cells with PS-1 does not significantly increase the cell-surface expression of β-APP over the negligible levels seen in untransfected cells (FIG. 5a, Panel 2). FIG. 2d, Panel 2, shows cell-surface expression of β-APP in ES double-null fixed impermeable cells transfected with β-APP, but not PS-1 expression (FIG. 5d, Panel 1).

With untransfected, fixed impermeable ES double-null cells, there is, as expected, no labeling for cell-surface PS-1 (FIG. 5e, Panel 1), but a small amount of surface expression of endogenous β-APP (FIG. 5e, Panel 2). These results confirm that in interactions of β-APP-transfected ES double-null cells and PS-transfected DAMI cells, only the ES cells express cell-surface f3-APP, and no PS; while only the PS-transfected DAMI cells express PS, and no β-APP, at the cell-surface. If a β-APP:PS interaction occurs after cell mixing, it can therefore only be the result of a cell-cell interaction.

Also provided herein are data indicating that specific β-APP:PS intercellular signaling results in an increase in tyrosine kinase activity. ES double-null cells transfected with β-APP were mixed with DAMI cells transfected with PS-1, and were co-cultured for various times between 0-20 min, using cell densities that ensured cell-cell contact. ELISA assays were then carried out on cell extracts to measure protein tyrosine kinase activity. FIG. 6a shows that these co-cultures produced a rapid and transient increase in protein tyrosine kinase activity similar in extent and kinetics to those previously described when PS-1-transfected DAMI cells were mixed with β-APP-transfected DAMI cells (Dewji and Singer, 1998). When the same interaction as in FIG. 6a was carried out in the presence of 25 µg of purified baculovirus-derived soluble β-APP (extra-cellular domain of β-APP) (FIG. 6b) or 25 µg of fusion peptide of the FLAG reporter fused to the N-terminal domain of PS-1 (FIG. 6c), no increase in protein tyrosine kinase activity resulted. On the other hand, the same β-APP:PS-1 co-cultures in the presence 25 µg of FLAG-PS-2 N-terminal domain fusion peptide did not inhibit PTyr formation (FIG. 2d). These results clearly establish several points: 1) Soluble β-APP itself does not activate the PS-1-transfected DAMI cells to exhibit tyrosine kinase activity; the intact β-APP in the transfected ES cell membrane is required. On the contrary, the soluble β-APP inhibits the activity produced by the membrane-bound β-APP, demonstrating that membrane-bound β-APP is specifically involved in the activation; 2) the N-terminal domain of PS-1 is itself incapable of activating the β-APP-transfected cell to exhibit tyrosine kinase activity. The intact PS-1 molecule in its DAMI cell membrane is required. But the N-terminal domain of PS-1 (but not PS-2) inhibits the activation of the co-culture, showing that membrane-bound PS-1 on the PS-1-transfected DAMI cell is also specifically involved in the interaction; 3) The protein nature of the inhibitors, soluble β-APP and the FLAG-fusion protein of the N-terminal domain of PS-1, assures their impenetrability of the cell membranes of living DAMI and ES cells, and therefore demonstrates that it is only the exterior domains of the cell-surface β-APP and PS-1 that are involved in generating the signaling event (i.e., the signaling is of the juxtacrine type). These results provide compelling evidence that establish that a juxtacrine interaction between β-APP and PS can occur.

Furthermore, this demonstration that the N-terminal domain of PS-1 is exposed at the extracellular surface is consistent with the 7-TM topography of the PS proteins, but is contrary to the prediction of the 8-TM model, which positions the N-terminal domain of PS intra-cellularly.

Additional data provided herein indicate that β-APP:PS-1 and β-APP:PS-2 intercellular signaling can be mediated by members of the Src family of tyrosine kinases. The increases in PTyr modification that are a consequence of β-APP:PS intercellular binding involved one or more protein tyrosine kinases that need to be identified. Since neither β-APP nor the PS proteins contain such a kinase active site, an indirect activity of the cytoplasmic domains of these proteins, such as the direct or indirect binding of a cytoplasmic tyrosine kinase to one of these domains, may be involved in the downstream signal. Since several cytoplasmic tyrosine kinases have been identified within the Src gene family, Src family protein tyrosine kinases were assayed in cell extracts of mixed transfected cells using the substrate peptide [lys19]cdc2(6-20)-$NH_2$ (KVEKIGTYGVVKK; SEQ ID NO:12). This peptide, with Tyr 19 in cdc2(6-20) replaced by lys, has been shown to be an efficient substrate for the Src family kinases. All Src family kinases tested, including v-Src and c-Src, c-Yes, Lck, Lyn and Fyn, demonstrate strong activity towards this substrate. Two control peptides were also used: In the first peptide, [lys19ser14val12]cdc2(6-20)NH$_2$ (KVEKIGVGSYGVVKK; SEQ ID NO:13), glu12 and thr14 were replaced by val and ser, respectively, causing a significant decrease in efficiency of the resulting peptide to serve as a substrate for the Src family tyrosine kinases. The other peptide, [lys19phe15]cdc2(6-20)NH2 (KVEKIGEGTFGVVKK; SEQ ID NO:14) should not be phosphorylated by tyrosine kinases but did contain a potential target for ser/thr kinases (thr 14).

The results of Src family kinase activity measurements in extracts of co-cultures of β-APP-transfected DAMI cells with PS-1-transfected DAMI cells evoking β-APP:PS-1 interactions, and for the corresponding control lacking β-APP (pcDNA3:PS-1), are shown in FIG. 7a and b. Similar results for transfected DAMI cell mixtures evoking β-APP:PS-2 interactions, and extracts of control pcDNA3:PS-2 mixed transfected DAMI cells, using these three peptides are shown in FIG. 7c and d. For each β-APP:PS cell mixture, where [lys19]cdc2(6-20)NH2 was used as the Src family kinase substrate, the temporal course of increased activity compared to control peptides were obtained that paralleled ELISA results for tyrosine kinase activity. For the β-APP:PS-1 interaction (FIG. 7a), Src family kinase activity peaked at 8 minutes and returned to baseline levels by 12 minutes confirming previous ELISA results for tyrosine kinase activity as a function of time after cell mixing. No significant increase could be observed when the same substrate was used for the control pcDNA3:PS-1 (FIG. 7b) mixed cells. For the cell mixtures evoking β-APP:PS-2 interactions (FIG. 7c), as for the tyrosine kinase ELISA results, two clear peaks of activity were observed with substrate peptide [lys19]cdc2(6-20)NH$_2$, at 9 and 16 minutes after mixing.

For the corresponding control lacking β-APP, pcDNA3:PS-2 (FIG. 7d), no significant increases of Src kinase activity over background were observed. These results suggest that the increases in tyrosine kinase activity previously observed for β-APP- with PS-1-transfected cell mixtures, or β-APP- with PS-2-transfected cell mixtures, involve one or more members of the Src tyrosine kinase family.

Figure 8:
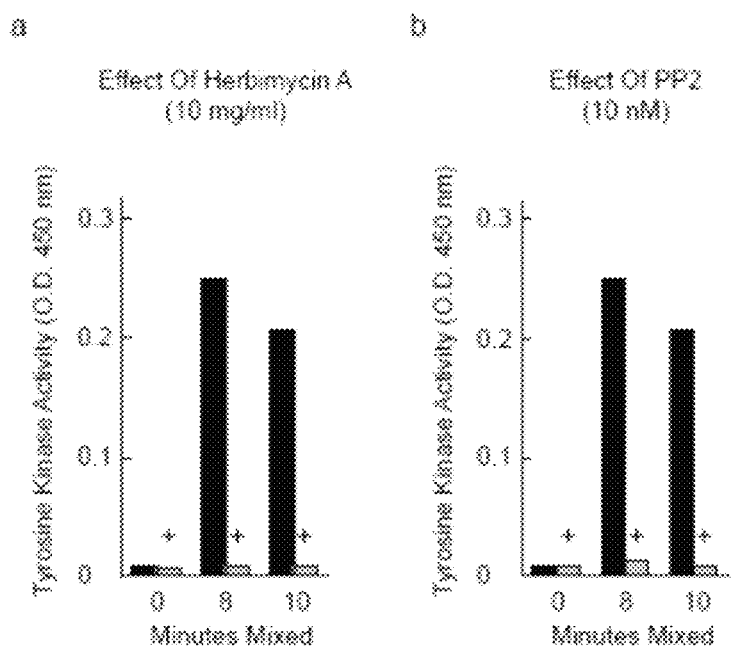
FIG. 8A-B shows inhibition of tyrosine kinase activity. ELISAs to demonstrate tyrosine kinase activity of DAMI cells which had been separately transfected with β-APP and PS-1 and mixed in the presence and absence of 10 μg/ml Herbimycin A (a) and 10 nM PP2 (b), as a function of time after mixing.

Inhibition of tyrosine kinase activity in the presence of specific inhibitors of Src family kinases and tyrosine kinase. The involvement of the Src kinase family in β-APP:PS intercellular signaling was further confirmed with ELISAs of extracts of β-APP:PS-1 mixed cell interactions carried out in the presence or absence of specific inhibitors of tyrosine kinase (herbimycin A) and Src family kinases (PP2). FIG. 8a demonstrates that in the presence of 10 μg/ml herbimycin A, the increase in tyrosine kinase activity at 8-10 mins after mixing β-APP-transfected DAMI cells with PS-1-transfected DAMI cells is completely inhibited. The same experiment carried out in the presence of 10 nM PP2 (FIG. 8b) similarly showed the inhibition of tyrosine kinase activity.

Additional data related to the involvement of c-Src in β-APP:PS-1 intercellular signaling is provided below. In order to determine the identity of the Src family member(s) involved in the β-APP:PS-1 intercellular signaling, we began by investigating pp60c-Src. Two main protein bands of apparent molecular weights 58 and 60 kDa, a doublet similar in size to c-Src, underwent transient PTyr modification in this juxtacrine interaction. When extracts of mixtures of PS-1-transfected DAMI cells with β-APP-transfected DAMI cells were subjected to SDS16 PAGE and immunoblotting with either anti-PTyr or anti-c-Src antibodies, both antibodies reacted with the same two bands (FIG. 9a, Panels 1-3). Panel 1 of this figure immunoblotted with anti-PTyr antibodies shows transient increases in tyrosine phosphorylation of the protein bands with a maximum at 8-10 mins after cell mixing. In Panel 2 the same extracts immunoblotted with the c-Src antibody show no variation with time, indicating that the c-Src protein concentration remains unchanged during the increase in its PTyr levels. An important observation was that when ES double-null cells transfected with β-APP (therefore expressing only β-APP, but no PS-1 or 2) were mixed with DAMI cells transfected with PS-1 (therefore expressing only PS-1, but no cell surface β-APP), the p60 c-Src proteins plus one or two additional proteins underwent transient increases in PTyr modification at similar times after mixing (FIG. 9a, Panel 4) that were seen with the β-APP-transfected DAMI cells mixed with PS-1-transfected DAMI cells (FIG. 9a, Panel 1). The PTyr modification results were therefore associated with PS-1 and not the cell type that expressed it (see below for PS-2).

In order to test further whether c-Src was the member of the tyrosine kinase family that underwent transient tyrosine phosphorylation in the β-APP:PS-1 interaction, experiments were carried out (autophosphorylation) in which the extracts of the mixed transfected DAMI cells taken at different times after mixing were treated with anti-c-src antibodies, followed by protein-G sepharose beads. To the beads was then added $\gamma^{32}$PATP; subsequently the proteins were solubilized from the beads, and subjected to SDS17 PAGE and autoradiography. The results in FIG. 9b demonstrate that several transient bands appear that are maximally phosphorylated at 8-10 min after cell mixing, a time course corresponding to the appearance of PTyr in the analogous extracts (FIG. 9a, Panel 1). Prominent among these bands is one doublet corresponding to c-Src, confirming that c-Src is activated transiently in the β-APP:PS-1 intercellular interaction.

The identities of the other phosphorylated bands in FIG. 9b are not known. Not all of them are necessarily due to tyrosine phosphorylation; some serine or threonine kinases might have been bound to the c-Src that was immuno-reacted with specific anti-pc-Src. Involvement of Lyn but not Fyn downstream of β-APP:PS-2 intercellular signaling. When β-APP:PS-2 intercellular interactions were carried out with mixtures of appropriately transfected DAMI cells, an entirely different set of proteins was PTyr modified than for the β-APP:PS-1 system. Although bands were detected by the PTyr antibody that were present at 50-66 kDa, these did not correspond to c-Src on Western blots (FIG. 11a, Panel 1). Furthermore, when extracts of β-APP:PS-2 mixed cells were first immunoprecipitated with c-Src antibodies and the immunoprecipitates were then autophosphorylated in vitro, no significant increases in phosphorylation at the earlier time points (8-10 mins after mixing) were seen (FIG. 10b).

At later time points however, c-Src could apparently be phosphorylated in these samples indicating that it contributes to increases identified in the second later peak of β-APP:PS-2 signaling (FIG. 10b). The possible involvement of other members of the Src kinase family was investigated with molecular weights in the 53-59 kDa range other than c-Src. Lyn (Mwt 53/56 kDa) and Fyn (Mwt 59 kDa) were two candidate Src kinases that were examined.

Results of Western blot hybridization with anti-Lyn antibodies in FIG. 11a show that Lyn protein concentrations do not change when β-APP:PS-2 intercellular interactions are carried out, but after immunoprecipitation of the extracts with anti-Lyn antibodies and in vitro autophosphorylation of the precipitates, a transient phosphorylation of Lyn with peaks of activity at 8-9 and 17-18 min is observed, along with other phosphorylated bands (FIG. 11c). Lyn undergoes transient phosphorylation in a pattern that is similar to the PTyr increases seen on Western blots and ELISAs for β-APP:PS-2 interaction (FIG. 11c). Fyn, on the other hand, shows no autophosphorylation in-vitro in the same extracts after immunoprecipitation with anti-Fyn antibodies (FIG. 11d), nor any change in its concentration with time (FIG. 11b).

Example 3

The following data demonstrates G-protein binding to endogenous PS-1 and PS-2 in extracts of mouse frontal cortex. A 20% homogenate of WT mouse frontal was made in GTPγS solubilization/extraction buffer [50 mM HEPES/NaOH pH 7.4, 1 mM EDTA, 1 mM DTT, 1% Triton-X100, 60 mM octylglycoside, 1× Protease inhibitor mix (1 uM phenylmethylsulfonylflouride, 1 ug/mL antipain, 0.1 ug/mL pepstatin A, 0.1 ug/mL leupeptin)]. Measurements of [$^{35}$S]GTPγS binding were performed on Untreated, PTX treated; and PS-1 and PS-2 immuno-depleted extracts.

For untreated samples, 100 µg of extract was brought up to 100 uL in GTPγS solubilization/extraction buffer and mixed with an equal volume of GTPγS Buffer B (50 mM HEPES/NaOH pH 7.4, 40 µM GDP, 50 mM MgCl$_2$, 100 mM NaCl) for a total volume of 200 µL. The reaction was started with 50 nM [$^{35}$S] GTPγS (1250 Ci/mMol; Perkin Elmer) and incubated at RT for 60 min. The reaction was stopped by addition of 20 uL 10× Stopping buffer (100 mM Tris-HCl, pH 8.0, 25 mM MgCl$_2$, 100 mM NaCl, 20 mM GTP).

For PTX treated samples, 100 µg of extract was brought up to 100 µL in GTPγS solubilization/extraction buffer and treated with 500 ng/mL activated PTX in the presence of PTX Buffer (20 mM HEPES pH 8.0, 1 mM EDTA, 2 mM MgCl$_2$, 1 mM NAD). The sample was incubated for 12 hrs at 30° C. The PTX treated sample was then mixed with an equal volume of GTPγS Buffer B and taken through [$^{35}$S]GTPγS assay as described above.

Extracts of mouse frontal cortex were immunoprecipitated with a mixture of polyclonal antibodies to PS-1 and PS-2 (10 uL each) at 4° C. overnight to deplete the samples of PS-1 and PS-2. Protein A agarose (20 uL slurry/100 µg protein) was added and samples were and shaken end-over-end at 4° C. for 2 h. The PS-antibody-protein A complex was centrifuged at high speed for 5 min. Supernatant was recovered in and 100 µg aliquots were taken through the [$^{35}$S] GTPγS assay as described.

Following the GTPγS reaction, 5 uL of either anti-PS-1 or anti-PS-2 monoclonal antibodies were added and samples were placed at 4° C. overnight. The antibody-protein complex was bound to 20 µL Protein A/G agarose (Pharmacia) and samples were placed at 4° C. and shaken end-over-end for 2 hrs. The agarose beads were washed three times with Wash Buffer 1 (50 mM HEPES, pH 7.4, 1 mM EDTA, pH 8.0, 1% Triton-X100, 1× protease inhibitor mix) and once with each Wash Buffer 2(50 mM HEPES, pH 7.4, 1 mM EDTA, pH 8.0, 0.5% Triton-X100, 1× protease inhibitor mix) and 3(50 mM HEPES, pH 7.4, 1 mM EDTA, pH 8.0, 1× protease inhibitor mix). The washed agarose beads were then suspended in 5 mLs scintillation fluid (CytoScint, ICN) and counted on a Beckman Coulter LS 6000 SC scintillation counter for 3 min.

Figure 12:
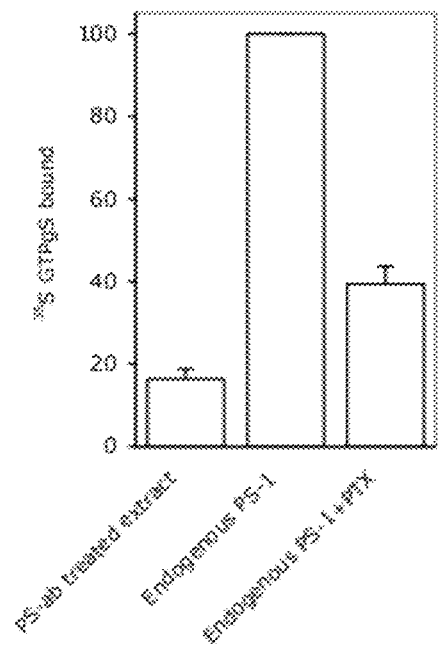
FIG. 12 shows the $^{35}$S-GTPγS incorporation in extracts of mouse brain that could be immunoprecipitated with monoclonal antibodies to PS-1.

FIG. 12 shows the $^{35}$S-GTPγS incorporation in extracts of mouse brain that could be immunoprecipitated with monoclonal antibodies to PS-1, suggesting the co-precipitation of $^{35}$S-GTPγS-bound G-protein with the endogenous PS-1. This incorporation was greater than 80% of that found for extracts which had been prior depleted of PS-1 and PS-2 by treatment with polyclonal antibodies to the two PS proteins, showing specificity of the G-protein:PS-1 binding. Treatment with PTx inhibited the $^{35}$S-GTPγS incorporation by 60%.

Figure 13:
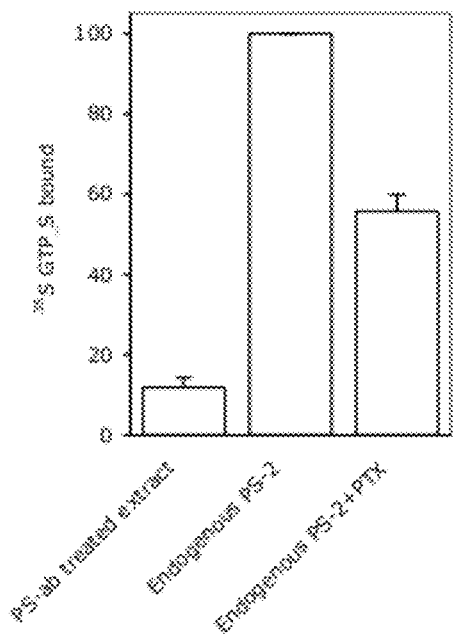
FIG. 13 shows the $^{35}$S-GTPγS incorporation in extracts of mouse brain that could be immunoprecipitated with monoclonal antibodies to PS-2.

FIG. 13 shows the $^{35}$S-GTPγS incorporation in extracts of mouse brain that could be immunoprecipitated with monoclonal antibodies to PS-2, suggesting the co-precipitation of $^{35}$S-GTPγS-bound G-protein with the endogenous PS-2. This incorporation was greater than 85% of that found for extracts which had been prior depleted of PS-1 and PS-2 by treatment with polyclonal antibodies to the two PS proteins, showing specificity of the G-protein:PS-2 binding. Treatment with PTx inhibited the $^{35}$S-GTPγS incorporation by 55%. These results demonstrate a specific PTx-sensitive G-protein coupling to endogenous mouse brain PS-1 and PS-2.

Figure 14:
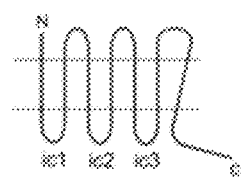
FIG. 14 illustrates intracellular domains of PS.

Sequences corresponding to the first 16 amino acids of intracellular loop 1 [ic1(1-16)], the remaining 16 amino acids of intracellular loop 1 [ic1(17-32)], the entire intracellular loop 2 (ic2), the entire intra-cellular loop 3 (ic3), the first 20 amino acids of the cytoplasmic C-terminal tail (C1-20) and the remaining 19 amino acids of the cytoplasmic C-terminal tail (C21-39) for both PS-1 and PS-2 will be synthesized and HPLC purified to >90% purity. FIG. 14 illustrates intracellular domains of PS. Table 1 shows the sequences that can be synthesized from these domains. In addition, a 20 amino acid control peptide synthesized in which the sequences of peptide C1-20 can be scrambled. This peptide is part of the 39 amino-acid sequence identified as the binding domain on PS-1 for G$_o$.

TABLE 1

| PS-1 Cytoplasmic peptides | | | PS-2 Cytoplasmic peptides | | |
|---|---|---|---|---|---|
| ic1(1-16) | KSVSFYTRKDGQLIYT | (SEQ 2 aa 101-115) | KSVRFYTEKNGQLIYT | (SEQ 4 aa 107-122) |
| ic1(17-32) | PFTEDTETVGQRALHS | (SEQ 2 aa 117-132) | TFTEDTPSVGQRLLNS | (SEQ 4 aa 124-138) |
| ic2 | VFKTYNVAVD | (SEQ 2 aa 185-194) | EVLKTYNVAMD | (SEQ 4 aa 190-200) |
| ic3 | KYLPE | (SEQ 2 aa 239-243) | (identical to ic3 of PS-1) | |
| C(1-20) | KKALPALPISITFGLVFYFA | (SEQ 2 aa 429-448) | KKALPALPISITFGLIFYFS | (SEQ 4 aa 410-429) |
| C(21-39) | TDYLVQPFMDQLAFHQFYI | (SEQ 2 aa 449-467) | TDNLVRPFMDTLASHQLYI | (SEQ 4 aa 430-448) |

Example 4

The present studies demonstrate that the GPCR function of PS-1 modulates the production of Aβ. A major question in the study of PS-GPCR function is to determine a specific ligand for PS that can elicit G-protein activities from the PS, to which the ligand binds intercellularly. The present studies investigated whether the three-part ligand-receptor-G-protein system initiates the production of Aβ. In such a system activation of PS by ligand (β-APP) binding would lead to G-protein binding to PS in the cytoplasmic domain.

In order to investigate whether G-protein binding to PS-1 or PS-2 affects Aβ production from β-APP, cell:cell interaction of β-APP and PS-1 in the presence and absence of Pertussis toxin (PTx) experiments were performed. PTx is a specific inhibitor of G-protein $G_o$ activation. If the GPCR function of PS is involved in the production of Aβ from β-APP:PS intercellular binding, then in its presence, Aβ production should be inhibited.

β-APP:PS-1 mediated cell-cell interactions were carried out using methods described above, with PS-1 transfected primary β-APP−/− fibroblasts (cells express PS-1 and do not produce β-APP) interacted with β-APP-transfected ES (PS−/−) cells (cells produce β-APP but do not express PS) in the presence of $^{35}$S-methionine. 24 h after co-culture of the transfected cells, the samples were harvested in the presence of protease inhibitors. Cells were sonicated and 100 μg of whole cell extracts were immunoprecipitated with antibodies to Aβ (6E10) and immunoprecipitated samples were run on Bicene-Tris gels. Aβ bands were visualized by autoradiography of dried gels. The same experiment was carried out in the presence of 500 ng/ml of PTx. Treatment of cultured cells was carried out for 12 h as described below. As a control for PTx treatment, the cultured cells were incubated with PTx buffer only containing ATP and NAD. Under these conditions activation of Go and levels of Aβ should be unaffected.

Figure 15:
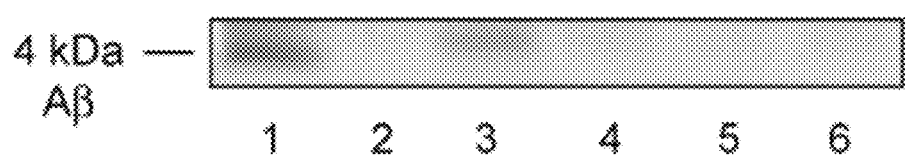
FIG. 15 shows the effect of intercellular β-APP:PS interactions on Aβ production.

FIG. 15 shows the results of these studies. Lane 1 shows the results of β-APP-expressing ES (PS−/−) cells co-cultured with PS-1-expressing Fibroblasts (β-APP−/−). Lane 2 shows the results of the components used in lane 1 in the presence of PTx and PTX buffer (NAD+ATP). Lane 3 shows the results of the components used in lane 1 in the presence of PTx buffer only (NAD+ATP), and no PTx. Lane 4 shows the results of tail-less β-APP-expressing ES (PS−/−) cells co-cultured with +Tail-less PS-1-expressing Fibroblasts (8-APP−/−). Lane 5 shows the results of the components used in lane 4 in the presence of PTx. Lane 6 shows the results of wild type β-APP-expressing ES (PS−/−) cells co-cultured with Tail-less PS-1-expressing fibroblasts (β-APP−/−).

The results indicate that PTx toxin inhibits the production of Aβ from the intercellular interaction of β-APP and PS-1 (lanes 1 and 2 above). Lane 3 shows that in the presence of PTx buffer only, but in the absence of PTx, Aβ production is not inhibited. Lanes 4 and 6 show that the cytoplasmic carboxyl terminal domain of PS-1, earlier shown to be the binding domain of PS-1 for Go, when absent, eliminates Aβ production.

The data provided herein indicate that β-APP is a ligand for PS-1 which upon binding activates its GPCR activity. The data also indicates that the GPCR function of PS-1 is involved in the production of Aβ from β-APP after its intercellular interaction with PS-1. These results further indicate that modulating GPCR activity of PS-1 also modulates the production of Aβ. Accordingly, agents that modulate GPCR activity of PS-1 will modulate the production of Aβ.

For co-culture experiments ES (PS$^{−/−}$) and β-APP ($^{−/−}$) cells were plated at 1×10$^7$ cells per 25 cm$^2$ flask and transfected with the appropriate cDNAs. 5 hours after transfection, ES (PS-1$^{−/−}$/PS-2$^{−/−}$) cells transfected with β-APP were detached by mild trypsinization, washed 2× with met-free culture medium containing heat-inactivated, dialysed FCS (10% v/v) and resuspended in this medium at 0.33×10$^7$ cells/ml. Similarly, primary fibroblasts from β-APP knockout mice were co-transfected with PS-1 or PS-2 and plated at 1×10$^7$ cells. Transfected cells were washed 2× with met free medium and left in 3 ml met-free medium.

β-APP transfected ES (PS-1$^{−/−}$/PS-2$^{−/−}$) cells (1×10$^7$ cells/3 ml met-free medium) were added to the PS-1-transfected 13-APP knockout cells. The cell densities ensured that essentially all the cells were in contact with another. $^{35}$S-met (66 μCi/ml; 1175Ci/mmol, NEN) was added and the cultures incubated for 24 h. In experiments with PTx treatment, 500 ng/ml PTx was added to the cultures under the appropriate reaction conditions at this stage and incubated for 24 h. The medium was then removed and cells harvested by scraping. A protease inhibitor mix was added to the medium before freezing on dry ice. 100 μl extraction buffer (50 mM Tris, pH 8.0/150 mM NaCl/0.5% Nonidet-P40) containing protease inhibitors (1 mM 4-(2-aminoethyl) benzene sulfonyl fluoride hydrochloride (AEBSF)/1 μg/ml antipain/0.1 μg/ml pepstatin A/0.1 μg/ml leupeptin) was added to the cell pellet and the samples quick-frozen on dry ice.

The PTx protomer (Biomol Research Laboratories) was incubated with 10 mM DTT at 37° C. for 10 min to convert it to its enzymatically active form. 5 h after transfecting ES cells with PS-1 or PS-2 and the G-protein cDNAs, 500 ng/ml of activated PTx was added to the cells in culture medium in the presence of 1 mM NAD, 1 mM ATP, 2 mM MgCl2 and 1 mM EDTA. The cells were incubated at 37° C. in the presence of 5% $CO_2$ for 18 h.

Whole cell extracts were prepared using cell-pellets sonicated with 3 bursts of 20 seconds each on ice. Protein concentration was determined according to the method of Lowry.

Immunoprecipitations were carried out using 100 μg of cell extract subjected to immunoprecipitation in an end-over-end rotator at 4° C. overnight with 2 μg Aβ specific monoclonal antibodies 6E10 (Senetek), which was raised to residues 1-17 of Aβ (Senetek). 40 μl slurry of Protein G sepharose (Pharmacia) was then added and allowed to mix end-over-end for 1 h at room temperature. The antigen-antibody-Protein G sepharose complex was washed once with each of the following: buffer 1(10 mM Tris-HCl, pH 7.4, 1 mM EDTA, pH 8.0, 0.65M NaCL, 1% NP-40), buffer 2(10 mM Tris-HCl, pH 7.4, 1 mM EDTA, pH 8.0, 0.75% NP-40) and buffer 3(10 mM Tris-HCl, pH 7.4, 1 mM EDTA, pH 8.0, 0.1% NP-40). The washed complex was boiled for 10 min in bicene-tris sample buffer and subjected to SDS PAGE on bicene-tris gels.

Bicene-tris gels (15% T/5% C) with 8M urea was cast and run. The gels were then fixed for 30 min with 5% glutaraldehyde in 0.4M sodium borate/phosphate buffer and stained for 1 h with 0.1% Coomassie Blue G250 in methanol-acetic acid. After destaining the gels were prepared for autoradiography.

The destained gels were treated with ethanol (30%) and glycerol (5%) for 30 min and impregnated with Amplify (Amersham) for 30 min, dried under vacuum at 80° C. and exposed to X-Omat film at −70° C. for 4-5 days.

The specific β-APP:PS-mediated cell-cell interaction that is required for the eventual production of Aβ also activates G-protein. Cell:cell interaction, mediated by the specific binding of β-APP on one cell surface with PS on the other cell surface, is a required initial step in the production of Aβ from β-APP. To determine whether a cell-cell interaction between human β-APP-only- and PS-only-expressing cells, along with their associated endogenous proteins, resulted in endogenous mouse G-protein activation, binding of $^{35}$S-GTPγS with Gα, a standard method to determine G-protein activation, was assayed. In all of these studies, activation of endogenous mouse $Gα_o$ was examined.

Two cell types were generated: ES-derived mouse cells (PS-1$^{−/−}$; PS-2$^{−/−}$) that expressed only small amounts of endogenous β-APP but no PS, were transiently transfected with cDNA for human β-APP to produce cells expressing excess human β-APP over mouse β-APP, and no PS-1 or PS-2 β-APP-only cells). Embryonic (E18) mouse primary fibroblasts derived from β-APP-null mice, expressing only small amounts of endogenous PS-1 and PS-2, were transfected with cDNAs for human PS-1 to produce cells expressing excess human over mouse PS-1 but no β-APP (PS-1-only cells). The β-APP-only and PS-1-only expressing cells were co-cultured for 24 h, either at high densities which allowed their intercellular interaction, or at lower densities which permitted only lesser degrees of cell:cell interaction (see the light micrographs in FIG. 16C, lane 2 compared to FIG. 16C, lane 4).

Figure 16:
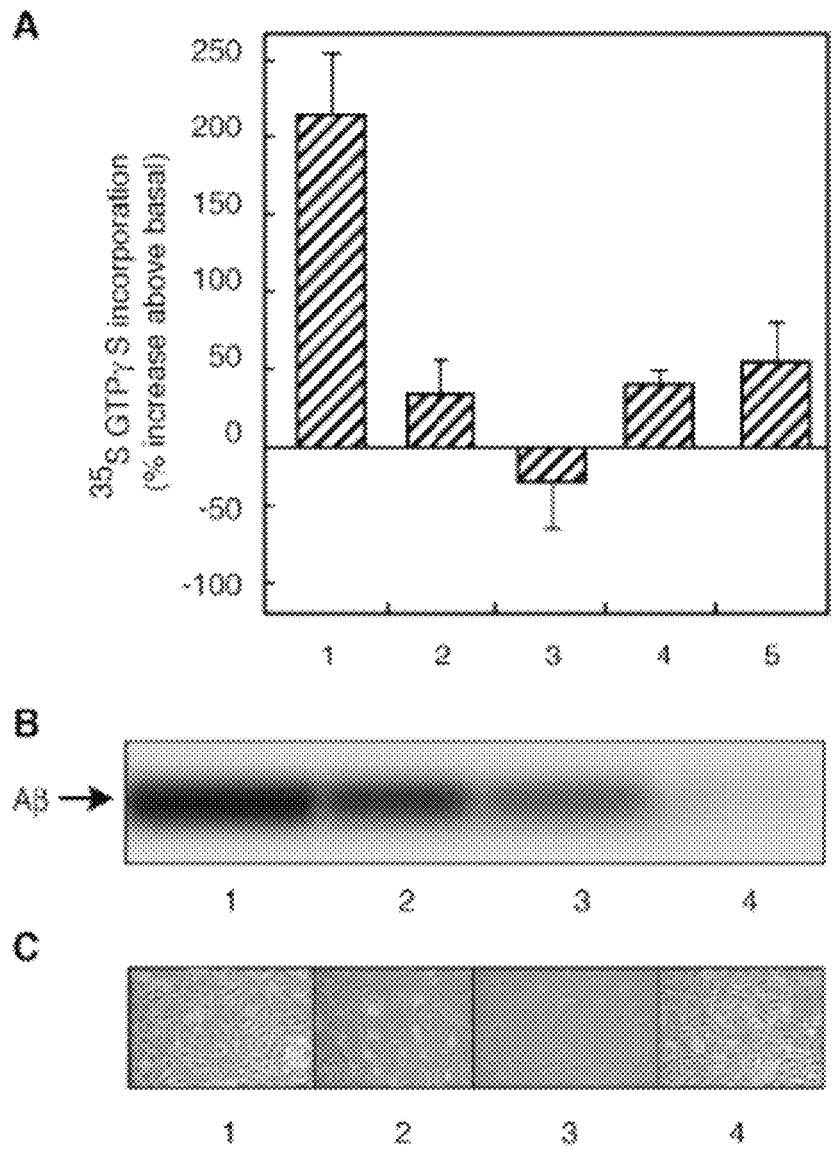
FIG. 16A-C shows G-Protein activation results from specific β-APP:PS mediated cell-cell interaction for the production of Aβ. (A) $^{35}$S-GTPgS incorporation to demonstrate activation of intracellular G-protein in high- and low-density β-APP:PS-1 co-cultures. $^{35}$S-GTPgS incorporation in co-cultures of β-APP-only with PS-1-only cells at high density (lane 1), after immunoprecipitation with antibody K-20 directed to Gα$_o$. Lane 1 shows over 200% increase in $^{35}$S-GTPgS incorporation above basal levels. (see below). Lane 2: The same cells when cultured at lower densities showing 33% increase. Lane 3: The high density co-cultures in the presence of PTx decreased $^{35}$S-GTPgS binding to 38% below basal. Lane 4: High density co-culture in which β-APP was replaced by vector pcDNA3. Lane 5: High density co-culture in which PS-1 was replaced by pcDNA3. Both show low levels of G-protein activation, presumably due to the presence of endogenous mouse β-APP or PS-1 present in the pcDNA transfected cell. Data are presented as activation promoted by β-APP:PS-1 intercellular interaction, expressed as a percentage, where 0% is the $^{35}$S-GTPgS binding in control, prepared by mixing extracts in equal amounts from untransfected ES null cells and untransfected APP$^{-/-}$ fibroblasts. (B) and (C) Aβ Production in PS-1:β-APP co-cultures at different cell densities and in the presence or absence of PTx. Co-cultures of β-APP-only with PS-1-only cells in the presence of $^{35}$S-met at the final numbers of 1.5×10$^7$ (lanes 1 and 4), 0.3×10$^7$ (lanes 2) and 0.15×10$^7$ (lanes 3). PTx (500 ng/ml) was added to the high density culture in lanes 4. (B) Equivalent amounts (100 μg protein) of each cell extract were immunoprecipitated with MAb 6E10, electrophoresed on bicene-tris gels and autoradiographed. The amount of Aβ produced per cell decreased with decreasing cell density (B), lane 1 versus lanes 2 and 3). The presence of PTx in the high density culture (B, lane 4) completely inhibited the Aβ produced in a similar culture not containing PTx (B, lane 1). (C) The densities of the cell cultures were photographed.

Detergent-buffer extracts of the high and low-density co-cultures in the presence and absence of Pertussis toxin (PTx) (the activation of $G_o$ is inhibited in the presence of PTx) were prepared and aliquots each containing 100 μg total protein were reacted with $^{35}$S-GTPγS. Immunoprecipitation of each $^{35}$S-GTPγS-treated extract was carried out with polyclonal antibodies K-20 directed to $Gα_o$, which immunoprecipitated the activated $^{35}$S-GTPγS-labeled mouse $Gα_o$.

Where β-APP-only cells were co-cultured with PS-1-only cells at high density (FIG. 16C, lane 1), there was a greater than 200% increase in $^{35}$S-GTPγS incorporation (FIG. 16A, lane 1) over basal values obtained from control extract (prepared by mixing equal parts of untransfected ES (PS$^{-/-}$) and fibroblast (8-APP$^{-/-}$) cell extracts), compared to a 33% increase (FIG. 16A, lane 2) for the low density samples (FIG. 16C, lane 2). In the presence of PTx, the high density cultures (FIG. 16C, lane 4) showed an inhibition in $^{35}$SGTPγS incorporation, 38% lower than basal values (FIG. 16A, lane 3). These results indicate that a specific cell:cell interaction between the β-APP-only and PS-only cells also activates PTx-sensitive G-proteins either directly via PS-1 cytoplasmic domains, or indirectly via PS-associated proteins.

β-APP-only and PS-only cells were co-cultured at high and low densities and metabolically labeled in the presence of $^{35}$S-met, either with or without PTx. After 24 h co-culture, the cells were harvested and detergent extracts prepared. Samples, each containing 100 μg protein, were immunoprecipitated with mouse MAb (6E10) to human Aβ, following which the solubilized immunoprecipitates were electrophoresed on Bicene-Tris gels. The Aβ bands were then visualized by $^{35}$S-autoradiography. FIG. 16 demonstrates: 1) that Aβ levels present in equal amounts of total protein decreased steadily (FIG. 16B, lanes 1-3) with decreasing cell density (FIG. 16C, lanes 1-3), consistent with a requirement for a β-APP:PS-1-mediated intercellular binding in order to produce Aβ from β-APP; 2) a requirement for the same intercellular interaction for PTx-sensitive G-protein activation, as shown in FIG. 16A; and 3) that the production of Aβ in the high density culture (FIGS. 16B, lane 1 and 16C, lane 1) was completely inhibited in the presence of PTx (FIGS. 16B lane 4 and 16C lane 4). The demonstration of an inhibition of both G-protein activation and Aβ production by PTx strongly suggests that the activation of the G-protein occurs prior to Aβ formation, consistent with the concept that such activation is on the pathway to Aβ production from the β-APP:PS-1 intercellular binding.

A fusion construct of the water-soluble entire 80 amino acid $NH_2$-terminal domain of PS-1 (Peptide 1-80) added to the co-culture medium functioned as a specific competitive inhibitor of the β-APP:PS-1 mediated cell-cell interaction and inhibited Aβ production. As a further evidence of a requirement for a specific cell-cell interaction between β-APP and PS for both G-protein activation and Aβ production, experiments were performed to determine whether the activation of $Gα_o$ that resulted from this cell-cell interaction could be inhibited by the addition to the co-cultures of Peptide 1-80.

Figure 17:
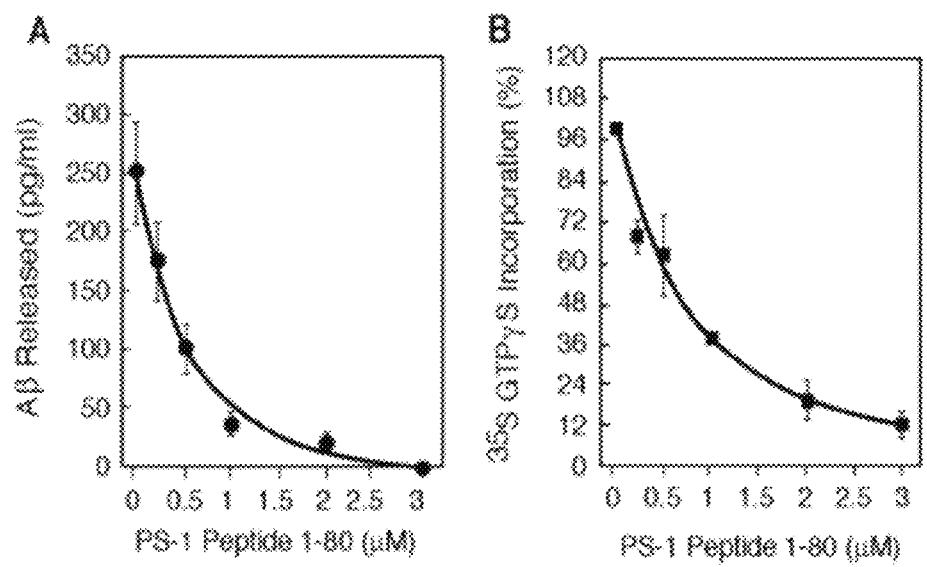
FIG. 17A-B shows specific inhibition of β-APP:PS mediated cell-cell interaction inhibits both G-Protein Gα$_o$ activation and Aβ production. (A) ELISAs to measure Aβ production in the presence of PS-1 Peptide 1-80. Co-cultures of β-APP-only and PS-1-only expressing cells carried out in the presence and absence of increasing amounts of Peptide 1-80 (0-3 μM). Aβ production was determined by ELISA and was inhibited by Peptide 1-80 in a dose-dependent manner. (B) GTPgS assays to measure G-protein activation in the presence of PS-1 Peptide 1-80. Co-cultures of β-APP-only and PS-1-only expressing cells carried out as in (A) above in the presence and absence of increasing amounts of Peptide 1-80 (0-3 μM). $^{35}$S-GTPgS assays were carried out on extracts as a measure of G-protein activation which was similarly inhibited by Peptide 1-80 in a dose-dependent manner. Data are presented as inhibition of G-protein activation, expressed as a percentage, where 100% is the $^{35}$S-GTPgS binding in the β-APP:PS-1 co-cultures in the absence of Peptide 1-80.

Co-cultures of β-APP-only and PS-1-only cells were carried out in the presence and absence of Peptide 1-80 (0-3 μM). $^{35}$S-GTPγS assays were carried out on extracts as a measure of G-protein activation. The Aβ produced in these co-culture extracts was determined by ELISA. FIG. 17 shows that both, the production of Aβ (FIG. 17A) and the activation of $Gα_o$ (FIG. 17B), could be inhibited by Peptide 1-80 in a dose-dependent manner, consistent with the view that the G-protein activation results from the same β-APP:PS-1 mediated cell-cell interaction that initiates the eventual production of Aβ.

In addition, water-soluble β-APP ectodomain itself (8-APPs), when added to cultures of PS-1- only cells, could also activate G-proteins in a dose-dependent manner. β-APPs was partially purified from conditioned media of baculovirus cultures over-expressing human β-APP. The final product (FIG. 18b, lane 1) had, in addition to β-APP, three major contaminating bands at 81 kDa, 55 kDa and 31 kDa that co-purified with the β-APP ectodomain. This partially purified β-APPs preparation was added in increasing amounts to PS-1- only APP$^{-/-}$ fibroblasts. After 15 mins the cells from each well were harvested in extraction buffer, and detergent extracts (each containing 100 μg protein) were treated with $^{35}$S-GTPγS. Activation of $Gα_o$ was assayed after immunoprecipitation of the activated $^{35}$S-GTPγS-$Gα_o$ with the $Gα_o$-specific antibodies. Increase in incorporation of $^{35}$S-GTPγS (FIG. 3A, curve 1) was observed in the PS-1-only cells with increasing concentration of the partially purified β-APPs, with a maximum increase of over 500% with the addition of 120 pM β-APPs. Cultures of untransfected APP$^{-/-}$ fibroblasts gave modest G-protein activation (FIG. 18A, curve 3), presumably due to the presence of endogenous PS-1 in these cells. Furthermore, when partially purified β-APPs was added to untransfected ES (PS$^{-/-}$) cells, no increase in G-protein activation was observed by $^{35}$S-GTPγS assays (FIG. 18A, curve 5), further implicating PS as a receptor for the β-APP ligand in the $Gα_o$ activation.

Figure 18:
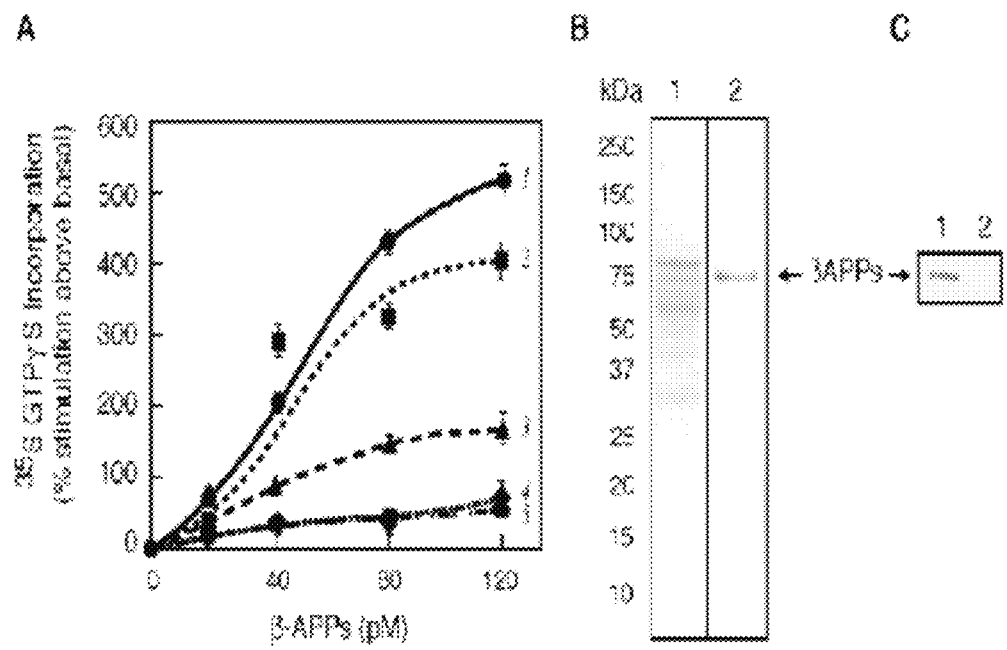
FIG. 18A-C shows G-protein activation by the soluble ectodomain of β-APP (β-APPs). (A) Addition of partially purified β-APPs, at the concentrations of β-APPs shown, to PS-1-only APP$^{-/-}$ fibroblast cultures increased $^{35}$S-GTPgS incorporation in a dose-dependent manner (curve 1); Similar concentrations of β-APPs added to cultures of untransfected APP$^{-/-}$ fibroblasts expressing only endogenous levels of PS resulted, as expected, in only modest increases in $^{35}$S-GTPgS incorporation (curve 3); Addition of equivalent β-APPs-depleted preparations (after pre-treatment with β-APP antibodies) yielded no increases in $^{35}$S-GTPgS incorporation when added to PS-1-transfected APP$^{-/-}$ fibroblasts (curve 4). Addition of equivalent preparations of β-APPs similarly treated with irrelevant antibody (Goat anti-rat IgG) showed slightly lower values than the untreated sample (curve 2). Similar concentrations of β-APPs when added to untransfected ES(PS$^{-/-}$) cultures showed no significant increases in $^{35}$S-GTPgS incorporation (curve 5). Data are presented as stimulation promoted by β-APPs, expressed as a percentage, where 0% is the $^{35}$S-GTPgS binding in the absence of β-APPs. (B) SDS PAGE and Western blot of partially purified β-APPs. Lane 1 shows a Coomassie stained gel of the partially purified β-APPs (arrow) used in this work. Lane 2 is a Western blot of the same preparation with MAb 348 showing the β-APPs band. (C) Western blot to show depletion of β-APPs in sample treated with MAb 348. Lane 1: untreated sample; Lane 2, MAb-treated sample, used in FIG. 18A.

To confirm that it was indeed the β-APPs in the partially purified β-APPs preparation that was the ligand responsible for G-protein activation, and not one of the contaminants, β-APPs was removed from the preparation by treatment with MAb 348 to β-APP (see FIG. 18C, lane 2). This β-APPs-depleted solution at the same concentrations used for the non-depleted preparation, was added to the PS-1-only cells, which were then treated exactly as described above. FIG. 18A (curve 4) shows that the antibody removal of β-APPs resulted in a nearly total loss of the $^{35}$S-GTPγS incorporation that was observed with the β-APPs preparation. In contrast, the β-APPs preparation similarly treated with an irrelevant IgG when added to PS-1-only cells, gave results that resembled those obtained with the untreated samples (FIG. 18A, curve 2). This result is consistent with the proposal that the loss of G-protein activation (FIG. 18A, curve 4) was not due to non-specific protein loss during the immunodepletion procedure, but was due to the specific immuno-removal from the sample of the β-APPs. These results provide evidence that membrane-detached water-soluble β-APPs itself, in addition to intact membrane-bound β-APP, can induce G-protein activation in the PS-1 expressing cells, but not in the absence of PS.

Previous reports have shown that G-protein $G_o$ also binds to β-APP. In the experiments just described with β-APPs there were no β-APP cytoplasmic or intra-membrane domains present; the experiments utilized β-APP$^{-/-}$ cells transfected with PS, to which only the soluble ectodomain of β-APP was added. Thus the $G_o$ activation observed in all the work described herein is due specifically to $G_o$ activation only at the PS cytoplasmic domain, or that of a PS-associated protein.

Figure 19:
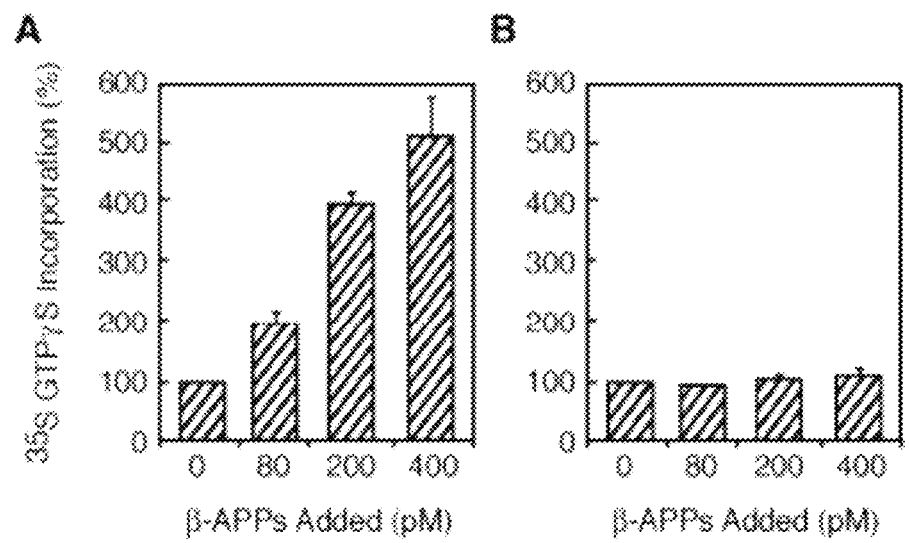
FIG. 19A-B shows activation of Endogenous G-proteins in Rat Membranes. (A) Increasing concentrations (0-400 pM) of β-APPs added to solublized rat hippocampal membranes (100 μg) for 15 min increased $^{35}$S-GTPgS incorporation in a dose-dependent manner. (B) Similar addition of β-APPs to PS-depleted rat membranes which were first pre-treated with a mixture of polyclonal Ab to PS-1 and PS-2. Addition of β-APPs to the PS-depleted membranes showed no increase in $^{35}$S-GTPgS incorporation. Data are presented as stimulation promoted by β-APPs, expressed as a percentage, where 100% is the $^{35}$S-GTPgS binding in the absence of β-APPs.

Because the results so far described were obtained using only cultured cells transfected with human PS, binding of the endogenous rat PS proteins with rat Gα$_o$ present in rat hippocampal membranes was examined. These membranes were solubilized and $^{35}$S-GTPγS assays were carried out on the solubilized membranes, both before and after the addition of increasing concentrations (0-120 pM) of the partially purified β-APPs. FIG. 19A shows that at the lowest concentration of β-APPs (80 pM), the incorporation of $^{35}$S-GTPγS was 100% greater than with untreated samples, and at 400 pM β-APPs, G-protein G$_o$ activation increased by greater than 600%. These increases (FIG. 19B) did not occur if the solubilized rat membranes were first treated with a mixture of polyclonal Ab directed to both PS-1 and PS-2 to deplete the samples of these two mouse proteins, consistent with the participation of PS-1, or its associated proteins, in the G-protein activation by β-APPs.

Experiments were performed to determine whether the human G-protein G$_o$ binds to intact human PS-1 inside ES-derived (PS$^{-/-}$) mouse cells that had been variously transfected with cDNA for human PS-1 together with the cDNA for either human Gα$_{oA}$ or Gα$_{oB}$ proteins. Detergent extracts were prepared from these cells and examined. Extracts each containing 100 μg of protein from ES cells that had been variously transfected, were first immunoprecipitated with MAb specific for the large hydrophilic loop of PS-1 (which protrudes from the exterior of the plasma membrane in the 7-TM model of PS). The immunoprecipitates were then solubilized and subjected to SDS-PAGE, followed by Western blot hybridization with Ab K-20 to Gα$_o$, that recognizes both isoforms, Gα$_{oA}$ and Gα$_{oB}$. Only the PS-1/Gα$_{oA}$ co-transfected cells gave a robust signal for Gα$_o$ at 40 kDa (FIG. 20A, lane 3 compared to lanes 2 and 4), suggesting that Gα$_{oA}$, but not Gα$_{oB}$, binds specifically to PS-1 (the binding being retained in the detergent solution used). The results reflecting the in vitro selective binding of human PS-1 and Gα$_o$ are in agreement with the published studies of the in silico binding of human Gα$_o$ to human PS-1, but they further distinguish between the two Gα$_o$ isoforms, a result not previously shown.

Figure 20:
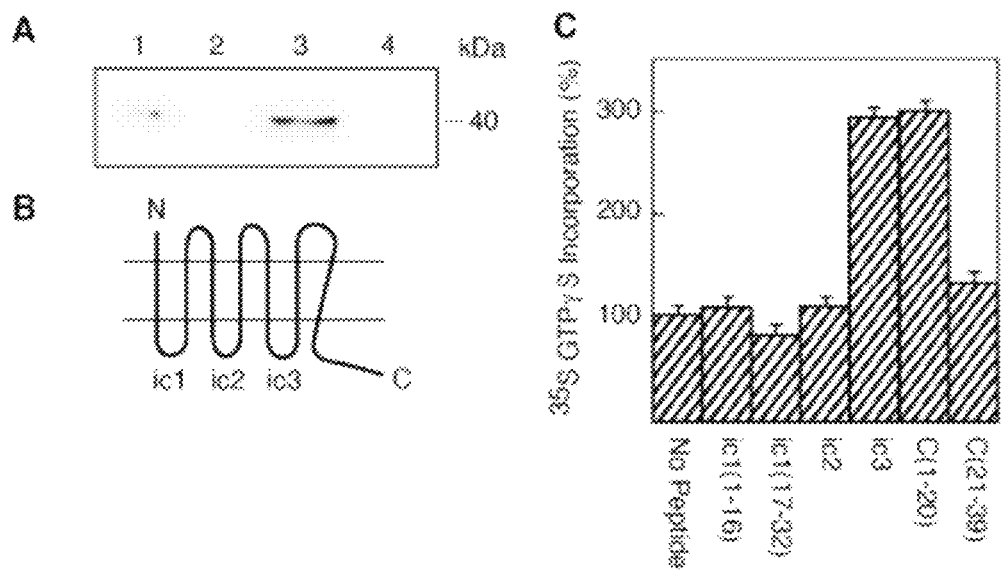
FIG. 20A-C shows direct coupling of human G-protein $G_o$ to human PS-1 cytoplasmic domain. (A) Extracts of variously transfected ES cells were first immunoprecipitated with anti-PS-1 loop MAb, and the immunoprecipitates were electrophoresed and Western blotted with $G_o$ antibody K20 (recognizes $G_{oA}$ and $G_{oB}$.) Lane 1: Untransfected ES null cells; Lanes 2-6, ES null cells transfected with cDNA for: PS-1 only (lane 2); both PS-1 and $G_{oA}$ (lane 3); PS-1 and $G_{oB}$ (lane 4). (B) 7-TM PS-1 showing location of cytoplasmic loop domains 1, 2 and 3 and cytoplasmic C-tail. (C) Effect of PS-1 cytoplasmic peptide fragments on $^{35}$S-GTPgS binding to rat brain $G_o$-protein. Peptides (200 μM) were included in the incubation mixture without pre-treatment, and accumulation of the $^{35}$S-GTPgS was determined. Data are presented as activation promoted by the peptide expressed as a percentage, where 100% is the $^{35}$S-GTPgS binding in the absence of peptide. Lane 1, no added peptide; lane 2, loop 1 residues 1-16, see Table 1 for a list of peptides); lane 3, loop 1 residues 17-32; lane 4, loop 2; lane 5, loop 3; lane 6, residues 1-20 of the C-tail; lane 7, residues 21-39 of the C-tail. Only cytoplasmic loop 3 (lane 5) and peptide C(1-20) comprising the first 20 amino acids of the C-tail (lane 6) promoted a significant 200% increase in activation of $^{35}$S-GTPgS binding over samples without peptide.
Figure 21:
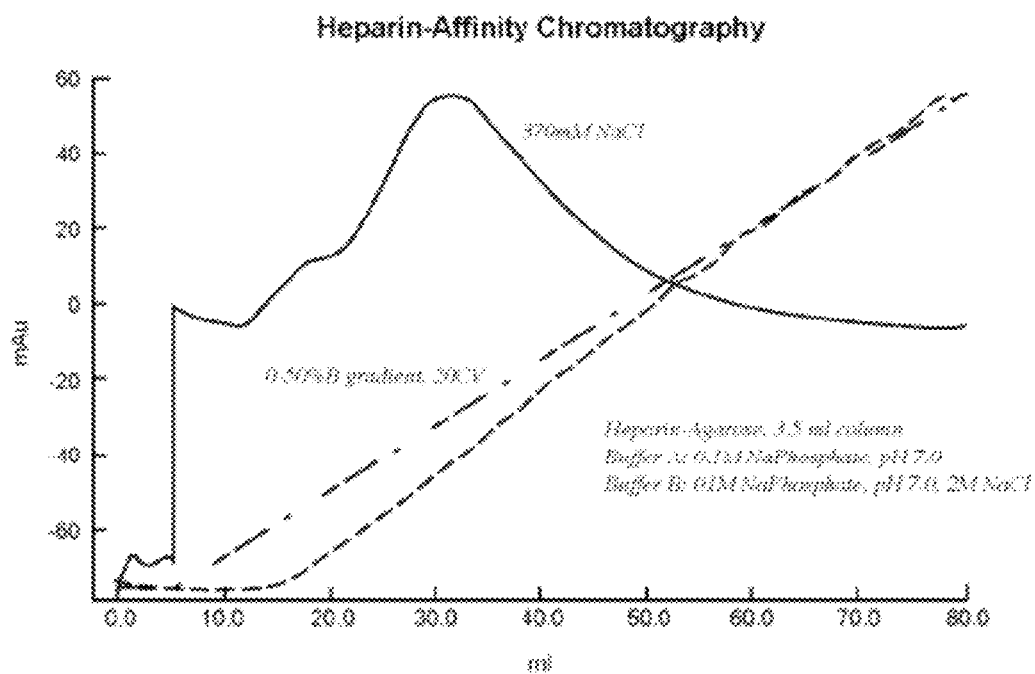
FIG. 21 shows heparin affinity chromatography of polypeptide isolated in the methods of the disclosure.
Figure 22:
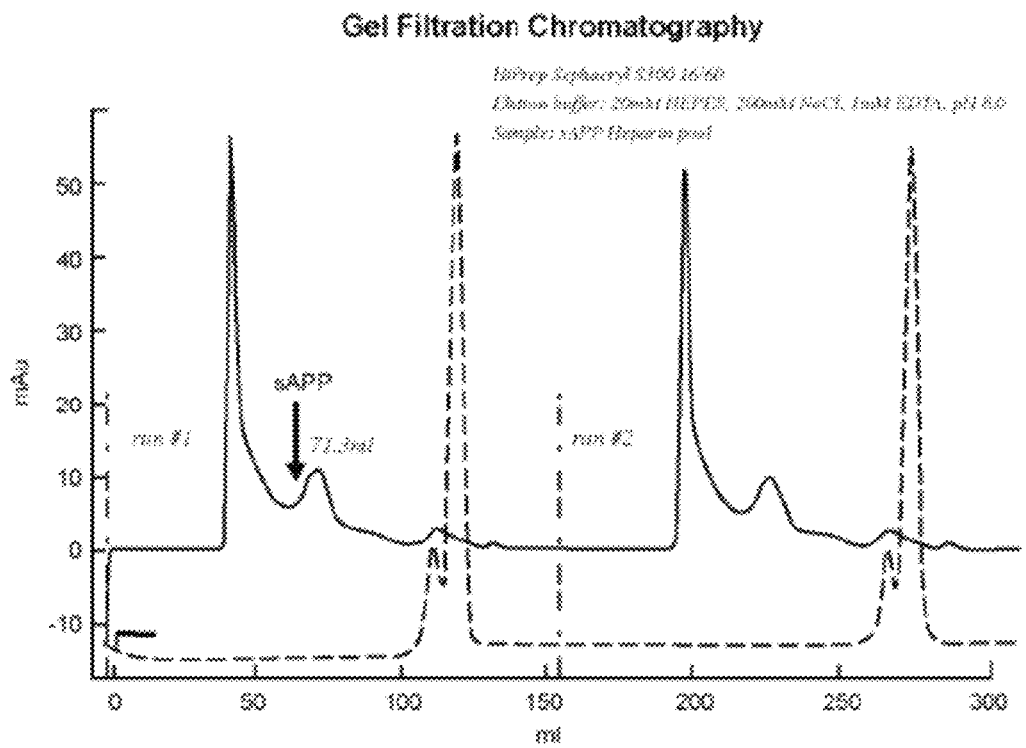
FIG. 22, shows gel filtration chromatography for peptide and polypeptide separation.

To provide evidence that the G$_{oA}$ binding observed in FIG. 5A was directly to PS-1, and not to a co-immunoprecipitated, PS-associated protein the autonomous activation of G$_o$ by synthetic peptide fragments corresponding to cytoplasmic loops 1, 2, 3 and the carboxyl tail of PS-1 (in the 7-TM PS model) were investigated (see FIGS. 20B and C and Table 1). The peptides were individually tested for their ability to stimulate $^{35}$S-GTPγS binding to G$_o$ in rat hippocampal membrane preparations.

In FIG. 20C evidence is presented that cytoplasmic loop 1 and 2 peptides (FIG. 20B) induced only background stimulation of $^{35}$S-GTPγS binding. Cytoplasmic Loop 3 peptide however, produced a robust stimulation of $^{35}$S-GTPγS binding to G$_o$, as did a peptide corresponding to the first 20 amino acids of the COOH-tail. A second COOH-terminal peptide corresponding to residues 21-39, however, failed to activate G$_o$. The result with the peptide corresponding to residues 1-20 of the COOH-tail are in keeping with G-protein activation by the COOH— terminal domain of PS-1. That study, however, missed G$_o$ activation by cytoplasmic loop 3 of 7-TM PS-1, a region known to be important for G-protein binding for most GPCRs. The results confirm that the G$_{oA}$ binds directly to PS-1, and not to PS-associated proteins.

As to the G-protein activation following β-APP:PS cell-cell interaction, it may be involved in Aβ production in any of a number of ways. It may signal the phosphorylation or internalization of the β-APP:PS complex from the plasma membrane, or it may activate other downstream events such as Ca$^{2+}$ release, that might be directly involved in the pathway to the production of Aβ.

The data demonstrate that the G-protein activation resulting from the specific cell:cell interaction of β-APP with PS is on the pathway of the subsequent production of Aβ from β-APP.

In order to determine whether any other G-proteins besides Gα$_o$ can couple the Presenilin (PS)-1 cytoplasmic domains, Gα COOH Minigene vectors were used. The carboxyl terminal domains from various G-protein Gα subunits are important sites for receptor binding, and peptides corresponding to the COOH-termini can be used as competitive inhibitors of receptor-G-protein interactions. Minigene vectors that encode 11-14 C-terminal amino acids of Gα have the ability to inhibit/block receptor mediated activation of signaling pathways. Minigenes cloned in pcDNA3 were obtained from Caden Biosciences. Table 2 shows the specific sequences for each minigene used.

TABLE 2

Peptide Sequences encoded by Gα Minigene vectors

| Gα Insert | C-Terminal Peptide Sequence |
|---|---|
| Gα$_{i1/2}$ | IKNNLKDCGLF (SEQ ID NO: 18) |
| Gα$_{i3}$ | IKNNLKECGLY (SEQ ID NO: 19) |
| Gα$_{oA}$ | IANNLRGCGLY (SEQ ID NO: 20) |
| Gα$_{oB}$ | IAKNLRGCGLY (SEQ ID NO: 21) |
| Gα$_z$ | IQNNLKYIGLC (SEQ ID NO: 22) |
| Gα$_s$ | QRMHLRQYELL (SEQ ID NO: 23) |
| Gα$_{olf}$ | QRMHLKQYELL (SEQ ID NO: 24) |
| Gα$_q$ | LQLNLKEYNAV (SEQ ID NO: 25) |

ES-derived mouse cells (PS-1$^{-/-}$; PS-2$^{-/-}$) that expressed only small amounts of endogenous β-APP but no PS, were transiently transfected with cDNA for human β-APP to produce cells expressing excess human β-APP over mouse β-APP, and no PS-1 or PS-2 β-APP-only cells). Embryonic (E18) mouse primary fibroblasts derived from β-APP-null mice, expressing only small amounts of endogenous PS-1 and PS-2, were transfected with cDNAs for human PS-1 to produce cells expressing excess human over mouse PS-1 but no β-APP (PS-1-only cells). The minigenes were co-transfected with PS-1 in the PS- only APP-/- fibroblasts to inhibit the endogenous mouse Gα under investigation in those cells. PS-/- ES cells were separately transfected with human β-APP cDNA β-APP only cells) and the two types of cells were co-cultured for 24 hours. Cells were harvested and detergent-buffer extracts of the co-cultures were prepared. Determination of [$^{35}$S]GTPγS incorporation in these cultures was carried out in the presence and absence of each minigene: Aliquots each containing 100 μg total protein were reacted with $^{35}$S-GTPγS and immunoprecipitation of each $^{35}$S-GTPγS-treated extract was carried out with antibodies directed to the particular Gα under investigation. Specificity of binding of a particular Gα to PS-1 was established by blocking of GTPγS incorporation in the presence of the specific minigene inhibitor.

Figure 23:
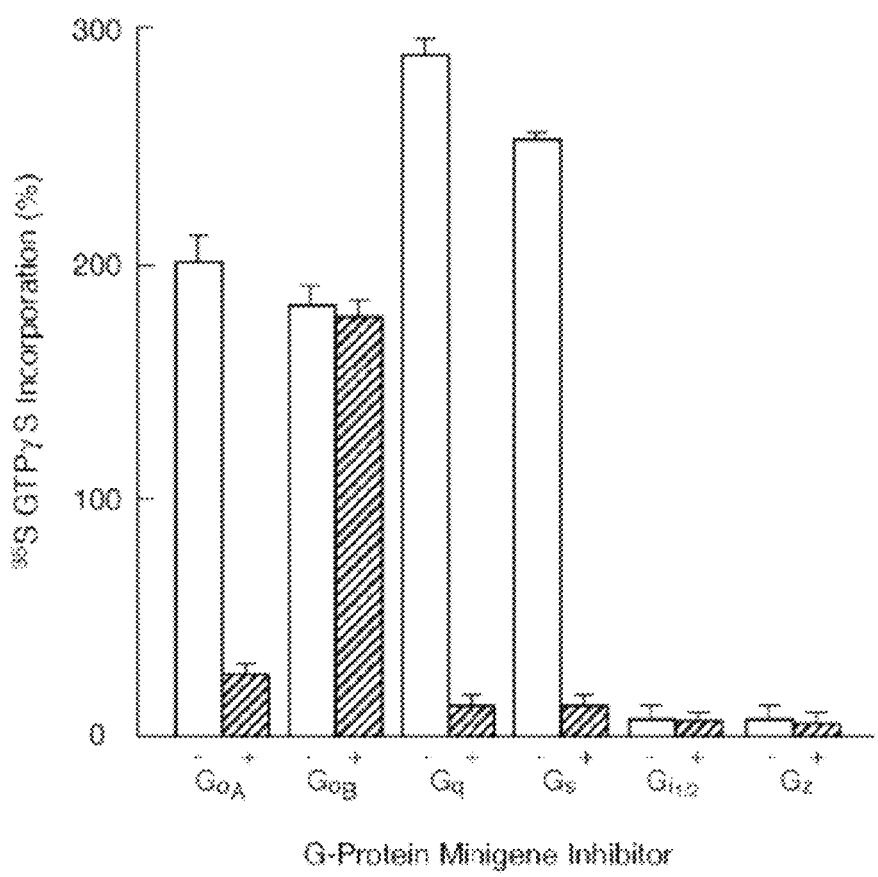
FIG. 23 shows the effect of G-protein minigene inhibitors on $^{35}$S-GTPγS incorporation.

FIG. 23 shows the presence or absence of G-protein activation, following β-APP:PS-1 cell-cell interaction, of Gα$_{oA}$, Gα$_B$, Gα$_q$, Gα$_s$, Gα$_{i1/2}$ and Gα$_z$ in the presence and absence of their specific minigene inhibitors. β-APP:PS-1 cell-cell interaction specifically activated Gα$_{oA}$, Gα$_q$ and Gα$_s$, and that activation was inhibited by the specific minigene inhibitor of each G-protein. The presence of the Gα$_{oB}$ minigene did not inhibit the activated Gα$_o$ protein immunoprecipitated by the Gα$_o$ antibody (this antibody cross-reacts with both the G$_{oA}$ and G$_{oB}$ isoforms) suggesting that the activated species is the G$_{oA}$ protein in this sample, which is not inhibited by the G$_{oB}$ minigene. No G-protein activation was seen for Gi1/2 or Gz as a result of the β-APP:PS-1 cell-cell interaction, suggesting that these G-proteins do not couple PS-1.

Figure 24:
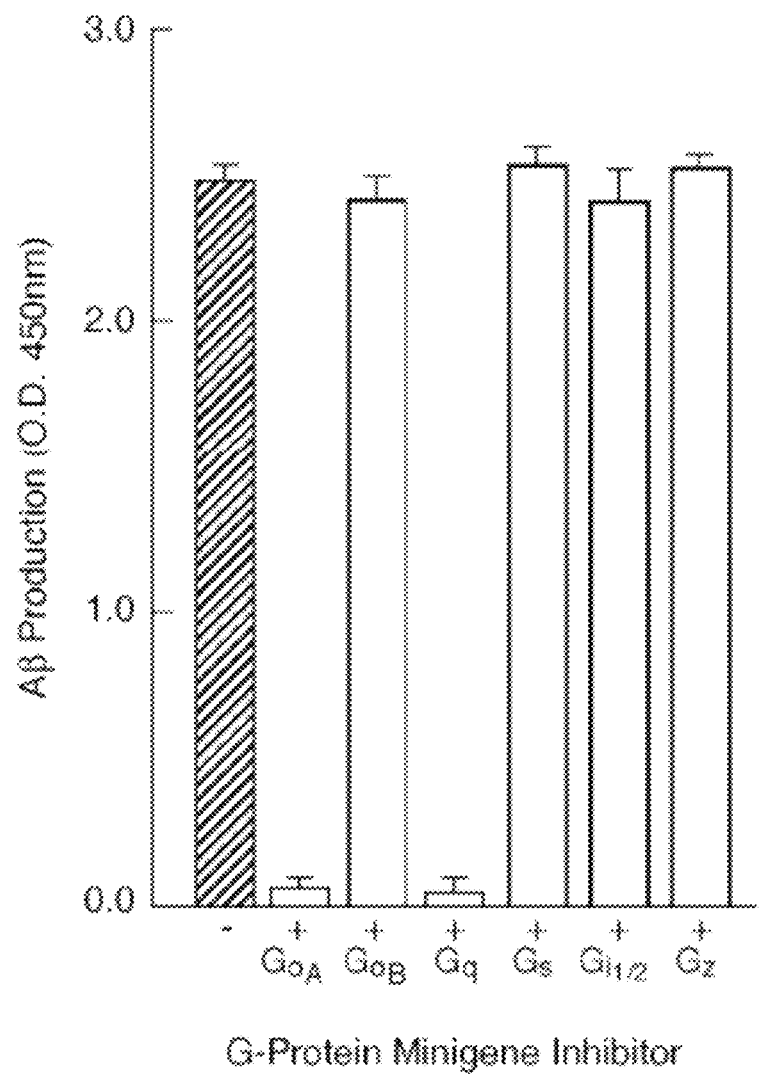
FIG. 24 shows the effect of G-Protein minigene inhibitors on Aβ production.
Figure 26:
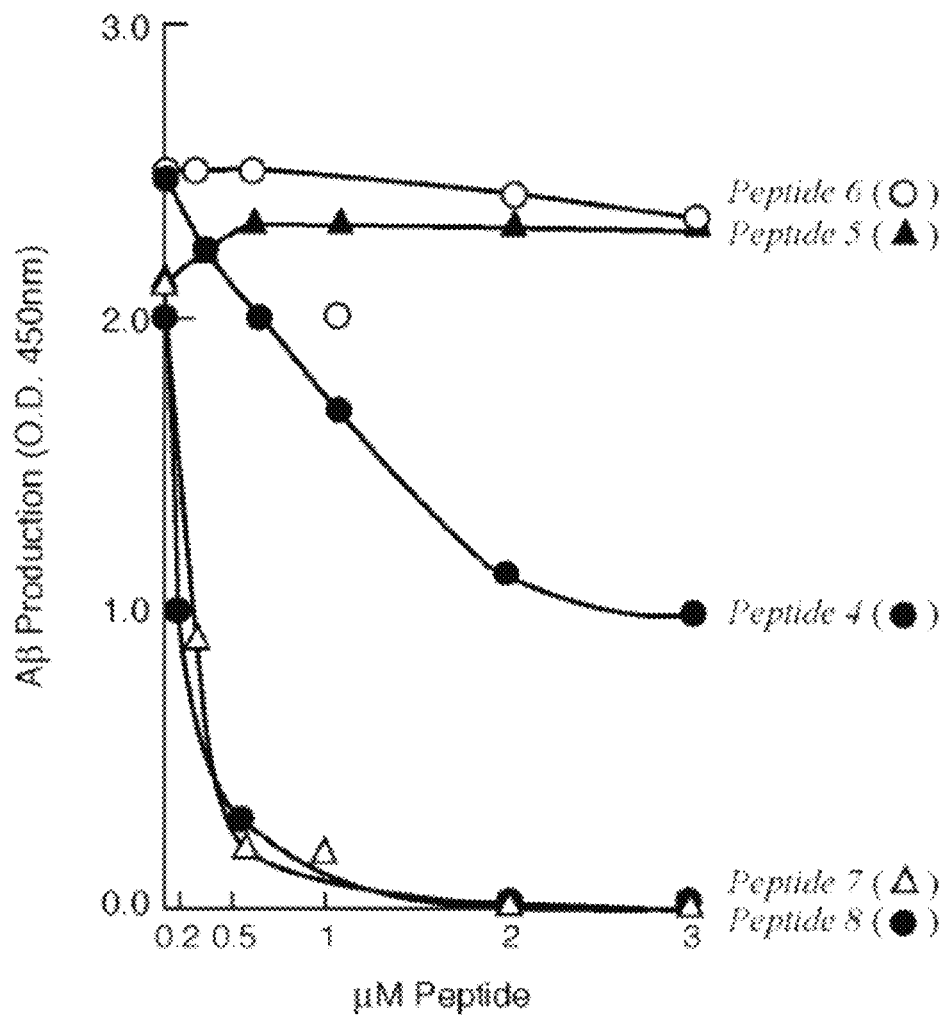
FIG. 26 shows inhibition of Aβ production following β-APP:PS-1 intercellular interaction in the presence of synthetic peptides. Addition of 0-3 μM of only Peptides 4, 7 and 8 at the time of the co-culture of the β-APP-only ad PS-1-only cells inhibits cell-cell interaction and Aβ production, as measured by ELISA assays. PEPTIDE 4: (15-mer) RRSLGH-PEPLSNGRP (SEQ ID NO:5); PEPTIDE 5: (15-mer) SNGRPQGNSRQVVEQ (SEQ ID NO:15); PEPTIDE 6: (15-mer) RQVVEQDEEEDEELT (SEQ ID NO:16); PEPTIDE 7: (15-mer) DEEEDEELTLKYGAK (SEQ ID NO:17); PEPTIDE 8: (8-mer)DEEEDEEL (SEQ ID NO:5).

These data demonstrate that cell-cell interaction between β-APP and PS-1 also activates G-proteins G$_q$ and G$_s$. Aβ produced in the co-culture extracts described above were determined by ELISA. The results in FIG. 24 show that for the PS-1:β APP intercellular interaction, the activation of Gα$_{oA}$ and Gα$_q$ coincides with the production of Aβ, whereas the activation of Gα$_s$ does not. When the G-protein activation of these proteins is inhibited by the presence of the specific minigene inhibitor for each G-protein, the Aβ production is also inhibited in the case of Gα$_{oA}$ and Gα$_q$, but not in the case of Gα$_s$. These results demonstrate that the production of Aβ from β-APP involves the downstream signaling pathways of the G-proteins G$_o$ and G$_q$, both of which signal via PLC (different mechanisms).

The autonomous activation of G-proteins Gα$_o$, Gα$_q$ and Gα$_s$ by oligopeptides corresponding to cytoplasmic loops 1, 2, 3 and the COOH tail of human PS-1 in the 7-TM PS model were examined. The peptides were individually tested for their ability to stimulate $^{35}$S-GTPγS binding to each G-protein in rat hippocampal membrane preparations.

FIG. 25A shows the autonomous activation of Gα$_o$ by cytoplasmic loop peptides of PS-1. Evidence is presented that cytoplasmic loop 1 and 2 peptides induced only background stimulation of $^{35}$S-GTPγS binding. Cytoplasmic Loop 3 peptide however, produced a robust stimulation of $^{35}$S-GTPγS binding to G$_o$, as did a peptide corresponding to the first 20 amino acids of the COOH-tail. A second COOH-terminal peptide corresponding to residues 21-39, however, had no detectable G$_o$ activation.

FIG. 25B shows the autonomous activation of Gα$_q$. Cytoplasmic loop 1 and 2 peptides induced only background stimulation of $^{35}$S-GTPγS binding. Cytoplasmic Loop 3 peptide, as for Gα$_o$, produced a robust stimulation of $^{35}$S-GTPγS binding to G$_q$, as did a peptide corresponding to the last 19 amino acids of the COOH-tail. A COOH-terminal peptide corresponding to residues 1-20, previously shown to activate G$_o$, did not provide detectable activation of G$_q$.

FIG. 25C shows the autonomous activation of Gα$_s$. Cytoplasmic loop 1 peptides comprising residues 17-32 (but not the first 16 amino acids of loop 1) as well as a peptide corresponding to the last 19 amino acids of the COOH-tail induced stimulation of $^{35}$S-GTPγS binding. Cytoplasmic Loops 2 and 3 peptides, as well as the COOH-terminal peptide 1-20 for Gα$_o$ induced only background stimulation of $^{35}$S-GTPγS binding.

These results indicate that the different G-proteins bind to different cytoplasmic domains or combination of domains on the PS-1.

Primary Antibodies: Polyclonal Ab to Gα$_o$, K-20, sc-387, Gαq, Gαs, Gαi1/2, and Gαz were purchased from Santa Cruz Biotechnology. Gα$_o$ Ab recognizes both, G$_{oA}$ and G$_{oB}$. MAb 6E10 (Senetek), to residues 1-17 of Aβ recognizes both, full-length β-APP, as well as Aβ.

Cell culture: Mouse ES (PS-1$^{-/-}$/PS-2$^{-/-}$) were cultured as previously described.

Preparation of Whole Cell Extracts: Extracts were prepared by sonication in solubilization buffer 1 (50 mM HEPES/NaOH pH 7.4, 1 mM EDTA, 1 mM DTT, 1% Triton-X100, 60 mM octylglycoside, 1× Protease inhibitor mix) and proteins using a Lowry assay.

$^{35}$S-GTPγS Assays: Extract (100 μg of total protein) was mixed with an equal volume of GTPγS Buffer B (50 mM HEPES/NaOH pH 7.4, 40 μM GDP, 50 mM MgCl$_2$, 100 mM NaCl) and reacted with 50 nM $^{35}$S-GTPγS (1250 Ci/mmol, Perkin Elmer, Waltham, Mass.) for 60 min at RT. The reaction was stopped with 10× Stopping buffer (100 mM Tris-HCl, pH 8, 25 mM MgCl$_2$, 100 mM NaCl, 20 mM GTP) followed by immunoprecipitation of the $^{35}$S-GTPγS-Gα$_o$ complex with Ab against a particular Gα. The Ab-protein complex was absorbed to Protein A/G agarose for 90 min at RT and washed. The agarose beads were suspended in scintillation fluid (CytoScint, ICN) (5 ml) and counted in a Beckman Coulter LS 6000 SC scintillation counter for 3 min.

Co-culture of β-APP-only with PS-1-only cells was carried out as described above.

ELISA for the production of Aβ1-40 was carried out using sandwich ELISA kits (Biosource).

Rat hippocampal membranes (Applied Cell Science, Rockville, Md.) were solubilized in CHAPs buffer.

Peptides (200 μM) were incubated without pre-treatment with solubilized rat hippocampal membranes (50 μg) in the $^{35}$S reaction mixture. Accumulation of γ-S GTP the $^{35}$S-GTPγS was determined after immunoprecipitation with the specific anti-G Ab.

TABLE 3

Binding of different G-Proteins to Human PS-1

| G-Protein | PS-1 Cytoplasmic Binding Sequence | PS-1 Residues |
|---|---|---|
| Gα$_o$ | KYLPE | 239-243* |
| | KKALPALPISITFGLVFYFA | 429-448* |
| Gα$_q$ | KYLPE | 239-243* |
| | TDYLVQPFMDQLAFHQFYI | 449-467* |
| Gα$_s$ | PFTEDTETVGQRALHS | 117-132* |
| | TDYLVQPFMDQLAFHQFYI | 449-467* |

*residue numbers qare with respect to SEQ ID NO: 2

Although a number of embodiments and features have been described above, it will be understood by those skilled in the art that modifications and variations of the described embodiments and features may be made without departing from the teachings of the disclosure or the scope of the disclosure as defined by the appended claims. The appendices attached hereto are provided to further illustrate but not limit the invention.

What is claimed is:

1. A method of inhibiting the production of Aβ comprising contacting mammalian cells expressing a β-amyloid precursor protein (β-APP) with an isolated polypeptide consisting essentially of an amino acid sequence from the N-terminal fragment of PS-1 (SEQ ID NO:2), wherein the fragment is selected from the group consisting of:
   (i) DEEEDEEL (SEQ ID NO:5),
   (ii) SEQ ID NO:5 further including 1-10 additional amino acids at either the N- and/or C-terminal end(s),
   (iii) RRSLGHPEPLSNGRPQGNSRQWEQDEEEDEELTLKYGAK (SEQ ID NO:7),
   (iv) a polypeptide that is 85% identical to SEQ ID NO:7 having 1-5 conservative amino acid substitutions,
   (v) a sequence consisting of (iii) or (iv) further including 1-10 additional amino acids at the N- and/or C-terminal end(s),
   (vi) DEEEDELTLKYGAK (SEQ ID NO:17),
   (vii) SEQ ID NO:17 further including 1-5 conservative amino acid substitutions,
   (viii) a sequence consisting of (vi) or (vii) further including 1-10 additional amino acids at the N- or C-terminus,
   (ix) any of the foregoing polypeptides comprising an unnatural amino acid or D-amino acid, and
   (x) combinations of any of the foregoing,
   wherein the isolated polypeptide inhibits production of Aβ in a cell.

2. The method of claim 1, wherein the isolated polypeptide consists of the amino acid sequence DEEEDEEL (SEQ ID NO:5).

3. The method of claim 1, wherein the isolated polypeptide consists of the amino acid sequence SEQ ID NO:5 further including 1-10 additional amino acids at either the N- and/or C-terminal end(s).

4. The method of claim 1, wherein the isolated polypeptide consists of the amino acid sequence RRSLGHPEPLSNGRPQGNSRQWEQDEEEDEELTLKYGAK (SEQ ID NO:7).

5. The method of claim 1, wherein the isolated polypeptide is 85% identical to the amino acid sequence of SEQ ID NO:7 but has 1-5 conservative amino acid substitutions.

6. The method of claim 1, wherein the isolated polypeptide consists of the amino acid sequence DEEEDEELTLKYGAK (SEQ ID NO:17).

7. A method of inhibiting interaction of β-amyloid precursor protein (β-APP) and presenilin-1 (PS-1) comprising contacting mammalian cells expressing β-APP and/or PS-1 with an isolated polypeptide consisting essentially of an amino acid sequence from the N-terminal fragment of PS-1 (SEQ ID NO:2), wherein the fragment is selected from the group consisting of:
   (i) DEEEDEEL (SEQ ID NO:5),
   (ii) SEQ ID NO:5 further including 1-10 additional amino acids at either the N- and/or C-terminal end(s),
   (iii) RRSLGHPEPLSNGRPQGNSRQWEQDEEEDEELTLKYGAK (SEQ ID NO:7),
   (iv) a polypeptide that is 85% identical to SEQ ID NO:7 having 1-5 conservative amino acid substitutions,
   (v) a sequence consisting of (iii) or (iv) further including 1-10 additional amino acids at the N- and/or C-terminal end(s),
   (vi) DEEEDELTLKYGAK (SEQ ID NO:17),
   (vii) SEQ ID NO:17 further including 1-5 conservative amino acid substitutions,
   (viii) a sequence consisting of (vi) or (vii) further including 1-10 additional amino acids at the N- or C-terminus,
   (ix) any of the foregoing polypeptides comprising an unnatural amino acid or D-amino acid, and
   (x) combinations of any of the foregoing,
   wherein the isolated polypeptide inhibits interaction between β-APP and PS-1.

8. The method of claim 7, wherein the isolated polypeptide consists of the amino acid sequence DEEEDEEL (SEQ ID NO:5).

9. The method of claim 7, wherein the isolated polypeptide consists of the amino acid sequence RRSLGHPEPLSNGRPQGNSRQWEQDEEEDEELTLKYGAK (SEQ ID NO:7).

10. The method of claim 7, wherein the polypeptide inhibits the production of Aβ.

11. The method of claim 7, wherein the isolated polypeptide consists of the amino acid sequence DEEEDEELTLKYGAK (SEQ ID NO:17).

* * * * *

SEQUENCE LISTING

<160> NUMBER OF SEQ ID NOS: 25

<210> SEQ ID NO 1
<211> LENGTH: 1404
<212> TYPE: DNA
<213> ORGANISM: Homo sapiens
<220> FEATURE:
<221> NAME/KEY: CDS
<222> LOCATION: (1)..(1404)

<400> SEQUENCE: 1

| | | | | | | | | | | | | | | | | |
|---|---|---|---|---|---|---|---|---|---|---|---|---|---|---|---|---|
| atg | aca | gag | tta | cct | gca | ccg | ttg | tcc | tac | ttc | cag | aat | gca | cag | atg | 48 |
| Met | Thr | Glu | Leu | Pro | Ala | Pro | Leu | Ser | Tyr | Phe | Gln | Asn | Ala | Gln | Met | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| tct | gag | gac | aac | cac | ctg | agc | aat | act | gta | cgt | agc | cag | aat | gac | aat | 96 |
| Ser | Glu | Asp | Asn | His | Leu | Ser | Asn | Thr | Val | Arg | Ser | Gln | Asn | Asp | Asn | |
| | | | 20 | | | | | 25 | | | | | 30 | | | |

| | | | | | | | | | | | | | | | | |
|---|---|---|---|---|---|---|---|---|---|---|---|---|---|---|---|---|
| aga | gaa | cgg | cag | gag | cac | aac | gac | aga | cgg | agc | ctt | ggc | cac | cct | gag | 144 |
| Arg | Glu | Arg | Gln | Glu | His | Asn | Asp | Arg | Arg | Ser | Leu | Gly | His | Pro | Glu | |
| | | 35 | | | | | 40 | | | | | 45 | | | | |

| | | | | | | | | | | | | | | | | |
|---|---|---|---|---|---|---|---|---|---|---|---|---|---|---|---|---|
| cca | tta | tct | aat | gga | cga | ccc | cag | ggt | aac | tcc | cgg | cag | gtg | gtg | gag | 192 |
| Pro | Leu | Ser | Asn | Gly | Arg | Pro | Gln | Gly | Asn | Ser | Arg | Gln | Val | Val | Glu | |
| | 50 | | | | | 55 | | | | | 60 | | | | | |

| | | | | | | | | | | | | | | | | |
|---|---|---|---|---|---|---|---|---|---|---|---|---|---|---|---|---|
| caa | gat | gag | gaa | gaa | gat | gag | gag | ctg | aca | ttg | aaa | tat | ggc | gcc | aag | 240 |
| Gln | Asp | Glu | Glu | Glu | Asp | Glu | Glu | Leu | Thr | Leu | Lys | Tyr | Gly | Ala | Lys | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| cat | gtg | atc | atg | ctc | ttt | gtc | cct | gtg | act | ctc | tgc | atg | gtg | gtg | gtc | 288 |
| His | Val | Ile | Met | Leu | Phe | Val | Pro | Val | Thr | Leu | Cys | Met | Val | Val | Val | |
| | | | | 85 | | | | | 90 | | | | | 95 | | |

| | | | | | | | | | | | | | | | | |
|---|---|---|---|---|---|---|---|---|---|---|---|---|---|---|---|---|
| gtg | gct | acc | att | aag | tca | gtc | agc | ttt | tat | acc | cgg | aag | gat | ggg | cag | 336 |
| Val | Ala | Thr | Ile | Lys | Ser | Val | Ser | Phe | Tyr | Thr | Arg | Lys | Asp | Gly | Gln | |
| | | | 100 | | | | | 105 | | | | | 110 | | | |

| | | | | | | | | | | | | | | | | |
|---|---|---|---|---|---|---|---|---|---|---|---|---|---|---|---|---|
| cta | atc | tat | acc | cca | ttc | aca | gaa | gat | acc | gag | act | gtg | ggc | cag | aga | 384 |
| Leu | Ile | Tyr | Thr | Pro | Phe | Thr | Glu | Asp | Thr | Glu | Thr | Val | Gly | Gln | Arg | |
| | | 115 | | | | | 120 | | | | | 125 | | | | |

| | | | | | | | | | | | | | | | | |
|---|---|---|---|---|---|---|---|---|---|---|---|---|---|---|---|---|
| gcc | ctg | cac | tca | att | ctg | aat | gct | gcc | atc | atg | atc | agt | gtc | att | gtt | 432 |
| Ala | Leu | His | Ser | Ile | Leu | Asn | Ala | Ala | Ile | Met | Ile | Ser | Val | Ile | Val | |
| | 130 | | | | | 135 | | | | | 140 | | | | | |

| | | | | | | | | | | | | | | | | |
|---|---|---|---|---|---|---|---|---|---|---|---|---|---|---|---|---|
| gtc | atg | act | atc | ctc | ctg | gtg | gtt | ctg | tat | aaa | tac | agg | tgc | tat | aag | 480 |
| Val | Met | Thr | Ile | Leu | Leu | Val | Val | Leu | Tyr | Lys | Tyr | Arg | Cys | Tyr | Lys | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| gtc | atc | cat | gcc | tgg | ctt | att | ata | tca | tct | cta | ttg | ttg | ctg | ttc | ttt | 528 |
| Val | Ile | His | Ala | Trp | Leu | Ile | Ile | Ser | Ser | Leu | Leu | Leu | Leu | Phe | Phe | |
| | | | | 165 | | | | | 170 | | | | | 175 | | |

| | | | | | | | | | | | | | | | | |
|---|---|---|---|---|---|---|---|---|---|---|---|---|---|---|---|---|
| ttt | tca | ttc | att | tac | ttg | ggg | gaa | gtg | ttt | aaa | acc | tat | aac | gtt | gct | 576 |
| Phe | Ser | Phe | Ile | Tyr | Leu | Gly | Glu | Val | Phe | Lys | Thr | Tyr | Asn | Val | Ala | |
| | | | 180 | | | | | 185 | | | | | 190 | | | |

| | | | | | | | | | | | | | | | | |
|---|---|---|---|---|---|---|---|---|---|---|---|---|---|---|---|---|
| gtg | gac | tac | att | act | gtt | gca | ctc | ctg | atc | tgg | aat | ttt | ggt | gtg | gtg | 624 |
| Val | Asp | Tyr | Ile | Thr | Val | Ala | Leu | Leu | Ile | Trp | Asn | Phe | Gly | Val | Val | |
| | | 195 | | | | | 200 | | | | | 205 | | | | |

| | | | | | | | | | | | | | | | | |
|---|---|---|---|---|---|---|---|---|---|---|---|---|---|---|---|---|
| gga | atg | att | tcc | att | cac | tgg | aaa | ggt | cca | ctt | cga | ctc | cag | cag | gca | 672 |
| Gly | Met | Ile | Ser | Ile | His | Trp | Lys | Gly | Pro | Leu | Arg | Leu | Gln | Gln | Ala | |
| | 210 | | | | | 215 | | | | | 220 | | | | | |

| | | | | | | | | | | | | | | | | |
|---|---|---|---|---|---|---|---|---|---|---|---|---|---|---|---|---|
| tat | ctc | att | atg | att | agt | gcc | ctc | atg | gcc | ctg | gtg | ttt | atc | aag | tac | 720 |
| Tyr | Leu | Ile | Met | Ile | Ser | Ala | Leu | Met | Ala | Leu | Val | Phe | Ile | Lys | Tyr | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| ctc | cct | gaa | tgg | act | gcg | tgg | ctc | atc | ttg | gct | gtg | att | tca | gta | tat | 768 |
| Leu | Pro | Glu | Trp | Thr | Ala | Trp | Leu | Ile | Leu | Ala | Val | Ile | Ser | Val | Tyr | |
| | | | | 245 | | | | | 250 | | | | | 255 | | |

| | | | | | | | | | | | | | | | | |
|---|---|---|---|---|---|---|---|---|---|---|---|---|---|---|---|---|
| gat | tta | gtg | gct | gtt | ttg | tgt | ccg | aaa | ggt | cca | ctt | cgt | atg | ctg | gtt | 816 |
| Asp | Leu | Val | Ala | Val | Leu | Cys | Pro | Lys | Gly | Pro | Leu | Arg | Met | Leu | Val | |
| | | | 260 | | | | | 265 | | | | | 270 | | | |

| | | | | | | | | | | | | | | | | |
|---|---|---|---|---|---|---|---|---|---|---|---|---|---|---|---|---|
| gaa | aca | gct | cag | gag | aga | aat | gaa | acg | ctt | ttt | cca | gct | ctc | att | tac | 864 |
| Glu | Thr | Ala | Gln | Glu | Arg | Asn | Glu | Thr | Leu | Phe | Pro | Ala | Leu | Ile | Tyr | |
| | | 275 | | | | | 280 | | | | | 285 | | | | |

| | | | | | | | | | | | | | | | | |
|---|---|---|---|---|---|---|---|---|---|---|---|---|---|---|---|---|
| tcc | tca | aca | atg | gtg | tgg | ttg | gtg | aat | atg | gca | gaa | gga | gac | ccg | gaa | 912 |
| Ser | Ser | Thr | Met | Val | Trp | Leu | Val | Asn | Met | Ala | Glu | Gly | Asp | Pro | Glu | |
| | 290 | | | | | 295 | | | | | 300 | | | | | |

```
gct caa agg aga gta tcc aaa aat tcc aag tat aat gca gaa agc aca    960
Ala Gln Arg Arg Val Ser Lys Asn Ser Lys Tyr Asn Ala Glu Ser Thr
305             310                 315                 320 gaa agg gag tca caa gac act gtt gca gag aat gat gat ggc ggg ttc   1008
Glu Arg Glu Ser Gln Asp Thr Val Ala Glu Asn Asp Asp Gly Gly Phe
            325                 330                 335 agt gag gaa tgg gaa gcc cag agg gac agt cat cta ggg cct cat cgc   1056
Ser Glu Glu Trp Glu Ala Gln Arg Asp Ser His Leu Gly Pro His Arg
340                 345                 350 tct aca cct gag tca cga gct gct gtc cag gaa ctt tcc agc agt atc   1104
Ser Thr Pro Glu Ser Arg Ala Ala Val Gln Glu Leu Ser Ser Ser Ile
        355                 360                 365 ctc gct ggt gaa gac cca gag gaa agg gga gta aaa ctt gga ttg gga   1152
Leu Ala Gly Glu Asp Pro Glu Glu Arg Gly Val Lys Leu Gly Leu Gly
370                 375                 380 gat ttc att ttc tac agt gtt ctg gtt ggt aaa gcc tca gca aca gcc   1200
Asp Phe Ile Phe Tyr Ser Val Leu Val Gly Lys Ala Ser Ala Thr Ala
385                 390                 395                 400 agt gga gac tgg aac aca acc ata gcc tgt ttc gta gcc ata tta att   1248
Ser Gly Asp Trp Asn Thr Thr Ile Ala Cys Phe Val Ala Ile Leu Ile
            405                 410                 415 ggt ttg tgc ctt aca tta tta ctc ctt gcc att ttc aag aaa gca ttg   1296
Gly Leu Cys Leu Thr Leu Leu Leu Ala Ile Phe Lys Lys Ala Leu
        420                 425                 430 cca gct ctt cca atc tcc atc acc ttt ggg ctt gtt ttc tac ttt gcc   1344
Pro Ala Leu Pro Ile Ser Ile Thr Phe Gly Leu Val Phe Tyr Phe Ala
            435                 440                 445 aca gat tat ctt gta cag cct ttt atg gac caa tta gca ttc cat caa   1392
Thr Asp Tyr Leu Val Gln Pro Phe Met Asp Gln Leu Ala Phe His Gln
450                 455                 460 ttt tat atc tag                                                    1404
Phe Tyr Ile
465

<210> SEQ ID NO 2
<211> LENGTH: 467
<212> TYPE: PRT
<213> ORGANISM: Homo sapiens

<400> SEQUENCE: 2

Met Thr Glu Leu Pro Ala Pro Leu Ser Tyr Phe Gln Asn Ala Gln Met
1               5                   10                  15

Ser Glu Asp Asn His Leu Ser Asn Thr Val Arg Ser Gln Asn Asp Asn
            20                  25                  30

Arg Glu Arg Gln Glu His Asn Asp Arg Arg Ser Leu Gly His Pro Glu
        35                  40                  45

Pro Leu Ser Asn Gly Arg Pro Gln Gly Asn Ser Arg Gln Val Val Glu
    50                  55                  60

Gln Asp Glu Glu Glu Asp Glu Glu Leu Thr Leu Lys Tyr Gly Ala Lys
65                  70                  75                  80

His Val Ile Met Leu Phe Val Pro Val Thr Leu Cys Met Val Val Val
                85                  90                  95

Val Ala Thr Ile Lys Ser Val Ser Phe Tyr Thr Arg Lys Asp Gly Gln
            100                 105                 110

Leu Ile Tyr Thr Pro Phe Thr Glu Asp Thr Glu Thr Val Gly Gln Arg
        115                 120                 125

Ala Leu His Ser Ile Leu Asn Ala Ala Ile Met Ile Ser Val Ile Val
    130                 135                 140
```

| | | | | | | | | | | | | | | | |
|---|---|---|---|---|---|---|---|---|---|---|---|---|---|---|---|
|Val|Met|Thr|Ile|Leu|Leu|Val|Val|Leu|Tyr|Lys|Tyr|Arg|Cys|Tyr|Lys|
|145| | | |150| | | | |155| | | | |160| |

Val Ile His Ala Trp Leu Ile Ile Ser Ser Leu Leu Leu Phe Phe
              165              170              175

Phe Ser Phe Ile Tyr Leu Gly Glu Val Phe Lys Thr Tyr Asn Val Ala
         180               185              190

Val Asp Tyr Ile Thr Val Ala Leu Leu Ile Trp Asn Phe Gly Val Val
      195              200              205

Gly Met Ile Ser Ile His Trp Lys Gly Pro Leu Arg Leu Gln Gln Ala
210              215              220

Tyr Leu Ile Met Ile Ser Ala Leu Met Ala Leu Val Phe Ile Lys Tyr
225              230              235              240

Leu Pro Glu Trp Thr Ala Trp Leu Ile Leu Ala Val Ile Ser Val Tyr
         245               250              255

Asp Leu Val Ala Val Leu Cys Pro Lys Gly Pro Leu Arg Met Leu Val
            260              265              270

Glu Thr Ala Gln Glu Arg Asn Glu Thr Leu Phe Pro Ala Leu Ile Tyr
         275               280              285

Ser Ser Thr Met Val Trp Leu Val Asn Met Ala Glu Gly Asp Pro Glu
290              295              300

Ala Gln Arg Arg Val Ser Lys Asn Ser Lys Tyr Asn Ala Glu Ser Thr
305              310              315              320

Glu Arg Glu Ser Gln Asp Thr Val Ala Glu Asn Asp Asp Gly Gly Phe
         325               330              335

Ser Glu Glu Trp Glu Ala Gln Arg Asp Ser His Leu Gly Pro His Arg
        340                345              350

Ser Thr Pro Glu Ser Arg Ala Ala Val Gln Glu Leu Ser Ser Ser Ile
            355              360              365

Leu Ala Gly Glu Asp Pro Glu Glu Arg Gly Val Lys Leu Gly Leu Gly
        370                375              380

Asp Phe Ile Phe Tyr Ser Val Leu Val Gly Lys Ala Ser Ala Thr Ala
385              390              395              400

Ser Gly Asp Trp Asn Thr Thr Ile Ala Cys Phe Val Ala Ile Leu Ile
               405              410              415

Gly Leu Cys Leu Thr Leu Leu Leu Ala Ile Phe Lys Lys Ala Leu
        420                425              430

Pro Ala Leu Pro Ile Ser Ile Thr Phe Gly Leu Val Phe Tyr Phe Ala
            435              440              445

Thr Asp Tyr Leu Val Gln Pro Phe Met Asp Gln Leu Ala Phe His Gln
      450              455              460

Phe Tyr Ile
465

<210> SEQ ID NO 3
<211> LENGTH: 1347
<212> TYPE: DNA
<213> ORGANISM: Homo sapiens
<220> FEATURE:
<221> NAME/KEY: CDS
<222> LOCATION: (1)..(1347)

<400> SEQUENCE: 3 atg ctc aca ttc atg gcc tct gac agc gag gaa gaa gtg tgt gat gag    48
Met Leu Thr Phe Met Ala Ser Asp Ser Glu Glu Glu Val Cys Asp Glu
1              5                    10                  15 cgg acg tcc cta atg tcg gct gag agc ccc acg ccg cgc tcc tgc cag    96

|  |  |  |  |  |  |  |  |  |  |  |  |  |  |
|---|---|---|---|---|---|---|---|---|---|---|---|---|---|
| Arg | Thr | Ser | Leu | Met | Ser | Ala | Glu | Ser | Pro | Thr | Pro | Arg | Ser | Cys | Gln |
|  |  |  | 20 |  |  |  | 25 |  |  |  | 30 |  |  |

```
gag ggc agg cag ggc cca gag gat gga gag aac act gcc cag tgg aga      144
Glu Gly Arg Gln Gly Pro Glu Asp Gly Glu Asn Thr Ala Gln Trp Arg
         35                  40                  45 agc cag gag aac gag gag gac ggt gag gag gac cct gac cgc tat gtc      192
Ser Gln Glu Asn Glu Glu Asp Gly Glu Glu Asp Pro Asp Arg Tyr Val
 50                  55                  60 tgt agt ggg gtt ccc ggg cgg ccg cca ggc ctg gag gaa gag ctg acc      240
Cys Ser Gly Val Pro Gly Arg Pro Pro Gly Leu Glu Glu Glu Leu Thr
 65                  70                  75                  80 ctc aaa tac gga gcg aag cac gtg atc atg ctg ttt gtg cct gtc act      288
Leu Lys Tyr Gly Ala Lys His Val Ile Met Leu Phe Val Pro Val Thr
                 85                  90                  95 ctg tgc atg atc gtg gtg gta gcc acc atc aag tct gtg cgc ttc tac      336
Leu Cys Met Ile Val Val Val Ala Thr Ile Lys Ser Val Arg Phe Tyr
             100                 105                 110 aca gag aag aat gga cag ctc atc tac acg cca ttc act gag gac aca      384
Thr Glu Lys Asn Gly Gln Leu Ile Tyr Thr Pro Phe Thr Glu Asp Thr
         115                 120                 125 ccc tcg gtg ggc cag cgc ctc ctc aac tcc gtg ctg aac acc ctc atc      432
Pro Ser Val Gly Gln Arg Leu Leu Asn Ser Val Leu Asn Thr Leu Ile
130                 135                 140 atg atc agc gtc atc gtg gtt atg acc atc ttc ttg gtg gtg ctc tac      480
Met Ile Ser Val Ile Val Val Met Thr Ile Phe Leu Val Val Leu Tyr
145                 150                 155                 160 aag tac cgc tgc tac aag ttc atc cat ggc tgg ttg atc atg tct tca      528
Lys Tyr Arg Cys Tyr Lys Phe Ile His Gly Trp Leu Ile Met Ser Ser
                 165                 170                 175 ctg atg ctg ctg ttc ctc ttc acc tat atc tac ctt ggg gaa gtg ctc      576
Leu Met Leu Leu Phe Leu Phe Thr Tyr Ile Tyr Leu Gly Glu Val Leu
             180                 185                 190 aag acc tac aat gtg gcc atg gac tac ccc acc ctc ttg ctg act gtc      624
Lys Thr Tyr Asn Val Ala Met Asp Tyr Pro Thr Leu Leu Leu Thr Val
         195                 200                 205 tgg aac ttc ggg gca gtg ggc atg gtg tgc atc cac tgg aag ggc cct      672
Trp Asn Phe Gly Ala Val Gly Met Val Cys Ile His Trp Lys Gly Pro
210                 215                 220 ctg gtg ctg cag cag gcc tac ctc atc atg atc agt gcg ctc atg gcc      720
Leu Val Leu Gln Gln Ala Tyr Leu Ile Met Ile Ser Ala Leu Met Ala
225                 230                 235                 240 cta gtg ttc atc aag tac ctc cca gag tgg tcc gcg tgg gtc atc ctg      768
Leu Val Phe Ile Lys Tyr Leu Pro Glu Trp Ser Ala Trp Val Ile Leu
                 245                 250                 255 ggc gcc atc tct gtg tat gat ctc gtg gct gtg ctg tgt ccc aaa ggg      816
Gly Ala Ile Ser Val Tyr Asp Leu Val Ala Val Leu Cys Pro Lys Gly
             260                 265                 270 cct ctg aga atg ctg gta gaa act gcc cag gag aga aat gag ccc ata      864
Pro Leu Arg Met Leu Val Glu Thr Ala Gln Glu Arg Asn Glu Pro Ile
         275                 280                 285 ttc cct gcc ctg ata tac tca tct gcc atg gtg tgg acg gtt ggc atg      912
Phe Pro Ala Leu Ile Tyr Ser Ser Ala Met Val Trp Thr Val Gly Met
290                 295                 300 gcg aag ctg gac ccc tcc tct cag ggt gcc ctc cag ctc ccc tac gac      960
Ala Lys Leu Asp Pro Ser Ser Gln Gly Ala Leu Gln Leu Pro Tyr Asp
305                 310                 315                 320 ccg gag atg gaa gaa gac tcc tat gac agt ttt ggg gag cct tca tac     1008
Pro Glu Met Glu Glu Asp Ser Tyr Asp Ser Phe Gly Glu Pro Ser Tyr
                 325                 330                 335
```

```
ccc gaa gtc ttt gag cct ccc ttg act ggg tac cca ggg gag gag ctg    1056
Pro Glu Val Phe Glu Pro Pro Leu Thr Gly Tyr Pro Gly Glu Glu Leu
            340                 345                 350 gag gaa gag gag gaa agg ggc gtg aag ctt ggc ctc ggg gac ttc atc    1104
Glu Glu Glu Glu Glu Arg Gly Val Lys Leu Gly Leu Gly Asp Phe Ile
        355                 360                 365 ttc tac agt gtg ctg gtg ggc aag gcg gct gcc acg ggc agc ggg gac    1152
Phe Tyr Ser Val Leu Val Gly Lys Ala Ala Ala Thr Gly Ser Gly Asp
    370                 375                 380 tgg aat acc acg ctg gcc tgc ttc gtg gcc atc ctc att ggc ttg tgt    1200
Trp Asn Thr Thr Leu Ala Cys Phe Val Ala Ile Leu Ile Gly Leu Cys
385                 390                 395                 400 ctg acc ctc ctg ctg ctt gct gtg ttc aag aag gcg ctg ccc gcc ctc    1248
Leu Thr Leu Leu Leu Leu Ala Val Phe Lys Lys Ala Leu Pro Ala Leu
                405                 410                 415 ccc atc tcc atc acg ttc ggg ctc atc ttt tac ttc tcc acg gac aac    1296
Pro Ile Ser Ile Thr Phe Gly Leu Ile Phe Tyr Phe Ser Thr Asp Asn
            420                 425                 430 ctg gtg cgg ccg ttc atg gac acc ctg gcc tcc cat cag ctc tac atc    1344
Leu Val Arg Pro Phe Met Asp Thr Leu Ala Ser His Gln Leu Tyr Ile
        435                 440                 445 tga                                                                1347

<210> SEQ ID NO 4
<211> LENGTH: 448
<212> TYPE: PRT
<213> ORGANISM: Homo sapiens

<400> SEQUENCE: 4

Met Leu Thr Phe Met Ala Ser Asp Ser Glu Glu Val Cys Asp Glu
1               5                   10                  15

Arg Thr Ser Leu Met Ser Ala Glu Ser Pro Thr Pro Arg Ser Cys Gln
            20                  25                  30

Glu Gly Arg Gln Gly Pro Glu Asp Gly Glu Asn Thr Ala Gln Trp Arg
        35                  40                  45

Ser Gln Glu Asn Glu Glu Asp Gly Glu Glu Asp Pro Asp Arg Tyr Val
    50                  55                  60

Cys Ser Gly Val Pro Gly Arg Pro Pro Gly Leu Glu Glu Leu Thr
65                  70                  75                  80

Leu Lys Tyr Gly Ala Lys His Val Ile Met Leu Phe Val Pro Val Thr
                85                  90                  95

Leu Cys Met Ile Val Val Ala Thr Ile Lys Ser Val Arg Phe Tyr
            100                 105                 110

Thr Glu Lys Asn Gly Gln Leu Ile Tyr Thr Pro Phe Thr Glu Asp Thr
        115                 120                 125

Pro Ser Val Gly Gln Arg Leu Leu Asn Ser Val Leu Asn Thr Leu Ile
    130                 135                 140

Met Ile Ser Val Ile Val Val Met Thr Ile Phe Leu Val Val Leu Tyr
145                 150                 155                 160

Lys Tyr Arg Cys Tyr Lys Phe Ile His Gly Trp Leu Ile Met Ser Ser
                165                 170                 175

Leu Met Leu Leu Phe Leu Phe Thr Tyr Ile Tyr Leu Gly Glu Val Leu
            180                 185                 190

Lys Thr Tyr Asn Val Ala Met Asp Tyr Pro Thr Leu Leu Leu Thr Val
        195                 200                 205

Trp Asn Phe Gly Ala Val Gly Met Val Cys Ile His Trp Lys Gly Pro
    210                 215                 220
```

-continued

```
Leu Val Leu Gln Gln Ala Tyr Leu Ile Met Ile Ser Ala Leu Met Ala
225                 230                 235                 240

Leu Val Phe Ile Lys Tyr Leu Pro Glu Trp Ser Ala Trp Val Ile Leu
                245                 250                 255

Gly Ala Ile Ser Val Tyr Asp Leu Val Ala Val Leu Cys Pro Lys Gly
            260                 265                 270

Pro Leu Arg Met Leu Val Glu Thr Ala Gln Glu Arg Asn Glu Pro Ile
        275                 280                 285

Phe Pro Ala Leu Ile Tyr Ser Ser Ala Met Val Trp Thr Val Gly Met
    290                 295                 300

Ala Lys Leu Asp Pro Ser Ser Gln Gly Ala Leu Gln Leu Pro Tyr Asp
305                 310                 315                 320

Pro Glu Met Glu Glu Asp Ser Tyr Asp Ser Phe Gly Glu Pro Ser Tyr
                325                 330                 335

Pro Glu Val Phe Glu Pro Pro Leu Thr Gly Tyr Pro Gly Glu Glu Leu
            340                 345                 350

Glu Glu Glu Glu Glu Arg Gly Val Lys Leu Gly Leu Gly Asp Phe Ile
        355                 360                 365

Phe Tyr Ser Val Leu Val Gly Lys Ala Ala Ala Thr Gly Ser Gly Asp
    370                 375                 380

Trp Asn Thr Thr Leu Ala Cys Phe Val Ala Ile Leu Ile Gly Leu Cys
385                 390                 395                 400

Leu Thr Leu Leu Leu Leu Ala Val Phe Lys Lys Ala Leu Pro Ala Leu
                405                 410                 415

Pro Ile Ser Ile Thr Phe Gly Leu Ile Phe Tyr Phe Ser Thr Asp Asn
            420                 425                 430

Leu Val Arg Pro Phe Met Asp Thr Leu Ala Ser His Gln Leu Tyr Ile
        435                 440                 445
```

<210> SEQ ID NO 5
<211> LENGTH: 8
<212> TYPE: PRT
<213> ORGANISM: Artificial Sequence
<220> FEATURE:
<223> OTHER INFORMATION: Peptide Fragment of Presenilin

<400> SEQUENCE: 5

```
Asp Glu Glu Glu Asp Glu Glu Leu
1               5
```

<210> SEQ ID NO 6
<211> LENGTH: 15
<212> TYPE: PRT
<213> ORGANISM: Artificial Sequence
<220> FEATURE:
<223> OTHER INFORMATION: Peptide Fragment of Presenilin

<400> SEQUENCE: 6

```
Arg Arg Ser Leu Gly His Pro Glu Pro Leu Ser Asn Gly Arg Pro
1               5                   10                  15
```

<210> SEQ ID NO 7
<211> LENGTH: 40
<212> TYPE: PRT
<213> ORGANISM: Artificial Sequence
<220> FEATURE:
<223> OTHER INFORMATION: Peptide Fragment of Presenilin

<400> SEQUENCE: 7

```
Arg Arg Ser Leu Gly His Pro Glu Pro Leu Ser Asn Gly Arg Pro Gln
1               5                   10                  15

Gly Asn Ser Arg Gln Val Val Glu Gln Asp Glu Glu Asp Glu Glu
            20                  25                  30

Leu Thr Leu Lys Tyr Gly Ala Lys
        35                  40

<210> SEQ ID NO 8
<211> LENGTH: 20
<212> TYPE: PRT
<213> ORGANISM: Artificial Sequence
<220> FEATURE:
<223> OTHER INFORMATION: Peptide Fragment of Presenilin

<400> SEQUENCE: 8

Lys Lys Ala Leu Pro Ala Leu Pro Ile Ser Ile Thr Phe Gly Leu Val
1               5                   10                  15

Phe Tyr Phe Ala
            20

<210> SEQ ID NO 9
<211> LENGTH: 11
<212> TYPE: PRT
<213> ORGANISM: Artificial Sequence
<220> FEATURE:
<223> OTHER INFORMATION: Peptide Fragment of Presenilin

<400> SEQUENCE: 9

Met Ala Leu Val Phe Ile Lys Tyr Leu Pro Glu
1               5                   10

<210> SEQ ID NO 10
<211> LENGTH: 4
<212> TYPE: PRT
<213> ORGANISM: Artificial Sequence
<220> FEATURE:
<223> OTHER INFORMATION: Consensus Sequence for SH3 binding
<220> FEATURE:
<221> NAME/KEY: MISC_FEATURE
<222> LOCATION: (2)..(3)
<223> OTHER INFORMATION: Xaa is any amino acid

<400> SEQUENCE: 10

Pro Xaa Xaa Pro
1

<210> SEQ ID NO 11
<211> LENGTH: 7
<212> TYPE: PRT
<213> ORGANISM: Artificial Sequence
<220> FEATURE:
<223> OTHER INFORMATION: Consensus sequence for SH3 binding
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (5)..(5)
<223> OTHER INFORMATION: Xaa is any amino acid
<220> FEATURE:
<221> NAME/KEY: MISC_FEATURE
<222> LOCATION: (6)..(6)
<223> OTHER INFORMATION: Xaa is Arg or a hydrophobic residue

<400> SEQUENCE: 11

Arg Xaa Leu Pro Xaa Xaa Pro
1               5
```

```
<210> SEQ ID NO 12
<211> LENGTH: 13
<212> TYPE: PRT
<213> ORGANISM: Artificial Sequence
<220> FEATURE:
<223> OTHER INFORMATION: Src peptide substrate

<400> SEQUENCE: 12

Lys Val Glu Lys Ile Gly Thr Tyr Gly Val Val Lys Lys
1               5                   10

<210> SEQ ID NO 13
<211> LENGTH: 15
<212> TYPE: PRT
<213> ORGANISM: Artificial Sequence
<220> FEATURE:
<223> OTHER INFORMATION: Control peptide for Src assay

<400> SEQUENCE: 13

Lys Val Glu Lys Ile Gly Val Gly Ser Tyr Gly Val Val Lys Lys
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Control peptide for Src assay

<400> SEQUENCE: 14

Lys Val Glu Lys Ile Gly Glu Gly Thr Phe Gly Val Val Lys Lys
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: Peptide Fragment of Presenilin

<400> SEQUENCE: 15

Ser Asn Gly Arg Pro Gln Gly Asn Ser Arg Gln Val Val Glu Gln
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Peptide Fragment of Presenilin

<400> SEQUENCE: 16

Arg Gln Val Val Glu Gln Asp Glu Glu Glu Asp Glu Glu Leu Thr
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Peptide Fragment of Presenilin

<400> SEQUENCE: 17

Asp Glu Glu Glu Asp Glu Glu Leu Thr Leu Lys Tyr Gly Ala Lys
1               5                   10                  15
```

```
<210> SEQ ID NO 18
<211> LENGTH: 11
<212> TYPE: PRT
<213> ORGANISM: Artificial Sequence
<220> FEATURE:
<223> OTHER INFORMATION: G-protein peptide fragment

<400> SEQUENCE: 18

Ile Lys Asn Asn Leu Lys Asp Cys Gly Leu Phe
1               5                   10

<210> SEQ ID NO 19
<211> LENGTH: 11
<212> TYPE: PRT
<213> ORGANISM: Artificial Sequence
<220> FEATURE:
<223> OTHER INFORMATION: G-protein peptide fragment

<400> SEQUENCE: 19

Ile Lys Asn Asn Leu Lys Glu Cys Gly Leu Tyr
1               5                   10

<210> SEQ ID NO 20
<211> LENGTH: 11
<212> TYPE: PRT
<213> ORGANISM: Artificial Sequence
<220> FEATURE:
<223> OTHER INFORMATION: G-protein peptide fragment

<400> SEQUENCE: 20

Ile Ala Asn Asn Leu Arg Gly Cys Gly Leu Tyr
1               5                   10

<210> SEQ ID NO 21
<211> LENGTH: 11
<212> TYPE: PRT
<213> ORGANISM: Artificial Sequence
<220> FEATURE:
<223> OTHER INFORMATION: G-protein peptide fragment

<400> SEQUENCE: 21

Ile Ala Lys Asn Leu Arg Gly Cys Gly Leu Tyr
1               5                   10

<210> SEQ ID NO 22
<211> LENGTH: 11
<212> TYPE: PRT
<213> ORGANISM: Artificial Sequence
<220> FEATURE:
<223> OTHER INFORMATION: G-protein peptide fragment

<400> SEQUENCE: 22

Ile Gln Asn Asn Leu Lys Tyr Ile Gly Leu Cys
1               5                   10

<210> SEQ ID NO 23
<211> LENGTH: 11
<212> TYPE: PRT
<213> ORGANISM: Artificial Sequence
<220> FEATURE:
<223> OTHER INFORMATION: G-protein peptide fragment

<400> SEQUENCE: 23

Gln Arg Met His Leu Arg Gln Tyr Glu Leu Leu
1               5                   10
```

```
<210> SEQ ID NO 24
<211> LENGTH: 11
<212> TYPE: PRT
<213> ORGANISM: Artificial Sequence
<220> FEATURE:
<223> OTHER INFORMATION: G-protein peptide fragment

<400> SEQUENCE: 24

Gln Arg Met His Leu Lys Gln Tyr Glu Leu Leu
1               5                   10

<210> SEQ ID NO 25
<211> LENGTH: 11
<212> TYPE: PRT
<213> ORGANISM: Artificial Sequence
<220> FEATURE:
<223> OTHER INFORMATION: G-protein peptide fragment

<400> SEQUENCE: 25

Leu Gln Leu Asn Leu Lys Glu Tyr Asn Ala Val
1               5                   10
```